US008188339B2

(12) United States Patent
Mittendorf et al.

(10) Patent No.: US 8,188,339 B2
(45) Date of Patent: May 29, 2012

(54) SUGAR AND LIPID METABOLISM REGULATORS IN PLANTS IV

(75) Inventors: Volker Mittendorf, Hillsborough, NC (US); Heiko A. Haertel, Berlin (DE); Jörg Bauer, Limburgerhof (DE); Oliver Oswald, Ludwigshafen (DE)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 12/943,078

(22) Filed: Nov. 10, 2010

(65) Prior Publication Data

US 2011/0055972 A1 Mar. 3, 2011

Related U.S. Application Data

(62) Division of application No. 10/523,503, filed as application No. PCT/US03/24364 on Aug. 4, 2003.

(60) Provisional application No. 60/400,803, filed on Aug. 2, 2002.

(51) Int. Cl.
*A01H 5/00* (2006.01)
*C12N 15/82* (2006.01)

(52) U.S. Cl. ...................... 800/298; 800/281; 435/320.1

(58) Field of Classification Search ........................ None
See application file for complete search history.

(56) References Cited

U.S. PATENT DOCUMENTS

| | | | |
|---|---|---|---|
| 4,956,282 | A | 9/1990 | Goodman et al. |
| 5,777,201 | A | 7/1998 | Poutre et al. |
| 5,955,650 | A | 9/1999 | Hitz |
| 6,084,164 | A | 7/2000 | Bidney et al. |
| 6,271,440 | B1 | 8/2001 | Gubler et al. |
| 6,274,379 | B1 | 8/2001 | Famodu et al. |
| 6,593,514 | B1 | 7/2003 | Cahoon et al. |
| 2002/0023281 | A1 | 2/2002 | Gorlach et al. |
| 2002/0040489 | A1 | 4/2002 | Gorlach et al. |
| 2002/0059663 | A1 | 5/2002 | Gorlach et al. |
| 2004/0072159 | A1 | 4/2004 | Takaiwa et al. |
| 2004/0086989 | A1 | 5/2004 | Badur et al. |

FOREIGN PATENT DOCUMENTS

| | | | |
|---|---|---|---|
| CA | 2 307 960 | A1 | 11/2000 |
| EP | 1 033 405 | A2 | 9/2000 |
| WO | WO-91/19806 | | 12/1991 |
| WO | WO-94/11516 | | 5/1994 |
| WO | WO-94/28141 | | 12/1994 |
| WO | WO-96/07742 | A1 | 3/1996 |
| WO | WO-97/35983 | | 10/1997 |
| WO | WO-98/35044 | | 8/1998 |
| WO | WO-98/45461 | A1 | 10/1998 |
| WO | WO-98/54954 | | 12/1998 |
| WO | WO-98/59057 | | 12/1998 |
| WO | WO-99/41974 | | 8/1999 |
| WO | WO-99/53073 | | 10/1999 |
| WO | WO-00/11012 | | 3/2000 |
| WO | WO-00/22092 | | 4/2000 |
| WO | WO-00/36117 | | 6/2000 |
| WO | WO-00/73461 | A1 | 12/2000 |
| WO | WO-01/29238 | A2 | 4/2001 |
| WO | WO-01/35725 | A1 | 5/2001 |
| WO | WO-01/38484 | A2 | 5/2001 |
| WO | WO-01/66777 | A1 | 9/2001 |
| WO | WO-01/77311 | A2 | 10/2001 |
| WO | WO-02/10210 | A2 | 2/2002 |
| WO | WO-02/16655 | A2 | 2/2002 |
| WO | WO-02/22821 | A2 | 3/2002 |
| WO | WO-02/31154 | A1 | 4/2002 |
| WO | WO-02/072848 | A2 | 9/2002 |
| WO | WO-03/000898 | A1 | 1/2003 |
| WO | WO-03/008440 | A2 | 1/2003 |
| WO | WO-03/014376 | A2 | 2/2003 |
| WO | WO-03/027249 | A2 | 4/2003 |
| WO | WO-2004/007712 | A2 | 1/2004 |
| WO | WO-2004/035798 | A2 | 4/2004 |

OTHER PUBLICATIONS

Doerks et al, TIG 14(6): 248-250, Jun. 1998.*
Brenner, SE, TIG 15(4): 132-133, Apr. 1999.*
European Search Report, European Application No. EP 10 17 4677, May 24, 2011.
"RecName: Full=Phosphatidate cytidylyltransferase; EC=2.7.7.41," Yamada, K., et al., Database Accession No. Q94A03, Dec. 1, 2001.
Arondel, V., et al., "Lipid Transfer Proteins are Encoded by a Small Multigene Family in *Arabidopsis thaliana*", Plant Science, vol. 157, No. 1, (2000), pp. 1-12.
Bensmihen, S., et al., "The Homologous ABI5 and EEL Transcription Factors Function Antagonistically to Fine-Tune Gene Expression during Late Embryogenesis", The Plant Cell, vol. 14, No. 6, (2002), pp. 1391-1403.
Finkelstein, R.R., "Abscisic Acid-insensitive Mutations Provide Evidence for Stage-Specific Signal Pathways Regulating Expression of an *Arabidopsis* Late Embryogenesis-abundant (*lea* ) Gene", Mol. Gen Genet, vol. 238, No. 3, (1993) pp. 401-408.
Gaubier, P, et al., "Two Different *Em*-like Genes are Expressed in *Arabidopsis thaliana* seeds during Maturation", Mol. Gen Genet, vol. 238, No. 3, (1993), pp. 409-418.
Jakoby, M., et al., "bZIP Transcription Factors in *Arabidopsis*" Trends in Plant Science, vol. 7, No. 3, (2002), pp. 106-111. Li, X.P., "A Pigment-binding Protein Essential for Regulation of Photosynthetic Light Harvesting", Nature, vol. 403, No. 6768, (2000), pp. 391-395.
Wang, M.L., et al., "A Cluster of ABA-Regulated Genes on *Arabidopsis thaliana* BAC T07M07", Genome Research, vol. 9, No. 4, (1999), pp. 325-333.
"*Arabidopsis thaliana* At5g53970 mRNA Sequence", EMBL Database, Accession No. AY113848, Jun. 5, 2002.
"*Arabidopsis thaliana* unknown protein (Atlgl6850) mRNA, complete cds", EMBL Database, Accession No. AY080886, Mar. 15, 2002.
"*Arabidopsis thaliana* unknown protein (At3q48410) mRNA, complete cds", EMBL Database, Accession No. AY065282, Dec. 13, 2001.
"*Arabidopsis thaliana* At3g03380/T21P5_20 mRNA, complete cds", EMBL Database, Accession No. AY078951, Mar. 13, 2002.
"*Arabidopsis thaliana* cDAN clone:RAFL15-46-F10, 3'-end", EMBL Database, Accession No. AU228084, Mar. 19, 2002.
"*Arabidopsis thaliana* bZIP protein DPBF4 mRNA, complete cds", EMBL Database, Accession No. AF334209, Mar. 19, 2001.

(Continued)

*Primary Examiner* — Elizabeth McElwain

(74) *Attorney, Agent, or Firm* — Connolly Bove Lodge & Hutz LLP

(57) ABSTRACT

Isolated nucleic acids and proteins associated with lipid and sugar metabolism regulation are provided. In particular, lipid metabolism proteins (LMP) and encoding nucleic acids originating from *Arabidopsis thaliana, Brassica napus*, and *Physcomitrella patens* are provided. The nucleic acids and proteins are used in methods of producing transgenic plants and modulating levels of seed storage compounds. Preferably, the seed storage compounds are lipids, fatty acids, starches, or seed storage proteins.

17 Claims, No Drawings

OTHER PUBLICATIONS

"*Arabidopsis thaliana* partial mRNA for basic leucine zipper transcription factor (atbzipl2 gene)", EMBL Database, Accession No. AJ420881, Jul. 3, 2002.
"*Arabidopsis thaliana* unknown protein (At1g02700) mRNA, complete cds", EMBL Database, Accession No. AY056328, Oct. 2, 2001.
"*Arabidopsis thaliana* At2g36580/F1011.21 mRNA, complete cds" EMBL Database, Accession No. AY069894, Dec. 28, 2001.
"*Arabidopsis thaliana* putative phosphatidylglycerotransferase (At4g04870) mRNA, complete cds", EMBL Database, Accession No. AY059735, Nov. 5, 2001.
"*Arabidopsis thaliana* putative phosphatidate cytidylyltransferase (At2g45150) mRNA, complete cds", EMBL Database, Accession No. AY050778, Aug. 27, 2001.
"*Arabidopsis thaliana* PsbS protein (PsbS) mRNA, complete cds", EMBL Database, Accession No. AF134131, May 5, 1999.
"701555010 *A. thaliana*, Columbia Col-0, rosette-3 *Arabidopsis thaliana* cDNA close 701555010, mRNA sequence", EMBL Database, Accession No. Al999223, Sep. 9, 1999.
"*A. thaliana* mRNA for gibberellin 20-oxidase (1425 bp)" EMBL Database, Accession No. X83381, Dec. 7, 1995.
"*Arabidopsis thaliana* cDNA clone:RAFL19-83-J04, 5'-end", EMBL Database, Accession No. AU239460, Mar. 23, 2002.
"*Arabidopsis thaliana* chromosome 2 clone F14N22 map mi551, complete sequence", EMBL Database, Accession No. AC007087, Mar. 23, 1999.
"*Arabidopsis thaliana* Atlg62710/F23N19_8 mRNA, complete cds", EMBL Database, Accession No, AY059156, Oct. 26, 2001.
"*Arabidopsis thaliana* clone 98340 mRNA, complete sequence", EMBL Database, Accession No. AY088879, Jun. 14, 2002.
"*Arabidopsis thaliana* ERD9 mRNA for glutathione S-transferase, complete cds", EMBL Database, Accession No. AB039930, Aug. 28, 2001.
"*Arabidopsis thaliana* At1g10370 mRNA sequence", EMBL Database, Accession No. AY091102, Apr. 23, 2002.
"*Arabidopsis thaliana* chromosome I glutathione S-transferase (GST30) mRNA, complete cds", EMBL Database, Accession No. AF288191, Nov. 6, 2000.
"*A. Thaliana* Em-like protein (Em6c2)", EMBL Database, Accession No. Z11924, May 18, 1993.
"*Arabidopsis thaliana* putative ABA-regulated protein ATEM6 (At2g40170) mRNA, complete cds", EMBL Database, Accession No. AF360157, Mar. 22, 2001.
"*Arabidopsis thaliana* cysteine proteinase (GCP1) mRNA, complete cds", EMBL Database, Accession No, AY043294, Aug. 26, 2001.
"*Arabidopsis thaliana* genomic DNA, chromosome 5, P1 clone: MJE7", EMBL Database, Accession No. AB020745, Dec. 14, 1998.
"*Arabidopsis thaliana* unknown protein (At1g69460) mRNA, complete cds", EMBL Database, Accession No. AY114598, Jun. 11, 2002.
"*Arabidopsis thaliana* At1g54870/F14C21_16 mRNA, complete cds", EMBL Database, Accession No. AY124852, Jul. 8, 2002.
"*Arabidopsis thaliana* clone 35786 mRNA, complete sequence", EMBL Database, Accession No. AY087472, Jun. 14, 2002.
"*Arabidopsis thaliana* cDNA clone: RAFL19-41-A06, 5'-end", EMBL Database, Accession No. AU238975, Mar. 23, 2002.
"M55B3STM *Arabidopsis* developing seed *Arabidopsis thaliana* cDNA clone M55B3 5', mRNA sequence", EMBL Database, Accession No. BE524857, Aug. 10, 2000.
"Glycine max seed matuation protein PM38 (PM38) mRNA, complete cds", EMBL Database, Accession No. AF169023, Sep. 1, 1999.
"*Arabidopsis thaliana* cell division cycle protein (CDC48) mRNA, complete cds", EMBL Database, Accession No. U37587, Oct. 16, 1995.
"Glycine max valosin-containing protein mRNA, complete cds", EMBL Database, Accession No. U20213, Jun. 19, 1995.
*Arabidopsis thaliana* DNA chromosome 4, contig fragment No. 75, EMBL Database, Accession No. AL161579, Mar. 16, 2000.
"*Arabidopsis thaliana* cDNA clone: RZL54e10F, 3' end", EMBL Database, Accession No. AV548453, Jun. 16, 2000.
"*Arabidopsis thaliana* putative protein disulfide-isomerase (At2g47470) mRNA, complete cds", EMBL Database, Accession No. AY091388, Apr. 22, 2002.
"*Arabidopsis thaliana* AT5g45690/MRA19_8 mRNA, complete cds", EMBL Database, Accession No. AY052317, Sep. 6, 2001.
"*Arabidopsis thaliana* annexin (AnnAt1) mRNA, complete cds", EMBL Database, Accession No. AF083913, Jun. 3, 1999.
"*A. thaliana* transcribed sequence; clone YAY177; 5' end; Similar to Corticosteroid 11-beta-dehydrogenase; rattus norvegicus", EMBL Database, Accession No. Z35038, Jun. 8, 1994.
"Putative oxidoreductase", UniProt Database, Accession No. Q9T0G0, May 1, 2000.
"*Arabidopsis thaliana* unknown protein (At4g13010) mRNA, complete cds", EMBL Database, Accession No. AY117154, Jun. 18, 2002.
"*Arabidopsis thaliana* AT1g12010/F12F1_12 mRNA, complete cds", EMBL Database, EMBL Database. Accession No. AY052694, Sep. 6, 2001.
"*Arabidopsis thaliana* At5g01670 mRNA for putative aldose reductase, complete cds, close: RAFL19-21-M03", EMBL Database, Accession No. AK118010, Dec. 13, 2002.
"Nonspecific lipid-transfer protein 2 precursor (LTP2)", GenBank, Accession No. Q9S713, Dec. 1, 2000.
"Poly [ADP-ribose] polymerase 3 (PARP-3) (ADPRT 3) (NAD(+) ADP-ribosyltransferase 3) (Poly[ADP-ribose] synthetase 3)", GenBank, Accession No. Q9FK91, Nov. 28, 2006.
"Putative seed maturation protein", GenBank, Accession No. Q9SIN3, May 1, 2000.
Vacuolar-processing enzyme beta-isozyme precursor (Beta-VPE), GenBank, Accession No. Q39044, Jul. 11, 2002.
Stein, et al., (Nature Biotechnol. (Mar. 1999) 17:209).
Truksa, M., et al., "Molecular analysis of flax 2S storage protein conlinin and seed specific activity of its promoter", Plant Physiology and Biochemistry, vol. 41, No. 2, (2003), pp. 141-147(7).
Dorman, et al., *Arabidopsis Galactolipid* biosynthesis and lipid trafficking mediated by DGD1, Science, (1999), vol. 284, pp. 2181-2184.
Levin, "Levin-1", N_Geneseq Database, Accession No. ADB95043, WO/2003/008440 (SEQ ID No: 41), published Jan. 30, 2003.
Doerks, et al., "Protein Annotation: Detective Work for Function Prediction", TIG, vol. 14, No. 6, (1998), pp. 248-250.
Bartoszewski, et al., J. Amer. Hort. Sco., vol. 127, vol. 4, (2002), pp. 535-539.
Arenas-Huertero et al., 2000, Genes Dev. 14:2085-2096.
Beaudoin et al., 2000, Plant Cell, 2000: 1103-1115.
Brenner, 1976, Adv. Exp. Med. Biol. 83: 85-101.
Browse et al., 1986, Biochemical J. 235:25-31.
Cahoon et al., 1992, Proc. Natl. Acad. Sci. USA 89:11184-11188.
Cohen, 1992, Trends Biochem. Sci. 17:408-413.
Colon-Carmona et al., 2000, Plant Physiol. 124:1728-1738.
Frentzen, 1998, Lipids, 100:161-166.
Herzog et al., 1995, "GASA, a gibberellin-regulated gene family from *Arabidopsis thaliana* related to the tomato GAST1 gene", Plant Mol. Biol. 27(4) 743-752.
Herzog et al., 1995, Database GenEMBL, Accession U11764.
Kang & Rawsthorne, 1994, Plant J., 6:795-805.
Kuo et al., 1996, Plant Cell, 8:259-269.
Millar et al., 2000, Trends Plant Sci., 5:95-101.
Ohlrogge & Browse, 1995, Plant Cell, 7:957-970.
Plaxton, 1996, Annu. Rev. Plant Physiol. Plant Mol. Biol., 47:185-214.
Ritchie & Gilroy, 1998, Plant Physiol., 116:765-776.
Shanklin & Cahoon, 1998, Annu. Rev. Plant Physiol. Plant Mol. Biol., 49:611-641.
Töpfer et al., 1995, Science, 268:681-686.
Van de Loo, F. J. et al., 1993, Unusual Fatty Acids in Lipid Metabolism in Plants, pp. 91-126, editor TS Moore, Jr. CRC Press.
Van de Loo et al., 1995, Proc. Natl. Acad. Sci USA, 92:6743-6747.
Voelker, 1996, Genetic Engineering ed.:Setlow, 18:111-113.
Zhou et al., 1998, Proc. Natl. Acad. Sci. USA, 95:10294-10299.
The *Arabidopsis* Genome Initiative 2000 Analysis of the genome sequence of the flowering plant *Arabidopsis thaliana*, Nature, 408:796-844.
Beisson, et al., "An esterase neosynthesized post-germinated sunflower seeds is related to a new family of lipolytic enzymes," Plant Physiol. Biochem, vol. 35, No. 10, (1997), pp. 761-765.

Buhr et al., "Ribozyme termination of RNA transcripts down-regulate seed fatty acid genes in transgenic soybean", The Plant Journal, vol. 30, No. 2, (2002), pp. 155-163.
Eccleston and Ohlrogge, "Expression of Lauroyl-Acyl Carrier Protein Thioesterase in *Brassica napus* Seeds Induces Pathways for Both Fatty Acid Oxidation and Biosynthesis and Implies a Set Point for Triacyglycerol Accumulation", The Plant Cell, vol. 10, (1998), pp. 613-621.
Focks & Benning, "wrinkled1: A Novel, Low-Seed-Oil Mutant of *Arabidopsis* with a Deficiency in the Seed-Specific Regulation of Carbohydrate Metabolism", Plant Physiol., vol. 118, (1998), pp. 91-101.
Härtel et al., "DGD1-independent biosynthesis of extraplastidic galactolipids after phosphate deprivation in *Arabidopsis*", Proc. Natl. Acad. Sci. USA, vol. 97, No. 19, (2000), pp. 10649-10654.
Hatje et al., "World Importance of Oil Crops and Their Products", Oil Crops of the World-Their Breeding and Utilization, eds. Röbbelen, Downey, and Ashri, (1989), pp. 1-21.
Höfgen and Willmitzer, "Biochemical and Genetic Analysis of Different Patatin Isoforms Expressed in Various Organs of Potato (*Solanum Tuberosum*)", Plant Sci., vol. 66, (1990), pp. 221-230.
Holvoet et al., "The Arg123-Tyr166 Central Domain of Human ApoAl is Critical for Lecithin:Cholesterol Acyltransferase-Induced Hyperalphalipoproteinemia and HDL Remodeling in Transgenic Mice", Arteriosclerosis Thrombosis Vascular Biology, (2000), pp. 459-466.
Hurry et al., "The role of inorganic phosphate in the development of freezing tolerance and the acclimatization of photosynthesis of low temperature is revealed by the *pho* mutants of *Arabidopsis thaliana*", The Plant Journal, vol. 24, No. 3, (2000), pp. 383-396.
Kinney et al., "Genetic Modification of the Storage Lipids of Plants", Current Opin. in Biotech., vol. 5, (1994), pp. 144-151.
Mahmoud and Croteau, "Metabolic Engineering of Essential Oil Yield and Composition in Mint by Altering Expression of Deoxyxylulose Phosphate Reductoisomerase and Menithofuran Synthase", Proc. Natl. Acad. Sci. USA, vol. 98, No. 15, (2001), pp. 8915-8920.
Merlot et al., "The ABI1 and ABI2 protein phosphatases 2C act in a negative feedback regulatory loop of the abscisic acid signaling pathway", The Plant Journal, vol. 15, No. 3, (2001), pp. 295-303.
Metz et al., "Purification of a Jojoba Embryo Fatty Acyl-Coenzyme A Reductase and Expression of its cDNA in High Erucic Acid Rapeseed", Plant Physiology, vol. 122, (2000), pp. 635-644.
Meyer et al., "A protein phosphatase 2C involved in ABA signal transduction in *Arabidopsis thaliana*", Science, vol. 264, (1994), pp. 1452-1455.
Mitsukawa et al, "Overexpression of an *Arabidopsis thaliana* high-affinity phosphate transporter gene in tobacco cultured cells enhances cell growth under phosphage-limited conditions", Proc. Natl. Acad. Sci. USA, vol. 94, No. 13, (1997), pp. 7098-7102.
Mueller et al., "Lipid Phosphorylation in Chloroplast Envelopes", The Journal of Biological Chemistry, vol. 275, No. 26, (2000), pp. 19475-19581.
Ogas et al., "Cellular Differentiation Regulated by Gibberellin in the *Arabidopsis thaliana* pickle Mutant", Science, vol. 277, (1998), pp. 91-94.
Ogas et al., "Pickle is a CHD3 chromatin-remodeling factor that regulates the transition from embryonic to vegetative development in *Arabidopsis*", Proc. Natl. Acad. Sci. USA, vol. 96, (1999), pp. 13839-13844.
Ohlrogge et al., "Fatty acid synthesis: from $CO_2$ to functional genomics", Biochem. Soc., Trans., vol. 28, No. 6, (2000), pp. 567-573.
Parveez, et al., "Transgenic Oil Palm: Production and Projection," Biochem. Soc. Trans., vol. 28, No. 6, (2000), p. 969.
Savage & Ohlrogge, "Phosphorylation of pea chloroplast acetyl-CoA carboxylase", The Plant Journal, vol. 18, No. 5, (1999), pp. 521-527.
White et al., "A New Set of *Arabidopsis* Expressed Sequence Tags from Developing Seeds. The Metabolic Pathway from Carbohydrates to Seed Oil", Plant Physiol., vol. 124, (2000), pp. 1582-1594.
Zou et al., "Modification of Seed Oil Content and Acyl Composition in the Brassicaceae by Expression of a Yeast sn-2 Acyltransferase Gene", Plant Cell, vol. 9, (1997), pp. 909-923.
Girke, et al., "Identification of a Novel Delta6-Acyl-Group Desaturase by Targeted Gene Disruption in *Physcomitrella Patens*", Plant Journal, vol. 15, No. 1, (1998), pp. 39-48.
Thoma et al., "Tissue-Specific Expression of a Gene Encoding a Cell Wall-Localized Lipid Transfer Protein from *Arabidopsis*", Plant Physiology, vol. 105, (1994), pp. 35-45.

* cited by examiner

SEQUENCE LISTING

```
<160> NUMBER OF SEQ ID NOS: 163

<210> SEQ ID NO 1
<211> LENGTH: 300
<212> TYPE: DNA
<213> ORGANISM: Arabidopsis thaliana

<400> SEQUENCE: 1

atggcaatct tccgaagtac actagtttta ctgctgatcc tcttctgcct caccactttt     60

gagcttcatg ttcatgctgc tgaagattca caagtcggtg aaggcgtagt gaaaattgat    120

tgcggtggga gatgcaaagg tagatgcagc aaatcgtcga ggccaaatct gtgtttgaga    180

gcatgcaaca gctgttgtta ccgctgcaac tgtgtgccac caggcaccgc cgggaaccac    240

cacctttgtc cttgctacgc ctccattacc actcgtggtg gccgtctcaa gtgcccttaa    300


<210> SEQ ID NO 2
<211> LENGTH: 99
<212> TYPE: PRT
<213> ORGANISM: Arabidopsis thaliana

<400> SEQUENCE: 2

Met Ala Ile Phe Arg Ser Thr Leu Val Leu Leu Leu Ile Leu Phe Cys
1               5                   10                  15

Leu Thr Thr Phe Glu Leu His Val His Ala Ala Glu Asp Ser Gln Val
            20                  25                  30

Gly Glu Gly Val Val Lys Ile Asp Cys Gly Gly Arg Cys Lys Gly Arg
        35                  40                  45

Cys Ser Lys Ser Ser Arg Pro Asn Leu Cys Leu Arg Ala Cys Asn Ser
    50                  55                  60

Cys Cys Tyr Arg Cys Asn Cys Val Pro Pro Gly Thr Ala Gly Asn His
65                  70                  75                  80

His Leu Cys Pro Cys Tyr Ala Ser Ile Thr Thr Arg Gly Gly Arg Leu
                85                  90                  95

Lys Cys Pro


<210> SEQ ID NO 3
```

<211> LENGTH: 1245
<212> TYPE: DNA
<213> ORGANISM: Arabidopsis thaliana

<400> SEQUENCE: 3

```
atggagaatg gagcaacgac gacgagcaca attaccatca aagggattct gagtttgcta     60

atggaaagca tcacaacaga ggaagatgaa ggaggaaaga gagtaatatc tctgggaatg    120

ggagacccaa cactctactc gtgttttcgt acaacacaag tctctcttca agctgtttct    180

gattctcttc tctccaacaa gttccatggt tactctccta ccgtcggtct tccccaagct    240

cgaagggcaa tagcagagta tctatcgcgt gatcttccat acaaactttc acaggatgat    300

gtgtttatca catcgggttg cacgcaagcg atcgatgtag cattgtcgat gttagctcgt    360

cccagggcta atatacttct tccaaggcct ggtttcccaa tctatgaact ctgtgctaag    420

tttagacacc ttgaagttcg ctacgtcgat cttcttccgg aaaatggatg ggagatcgat    480

cttgatgctg tcgaggctct tgcagacgaa aacacggttg ctttggttgt tataaaccct    540

ggtaatcctt gcgggaatgt ctatagctac cagcatttga tgaagattgc ggaatcggcg    600

aaaaaactag ggtttcttgt gattgctgat gaggtttacg gtcatcttgc ttttggtagc    660

aaaccgtttg tgccaatggg tgtgtttgga tctattgttc ctgtgcttac tcttggctct    720

ttatcaaaga gatggatagt tccaggttgg cgactcgggt ggtttgtcac cactgatcct    780

tctggttcct ttaaggaccc taagatcatt gagaggttta agaaatactt tgatattctt    840

ggtggaccag ctacatttat tcaggctgca gttcccacta ttttggaaca gacggatgag    900

tctttcttca agaaaacctt gaactcgttg aagaactctt cggatatttg ttgtgactgg    960

atcaaggaga ttccttgcat tgattcctcg catcgaccag aaggatccat ggcaatgatg   1020

gttaagctga atctctcatt acttgaagat gtaagtgacg atatcgactt ctgtttcaag   1080

ttagctaggg aagaatcagt catccttctt cctgggaccg cggtggggct gaagaactgg   1140

ctgaggataa cgtttgcagc agatgcaact tcgattgaag aagcttttaa aaggatcaaa   1200

tgtttctatc ttagacatgc caagactcaa tatccaacca tatag                   1245
```

<210> SEQ ID NO 4
<211> LENGTH: 414
<212> TYPE: PRT
<213> ORGANISM: Arabidopsis thaliana

<400> SEQUENCE: 4

```
Met Glu Asn Gly Ala Thr Thr Thr Ser Thr Ile Thr Ile Lys Gly Ile
1               5                   10                  15

Leu Ser Leu Leu Met Glu Ser Ile Thr Thr Glu Glu Asp Glu Gly Gly
            20                  25                  30

Lys Arg Val Ile Ser Leu Gly Met Gly Asp Pro Thr Leu Tyr Ser Cys
        35                  40                  45

Phe Arg Thr Thr Gln Val Ser Leu Gln Ala Val Ser Asp Ser Leu Leu
    50                  55                  60

Ser Asn Lys Phe His Gly Tyr Ser Pro Thr Val Gly Leu Pro Gln Ala
65                  70                  75                  80

Arg Arg Ala Ile Ala Glu Tyr Leu Ser Arg Asp Leu Pro Tyr Lys Leu
                85                  90                  95

Ser Gln Asp Asp Val Phe Ile Thr Ser Gly Cys Thr Gln Ala Ile Asp
            100                 105                 110

Val Ala Leu Ser Met Leu Ala Arg Pro Arg Ala Asn Ile Leu Leu Pro
        115                 120                 125
```

```
Arg Pro Gly Phe Pro Ile Tyr Glu Leu Cys Ala Lys Phe Arg His Leu
    130                 135                 140

Glu Val Arg Tyr Val Asp Leu Leu Pro Glu Asn Gly Trp Glu Ile Asp
145                 150                 155                 160

Leu Asp Ala Val Glu Ala Leu Ala Asp Glu Asn Thr Val Ala Leu Val
                165                 170                 175

Val Ile Asn Pro Gly Asn Pro Cys Gly Asn Val Tyr Ser Tyr Gln His
            180                 185                 190

Leu Met Lys Ile Ala Glu Ser Ala Lys Lys Leu Gly Phe Leu Val Ile
        195                 200                 205

Ala Asp Glu Val Tyr Gly His Leu Ala Phe Gly Ser Lys Pro Phe Val
    210                 215                 220

Pro Met Gly Val Phe Gly Ser Ile Val Pro Val Leu Thr Leu Gly Ser
225                 230                 235                 240

Leu Ser Lys Arg Trp Ile Val Pro Gly Trp Arg Leu Gly Trp Phe Val
                245                 250                 255

Thr Thr Asp Pro Ser Gly Ser Phe Lys Asp Pro Lys Ile Ile Glu Arg
            260                 265                 270

Phe Lys Lys Tyr Phe Asp Ile Leu Gly Gly Pro Ala Thr Phe Ile Gln
        275                 280                 285

Ala Ala Val Pro Thr Ile Leu Glu Gln Thr Asp Glu Ser Phe Phe Lys
    290                 295                 300

Lys Thr Leu Asn Ser Leu Lys Asn Ser Ser Asp Ile Cys Cys Asp Trp
305                 310                 315                 320

Ile Lys Glu Ile Pro Cys Ile Asp Ser Ser His Arg Pro Glu Gly Ser
                325                 330                 335

Met Ala Met Met Val Lys Leu Asn Leu Ser Leu Leu Glu Asp Val Ser
            340                 345                 350

Asp Asp Ile Asp Phe Cys Phe Lys Leu Ala Arg Glu Glu Ser Val Ile
        355                 360                 365

Leu Leu Pro Gly Thr Ala Val Gly Leu Lys Asn Trp Leu Arg Ile Thr
    370                 375                 380

Phe Ala Ala Asp Ala Thr Ser Ile Glu Glu Ala Phe Lys Arg Ile Lys
385                 390                 395                 400

Cys Phe Tyr Leu Arg His Ala Lys Thr Gln Tyr Pro Thr Ile
                405                 410
```

<210> SEQ ID NO 5
<211> LENGTH: 459
<212> TYPE: DNA
<213> ORGANISM: Arabidopsis thaliana

<400> SEQUENCE: 5

```
atggctgaaa aagtaaagtc tggtcaagtt tttaacctat tatgcatatt ctcgatcttt      60

ttcttcctct ttgtgttatc agtgaatgtt tcggctgatg tcgattctga gagagcggtg     120

ccatctgaag ataaaacgac gactgtttgg ctaactaaaa tcaaacggtc cggtaaaaat     180

tattgggcta aagttagaga gactttggat cgtggacagt cccacttctt tcctccgaac     240

acatatttta ccggaaagaa tgatgcgccg atgggagccg gtgaaaatat gaaagaggcg     300

gcgacgagga gctttgagca tagcaaagcg acggtggagg aagctgctag atcagcggca     360

gaagtggtga gtgatacggc ggaagctgtg aaagaaaagg tgaagaggag cgtttccggt     420

ggagtgacgc agccgtcgga gggatctgag gagctataa                            459
```

<210> SEQ ID NO 6

<211> LENGTH: 152
<212> TYPE: PRT
<213> ORGANISM: Arabidopsis thaliana

<400> SEQUENCE: 6

```
Met Ala Glu Lys Val Lys Ser Gly Gln Val Phe Asn Leu Leu Cys Ile
1               5                   10                  15

Phe Ser Ile Phe Phe Phe Leu Phe Val Leu Ser Val Asn Val Ser Ala
            20                  25                  30

Asp Val Asp Ser Glu Arg Ala Val Pro Ser Glu Asp Lys Thr Thr Thr
        35                  40                  45

Val Trp Leu Thr Lys Ile Lys Arg Ser Gly Lys Asn Tyr Trp Ala Lys
    50                  55                  60

Val Arg Glu Thr Leu Asp Arg Gly Gln Ser His Phe Phe Pro Pro Asn
65                  70                  75                  80

Thr Tyr Phe Thr Gly Lys Asn Asp Ala Pro Met Gly Ala Gly Glu Asn
                85                  90                  95

Met Lys Glu Ala Ala Thr Arg Ser Phe Glu His Ser Lys Ala Thr Val
            100                 105                 110

Glu Glu Ala Ala Arg Ser Ala Ala Glu Val Val Ser Asp Thr Ala Glu
        115                 120                 125

Ala Val Lys Glu Lys Val Lys Arg Ser Val Ser Gly Gly Val Thr Gln
    130                 135                 140

Pro Ser Glu Gly Ser Glu Glu Leu
145                 150
```

<210> SEQ ID NO 7
<211> LENGTH: 1158
<212> TYPE: DNA
<213> ORGANISM: Arabidopsis thaliana

<400> SEQUENCE: 7

```
atggctggag aagaaataga gagggagaag aaatctgcag catctgcaag aactcacacc     60

agaaacaaca ctcaacaaag ttcttcttct ggttatctga aaacgcttct cctggtaacg    120

ttcgtcggag ttttagcatg ggtttatcaa acaatccaac caccacccgc caaaatcgtc    180

ggctctcccg gtggacccac cgtgacatca ccgaggatca aactgagaga cggaagacat    240

ctggcttaca cagaattcgg aatccctaga gacgaagcca agttcaagat cataaacatc    300

cacggcttcg attcttgtat gcgagactcg catttcgcca atttcttatc gccggctctt    360

gtggaggaat tgaggatata cattgtgtct tttgatcgtc ctggttatgg agagagtgat    420

cctaacctga atgggtcacc aagaagcata gcattggata tagaagagct tgctgatggg    480

ttaggactag gacctcagtt ctatctcttt ggttactcca tgggtggtga aattacatgg    540

gcatgcctta actacattcc tcacaggtta gcaggagctg cccttgtagc tccagcgatt    600

aactattggt ggagaaactt accgggagat ttaacaagag aagctttctc tcttatgcat    660

cctgcagatc aatggtcact tcgagtagct cattatgctc cttggcttac atattggtgg    720

aacactcaga aatggttccc aatctccaat gtgattgccg gtaatcccat tattttctca    780

cgtcaggaca tggagatctt gtcgaagctc ggattcgtca atccaaatcg ggcatacata    840

agacaacaag gtgaatatgt aagcttacac cgagatttga atgtcgcatt ttcaagctgg    900

gagtttgatc cgttagacct tcaagatccg ttcccgaaca acaatggctc agttcacgta    960

tggaatggcg atgaggataa gtttgtgcca gtaaagcttc aacggtatgt cgcgtcaaag   1020

ctgccatgga ttcgttacca tgaaatatct ggatcaggac attttgtacc atttgtggaa   1080
```

```
ggtatgactg ataagatcat caagtcactt ttggttgggg aagaagatgt aagtgagagt   1140

agagaagcct ctgtttaa                                                 1158


<210> SEQ ID NO 8
<211> LENGTH: 385
<212> TYPE: PRT
<213> ORGANISM: Arabidopsis thaliana

<400> SEQUENCE: 8

Met Ala Gly Glu Glu Ile Glu Arg Glu Lys Lys Ser Ala Ala Ser Ala
1               5                   10                  15

Arg Thr His Thr Arg Asn Asn Thr Gln Gln Ser Ser Ser Ser Gly Tyr
            20                  25                  30

Leu Lys Thr Leu Leu Leu Val Thr Phe Val Gly Val Leu Ala Trp Val
        35                  40                  45

Tyr Gln Thr Ile Gln Pro Pro Pro Ala Lys Ile Val Gly Ser Pro Gly
    50                  55                  60

Gly Pro Thr Val Thr Ser Pro Arg Ile Lys Leu Arg Asp Gly Arg His
65                  70                  75                  80

Leu Ala Tyr Thr Glu Phe Gly Ile Pro Arg Asp Glu Ala Lys Phe Lys
                85                  90                  95

Ile Ile Asn Ile His Gly Phe Asp Ser Cys Met Arg Asp Ser His Phe
            100                 105                 110

Ala Asn Phe Leu Ser Pro Ala Leu Val Glu Glu Leu Arg Ile Tyr Ile
        115                 120                 125

Val Ser Phe Asp Arg Pro Gly Tyr Gly Glu Ser Asp Pro Asn Leu Asn
    130                 135                 140

Gly Ser Pro Arg Ser Ile Ala Leu Asp Ile Glu Glu Leu Ala Asp Gly
145                 150                 155                 160

Leu Gly Leu Gly Pro Gln Phe Tyr Leu Phe Gly Tyr Ser Met Gly Gly
                165                 170                 175

Glu Ile Thr Trp Ala Cys Leu Asn Tyr Ile Pro His Arg Leu Ala Gly
            180                 185                 190

Ala Ala Leu Val Ala Pro Ala Ile Asn Tyr Trp Trp Arg Asn Leu Pro
        195                 200                 205

Gly Asp Leu Thr Arg Glu Ala Phe Ser Leu Met His Pro Ala Asp Gln
    210                 215                 220

Trp Ser Leu Arg Val Ala His Tyr Ala Pro Trp Leu Thr Tyr Trp Trp
225                 230                 235                 240

Asn Thr Gln Lys Trp Phe Pro Ile Ser Asn Val Ile Ala Gly Asn Pro
                245                 250                 255

Ile Ile Phe Ser Arg Gln Asp Met Glu Ile Leu Ser Lys Leu Gly Phe
            260                 265                 270

Val Asn Pro Asn Arg Ala Tyr Ile Arg Gln Gln Gly Glu Tyr Val Ser
        275                 280                 285

Leu His Arg Asp Leu Asn Val Ala Phe Ser Ser Trp Glu Phe Asp Pro
    290                 295                 300

Leu Asp Leu Gln Asp Pro Phe Pro Asn Asn Asn Gly Ser Val His Val
305                 310                 315                 320

Trp Asn Gly Asp Glu Asp Lys Phe Val Pro Val Lys Leu Gln Arg Tyr
                325                 330                 335

Val Ala Ser Lys Leu Pro Trp Ile Arg Tyr His Glu Ile Ser Gly Ser
            340                 345                 350

Gly His Phe Val Pro Phe Val Glu Gly Met Thr Asp Lys Ile Ile Lys
        355                 360                 365
```

```
Ser Leu Leu Val Gly Glu Glu Asp Val Ser Glu Ser Arg Glu Ala Ser
    370                 375                 380

Val
385


<210> SEQ ID NO 9
<211> LENGTH: 357
<212> TYPE: DNA
<213> ORGANISM: Arabidopsis thaliana

<400> SEQUENCE: 9

atggctggag tgatgaagtt ggcatgcatg gtcttggctt gcatgattgt ggccggtcca      60

atcacagcga acgcgcttat gagttgtggc accgtcaacg gcaacctggc agggtgcatt     120

gcctacttga cccgaggtgc tccacttacc caagggtgct gcaacggcgt tactaacctt     180

aaaaacatgg ccagtacaac cccagaccgt cagcaagctt gccgttgcct tcaatctgcc     240

gctaaagccg ttggtcccgg tctcaacact gcccgtgcag ctggacttcc tagcgcatgc     300

aaagtcaata ttccttacaa aatcagcgcc agcaccaact gcaacaccgt gaggtga        357


<210> SEQ ID NO 10
<211> LENGTH: 118
<212> TYPE: PRT
<213> ORGANISM: Arabidopsis thaliana

<400> SEQUENCE: 10

Met Ala Gly Val Met Lys Leu Ala Cys Met Val Leu Ala Cys Met Ile
1               5                   10                  15

Val Ala Gly Pro Ile Thr Ala Asn Ala Leu Met Ser Cys Gly Thr Val
            20                  25                  30

Asn Gly Asn Leu Ala Gly Cys Ile Ala Tyr Leu Thr Arg Gly Ala Pro
        35                  40                  45

Leu Thr Gln Gly Cys Cys Asn Gly Val Thr Asn Leu Lys Asn Met Ala
    50                  55                  60

Ser Thr Thr Pro Asp Arg Gln Gln Ala Cys Arg Cys Leu Gln Ser Ala
65                  70                  75                  80

Ala Lys Ala Val Gly Pro Gly Leu Asn Thr Ala Arg Ala Ala Gly Leu
                85                  90                  95

Pro Ser Ala Cys Lys Val Asn Ile Pro Tyr Lys Ile Ser Ala Ser Thr
            100                 105                 110

Asn Cys Asn Thr Val Arg
        115


<210> SEQ ID NO 11
<211> LENGTH: 1332
<212> TYPE: DNA
<213> ORGANISM: Arabidopsis thaliana

<400> SEQUENCE: 11

atggggcttg ctgtggtgga caaaaacaca gttgcgattt ctgcatctga tgttatgttg      60

tcctttgctg cttttccagt cgagattcct ggagaggtag tatttcttca tcccgttcac     120

aactatgctc tgattgcgta taatccatca gcaatggatc ctgccagtgc ttcagtcatt     180

cgtgcagctg agctactacc tgaacctgca ctccaacgtg gagattcagt ctatcttgtc     240

ggattgagta ggaaccttca agctacatca agaaaatcta ttgtaaccaa tccatgtgca     300

gcgttaaaca ttggttctgc tgattctccc cgttacagag ctactaatat ggaagtaatt     360

gagcttgata cagattttgg tagctcattt tcaggggcgc tgactgatga gcagggaaga     420
```

```
attcgggcta tttggggaag tttttcgact caggttaaat atagttccac ttcttcagaa    480

gaccaccagt ttgtcagagg tatcccagta tatgcaatca gccaagtcct tgaaaaaatc    540

ataaccggtg gaaatggacc agctcttctc ataaatggtg tcaaaaggcc aatgccactt    600

gttcggattt tggaagttga attgtatcct actttgcttt caaaagcccg gagttttggt    660

ctgagtgatg aatggatcca agtcctagtc aagaaggatc ctgttagacg tcaagttctg    720

cgtgttaaag gttgcctggc aggatcaaaa gctgaaaacc ttcttgaaca aggcgatatg    780

gttctggcag tcaataagat gccagttaca tgcttcaatg acatagaagc tgcttgccaa    840

acattggata agggtagtta cagcgatgaa aatctcaatc taacaatcct tagacagggc    900

caagaactgg agctcgtagt tggaactgat aagagagatg ggaatggaac gacaagagtg    960

ataaattggt gcggatgcgt tgttcaggat cctcatcctg cggttcgtgc tcttggattt   1020

cttcctgagg aaggtcatgg tgtctatgtc acaagatggt gtcacgggag tcccgctcac   1080

cgatatggcc tctacgcgct tcaatggatc gtggaagtta atgggaagaa gactcctgac   1140

ctaaacgcat tcgcagatgc taccaaggag ctagaacacg ggcagtttgt gcgtattagg   1200

actgttcatc taaacggcaa gccacgagta ttgaccctga aacaagatct ccattactgg   1260

ccgacttggg aattgaggtt cgacccagag actgctcttt ggcggagaaa tatattgaaa   1320

gccttgcagt aa                                                        1332
```

<210> SEQ ID NO 12
<211> LENGTH: 443
<212> TYPE: PRT
<213> ORGANISM: Arabidopsis thaliana

<400> SEQUENCE: 12

```
Met Gly Leu Ala Val Val Asp Lys Asn Thr Val Ala Ile Ser Ala Ser
1               5                   10                  15

Asp Val Met Leu Ser Phe Ala Ala Phe Pro Val Glu Ile Pro Gly Glu
            20                  25                  30

Val Val Phe Leu His Pro Val His Asn Tyr Ala Leu Ile Ala Tyr Asn
        35                  40                  45

Pro Ser Ala Met Asp Pro Ala Ser Ala Ser Val Ile Arg Ala Ala Glu
    50                  55                  60

Leu Leu Pro Glu Pro Ala Leu Gln Arg Gly Asp Ser Val Tyr Leu Val
65                  70                  75                  80

Gly Leu Ser Arg Asn Leu Gln Ala Thr Ser Arg Lys Ser Ile Val Thr
                85                  90                  95

Asn Pro Cys Ala Ala Leu Asn Ile Gly Ser Ala Asp Ser Pro Arg Tyr
            100                 105                 110

Arg Ala Thr Asn Met Glu Val Ile Glu Leu Asp Thr Asp Phe Gly Ser
        115                 120                 125

Ser Phe Ser Gly Ala Leu Thr Asp Glu Gln Gly Arg Ile Arg Ala Ile
    130                 135                 140

Trp Gly Ser Phe Ser Thr Gln Val Lys Tyr Ser Ser Thr Ser Ser Glu
145                 150                 155                 160

Asp His Gln Phe Val Arg Gly Ile Pro Val Tyr Ala Ile Ser Gln Val
                165                 170                 175

Leu Glu Lys Ile Ile Thr Gly Gly Asn Gly Pro Ala Leu Leu Ile Asn
            180                 185                 190

Gly Val Lys Arg Pro Met Pro Leu Val Arg Ile Leu Glu Val Glu Leu
        195                 200                 205
```

```
Tyr Pro Thr Leu Leu Ser Lys Ala Arg Ser Phe Gly Leu Ser Asp Glu
    210                 215                 220

Trp Ile Gln Val Leu Val Lys Lys Asp Pro Val Arg Arg Gln Val Leu
225                 230                 235                 240

Arg Val Lys Gly Cys Leu Ala Gly Ser Lys Ala Glu Asn Leu Leu Glu
                245                 250                 255

Gln Gly Asp Met Val Leu Ala Val Asn Lys Met Pro Val Thr Cys Phe
            260                 265                 270

Asn Asp Ile Glu Ala Ala Cys Gln Thr Leu Asp Lys Gly Ser Tyr Ser
        275                 280                 285

Asp Glu Asn Leu Asn Leu Thr Ile Leu Arg Gln Gly Gln Glu Leu Glu
    290                 295                 300

Leu Val Val Gly Thr Asp Lys Arg Asp Gly Asn Gly Thr Thr Arg Val
305                 310                 315                 320

Ile Asn Trp Cys Gly Cys Val Val Gln Asp Pro His Pro Ala Val Arg
                325                 330                 335

Ala Leu Gly Phe Leu Pro Glu Glu Gly His Gly Val Tyr Val Thr Arg
            340                 345                 350

Trp Cys His Gly Ser Pro Ala His Arg Tyr Gly Leu Tyr Ala Leu Gln
        355                 360                 365

Trp Ile Val Glu Val Asn Gly Lys Lys Thr Pro Asp Leu Asn Ala Phe
    370                 375                 380

Ala Asp Ala Thr Lys Glu Leu Glu His Gly Gln Phe Val Arg Ile Arg
385                 390                 395                 400

Thr Val His Leu Asn Gly Lys Pro Arg Val Leu Thr Leu Lys Gln Asp
                405                 410                 415

Leu His Tyr Trp Pro Thr Trp Glu Leu Arg Phe Asp Pro Glu Thr Ala
            420                 425                 430

Leu Trp Arg Arg Asn Ile Leu Lys Ala Leu Gln
        435                 440
```

<210> SEQ ID NO 13
<211> LENGTH: 312
<212> TYPE: DNA
<213> ORGANISM: Arabidopsis thaliana

<400> SEQUENCE: 13

```
atggcgttca cggcgcttgt gttcattgtg ttcgtggtgg gtgtcatggt ttctccagtt      60

tcaatcagag caactgaggt caaactttct ggaggagaag ctgatgtaac gtgtgatgca     120

gtacagctta gttcatgcgc aacaccaatg ctcacaggag taccaccgtc tacagagtgt     180

tgcgggaaac tgaaggagca acagccgtgt ttttgtacat atattaaaga tccaagatat     240

agtcaatatg ttggttctgc aaatgctaag aaaacgttag caacttgtgg tgttccttat     300

cctacttgtt ga                                                         312
```

<210> SEQ ID NO 14
<211> LENGTH: 103
<212> TYPE: PRT
<213> ORGANISM: Arabidopsis thaliana

<400> SEQUENCE: 14

```
Met Ala Phe Thr Ala Leu Val Phe Ile Val Phe Val Val Gly Val Met
1               5                   10                  15

Val Ser Pro Val Ser Ile Arg Ala Thr Glu Val Lys Leu Ser Gly Gly
            20                  25                  30

Glu Ala Asp Val Thr Cys Asp Ala Val Gln Leu Ser Ser Cys Ala Thr
```

```
        35                  40                  45

Pro Met Leu Thr Gly Val Pro Pro Ser Thr Glu Cys Cys Gly Lys Leu
    50                  55                  60

Lys Glu Gln Gln Pro Cys Phe Cys Thr Tyr Ile Lys Asp Pro Arg Tyr
65                  70                  75                  80

Ser Gln Tyr Val Gly Ser Ala Asn Ala Lys Lys Thr Leu Ala Thr Cys
                85                  90                  95

Gly Val Pro Tyr Pro Thr Cys
            100


<210> SEQ ID NO 15
<211> LENGTH: 660
<212> TYPE: DNA
<213> ORGANISM: Arabidopsis thaliana

<400> SEQUENCE: 15

atggcccttg atgagcttct caagactgtc ttgccaccag ctgaggaagg gcttgttcgt      60

cagggaagct tgacgttacc tcgagatctc agtaaaaaga cagttgatga ggtctggaga     120

gatatccaac aggacaagaa tggaaacggt actagtacta ctactactca taagcagcct     180

acactcggtg aaataacact tgaggatttg ttgttgagag ctggtgtagt gactgagaca     240

gtagtccctc aagaaaatgt tgttaacata gcttcaaatg ggcaatgggt tgagtatcat     300

catcagcctc aacaacaaca agggtttatg acatatccgg tttgcgagat gcaagatatg     360

gtgatgatgg gtggattatc ggatacacca caagcgcctg ggaggaaaag agtagctgga     420

gagattgtgg agaagactgt tgagaggaga cagaagagga tgatcaagaa cagagaatct     480

gcagcacgtt cacgagctag gaaacaggct tatacacatg aattagagat caaggtttca     540

aggttagaag aagaaaacga aaaacttcgg aggctaaagg aggtggagaa gatcctacca     600

agtgaaccac caccagatcc taagtggaag ctccggcgaa caaactctgc ttctctctga     660


<210> SEQ ID NO 16
<211> LENGTH: 219
<212> TYPE: PRT
<213> ORGANISM: Arabidopsis thaliana

<400> SEQUENCE: 16

Met Ala Leu Asp Glu Leu Leu Lys Thr Val Leu Pro Pro Ala Glu Glu
1               5                   10                  15

Gly Leu Val Arg Gln Gly Ser Leu Thr Leu Pro Arg Asp Leu Ser Lys
            20                  25                  30

Lys Thr Val Asp Glu Val Trp Arg Asp Ile Gln Gln Asp Lys Asn Gly
        35                  40                  45

Asn Gly Thr Ser Thr Thr Thr Thr His Lys Gln Pro Thr Leu Gly Glu
    50                  55                  60

Ile Thr Leu Glu Asp Leu Leu Leu Arg Ala Gly Val Val Thr Glu Thr
65                  70                  75                  80

Val Val Pro Gln Glu Asn Val Val Asn Ile Ala Ser Asn Gly Gln Trp
                85                  90                  95

Val Glu Tyr His His Gln Pro Gln Gln Gln Gln Gly Phe Met Thr Tyr
            100                 105                 110

Pro Val Cys Glu Met Gln Asp Met Val Met Met Gly Gly Leu Ser Asp
        115                 120                 125

Thr Pro Gln Ala Pro Gly Arg Lys Arg Val Ala Gly Glu Ile Val Glu
    130                 135                 140

Lys Thr Val Glu Arg Arg Gln Lys Arg Met Ile Lys Asn Arg Glu Ser
```

```
145                 150                 155                 160

Ala Ala Arg Ser Arg Ala Arg Lys Gln Ala Tyr Thr His Glu Leu Glu
                165                 170                 175

Ile Lys Val Ser Arg Leu Glu Glu Glu Asn Glu Lys Leu Arg Arg Leu
            180                 185                 190

Lys Glu Val Glu Lys Ile Leu Pro Ser Glu Pro Pro Pro Asp Pro Lys
        195                 200                 205

Trp Lys Leu Arg Arg Thr Asn Ser Ala Ser Leu
    210                 215


<210> SEQ ID NO 17
<211> LENGTH: 741
<212> TYPE: DNA
<213> ORGANISM: Arabidopsis thaliana

<400> SEQUENCE: 17

atggcgcaat cccgattatt agcgtttgct tcagcggcgc gttcacgtgt tcgaccaatc      60

gctcaaaggc gtttagcgtt tggatcatcc acgtctggtc gcacagctga tccagagatc     120

catgccggta acgatggagc cgatccagct atctatccga gagaccctga aggtatggat     180

gatgttgcaa accctaaaac ggcggcggaa gaaatcgtag acgatactcc ccgaccgagt     240

ttagaagagc aaccgcttgt accgccgaaa tctccacgcg ccactgcgca caagctagag     300

agtactcccg ttggtcaccc gtcagaacct catttccaac agaaacgaaa aaactccacc     360

gcttctccgc cgtcgcttga ttccgtgagc tgtgctggtt tagacggttc accatggccg     420

agagacgaag gagaagtgga agagcaaagg cgaagagaag atgaaacaga gagtgaccaa     480

gagttttaca aacaccacaa agcttctccg ttatcggaga ttgaattcgc cgatactcgg     540

aaacctatta cgcaagctac cgatggaact gcctacccag ccgggaaaga tgtgatcgga     600

tggttaccgg agcagctaga cacggcggaa gaatctttga tgaaagcaac aatgatattc     660

aaacgcaacg cagaacgtgg cgatcctgaa acgtttcctc attctagaat cttaagagaa     720

atgagaggcg agtggtttta a                                               741


<210> SEQ ID NO 18
<211> LENGTH: 246
<212> TYPE: PRT
<213> ORGANISM: Arabidopsis thaliana

<400> SEQUENCE: 18

Met Ala Gln Ser Arg Leu Leu Ala Phe Ala Ser Ala Ala Arg Ser Arg
1               5                   10                  15

Val Arg Pro Ile Ala Gln Arg Arg Leu Ala Phe Gly Ser Ser Thr Ser
            20                  25                  30

Gly Arg Thr Ala Asp Pro Glu Ile His Ala Gly Asn Asp Gly Ala Asp
        35                  40                  45

Pro Ala Ile Tyr Pro Arg Asp Pro Glu Gly Met Asp Asp Val Ala Asn
    50                  55                  60

Pro Lys Thr Ala Ala Glu Glu Ile Val Asp Asp Thr Pro Arg Pro Ser
65                  70                  75                  80

Leu Glu Glu Gln Pro Leu Val Pro Pro Lys Ser Pro Arg Ala Thr Ala
                85                  90                  95

His Lys Leu Glu Ser Thr Pro Val Gly His Pro Ser Glu Pro His Phe
            100                 105                 110

Gln Gln Lys Arg Lys Asn Ser Thr Ala Ser Pro Pro Ser Leu Asp Ser
        115                 120                 125
```

```
Val Ser Cys Ala Gly Leu Asp Gly Ser Pro Trp Pro Arg Asp Glu Gly
    130                 135                 140

Glu Val Glu Glu Gln Arg Arg Arg Glu Asp Glu Thr Glu Ser Asp Gln
145                 150                 155                 160

Glu Phe Tyr Lys His His Lys Ala Ser Pro Leu Ser Glu Ile Glu Phe
                165                 170                 175

Ala Asp Thr Arg Lys Pro Ile Thr Gln Ala Thr Asp Gly Thr Ala Tyr
            180                 185                 190

Pro Ala Gly Lys Asp Val Ile Gly Trp Leu Pro Glu Gln Leu Asp Thr
        195                 200                 205

Ala Glu Glu Ser Leu Met Lys Ala Thr Met Ile Phe Lys Arg Asn Ala
    210                 215                 220

Glu Arg Gly Asp Pro Glu Thr Phe Pro His Ser Arg Ile Leu Arg Glu
225                 230                 235                 240

Met Arg Gly Glu Trp Phe
                245
```

<210> SEQ ID NO 19
<211> LENGTH: 1425
<212> TYPE: DNA
<213> ORGANISM: Arabidopsis thaliana

<400> SEQUENCE: 19

```
atgtccgtgg ctcgattcga tttctcttgg tgcgatgctg attatcacca ggagacgctg     60

gagaatctga agatagctgt gaagagcact aagaagcttt gtgctgttat gctagacact    120

gtaggacctg agttgcaagt tattaacaag actgagaaag ctatttctct taaagctgat    180

ggccttgtaa ctttgactcc gagtcaagat caagaagcct cctctgaagt ccttcccatt    240

aattttgatg ggttagcgaa ggcggttaag aaaggagaca ctatctttgt tggacaatac    300

ctcttcactg gtagtgaaac aacttcagtt tggcttgagg ttgaagaagt taaaggagat    360

gatgtcattt gtatttcaag gaatgctgct actctgggtg gtccgttatt cacattgcac    420

gtctctcaag ttcacattga tatgccaacc ctaactgaga aggataagga ggttataagt    480

acatggggag ttcagaataa gatcgacttt ctctcattat cttattgtcg acatgcagaa    540

gatgttcgcc aggcccgtga gttgcttaac agttgtggtg acctctctca aacacaaata    600

tttgcgaaga ttgagaatga agagggacta acccactttg acgaaattct acaagaagca    660

gatggcatta ttctttctcg tgggaatttg ggtatcgatc tacctccgga aaaggtgttt    720

ttgttccaaa aggctgctct ttacaagtgt aacatggctg gaaagcctgc cgttcttact    780

cgtgttgtag acagtatgac agacaatctg cggccaactc gtgcagaggc aactgatgtt    840

gctaatgctg ttttagatgg aagtgatgca attcttcttg gtgctgagac tcttcgtgga    900

ttgtaccctg ttgaaaccat atcaactgtt ggtagaatct gttgtgaggc agagaaagtt    960

ttcaaccaag atttgttctt taagaagact gtcaagtatg ttggagaacc aatgactcac   1020

ttggaatcta ttgcttcttc tgctgtacgg gcagcaatca aggttaaggc atccgtaatt   1080

atatgcttca cctcgtctgg cagagcagca aggttgattg ccaaataccg tccaactatg   1140

cccgttctct ctgttgtcat tccccgactt acgacaaatc agctgaagtg gagctttagc   1200

ggagcctttg aggcaaggca gtcacttatt gtcagaggtc ttttccccat gcttgctgat   1260

cctcgtcacc ctgcggaatc aacaagtgca acaaatgagt cggttcttaa agtggctcta   1320

gaccatggga agcaagccgg agtgatcaag tcacatgaca gagttgtggt ctgtcagaaa   1380

gtgggagatg cgtccgtggt caaaatcatc gagctagagg attag                   1425
```

<210> SEQ ID NO 20
<211> LENGTH: 474
<212> TYPE: PRT
<213> ORGANISM: Arabidopsis thaliana

<400> SEQUENCE: 20

```
Met Ser Val Ala Arg Phe Asp Phe Ser Trp Cys Asp Ala Asp Tyr His
1               5                   10                  15

Gln Glu Thr Leu Glu Asn Leu Lys Ile Ala Val Lys Ser Thr Lys Lys
            20                  25                  30

Leu Cys Ala Val Met Leu Asp Thr Val Gly Pro Glu Leu Gln Val Ile
        35                  40                  45

Asn Lys Thr Glu Lys Ala Ile Ser Leu Lys Ala Asp Gly Leu Val Thr
    50                  55                  60

Leu Thr Pro Ser Gln Asp Gln Glu Ala Ser Ser Glu Val Leu Pro Ile
65                  70                  75                  80

Asn Phe Asp Gly Leu Ala Lys Ala Val Lys Lys Gly Asp Thr Ile Phe
                85                  90                  95

Val Gly Gln Tyr Leu Phe Thr Gly Ser Glu Thr Thr Ser Val Trp Leu
            100                 105                 110

Glu Val Glu Glu Val Lys Gly Asp Asp Val Ile Cys Ile Ser Arg Asn
        115                 120                 125

Ala Ala Thr Leu Gly Gly Pro Leu Phe Thr Leu His Val Ser Gln Val
    130                 135                 140

His Ile Asp Met Pro Thr Leu Thr Glu Lys Asp Lys Glu Val Ile Ser
145                 150                 155                 160

Thr Trp Gly Val Gln Asn Lys Ile Asp Phe Leu Ser Leu Ser Tyr Cys
                165                 170                 175

Arg His Ala Glu Asp Val Arg Gln Ala Arg Glu Leu Leu Asn Ser Cys
            180                 185                 190

Gly Asp Leu Ser Gln Thr Gln Ile Phe Ala Lys Ile Glu Asn Glu Glu
        195                 200                 205

Gly Leu Thr His Phe Asp Glu Ile Leu Gln Glu Ala Asp Gly Ile Ile
    210                 215                 220

Leu Ser Arg Gly Asn Leu Gly Ile Asp Leu Pro Pro Glu Lys Val Phe
225                 230                 235                 240

Leu Phe Gln Lys Ala Ala Leu Tyr Lys Cys Asn Met Ala Gly Lys Pro
                245                 250                 255

Ala Val Leu Thr Arg Val Val Asp Ser Met Thr Asp Asn Leu Arg Pro
            260                 265                 270

Thr Arg Ala Glu Ala Thr Asp Val Ala Asn Ala Val Leu Asp Gly Ser
        275                 280                 285

Asp Ala Ile Leu Leu Gly Ala Glu Thr Leu Arg Gly Leu Tyr Pro Val
    290                 295                 300

Glu Thr Ile Ser Thr Val Gly Arg Ile Cys Cys Glu Ala Glu Lys Val
305                 310                 315                 320

Phe Asn Gln Asp Leu Phe Phe Lys Lys Thr Val Lys Tyr Val Gly Glu
                325                 330                 335

Pro Met Thr His Leu Glu Ser Ile Ala Ser Ser Ala Val Arg Ala Ala
            340                 345                 350

Ile Lys Val Lys Ala Ser Val Ile Ile Cys Phe Thr Ser Ser Gly Arg
        355                 360                 365

Ala Ala Arg Leu Ile Ala Lys Tyr Arg Pro Thr Met Pro Val Leu Ser
    370                 375                 380
```

```
Val Val Ile Pro Arg Leu Thr Thr Asn Gln Leu Lys Trp Ser Phe Ser
385                 390                 395                 400

Gly Ala Phe Glu Ala Arg Gln Ser Leu Ile Val Arg Gly Leu Phe Pro
                405                 410                 415

Met Leu Ala Asp Pro Arg His Pro Ala Glu Ser Thr Ser Ala Thr Asn
            420                 425                 430

Glu Ser Val Leu Lys Val Ala Leu Asp His Gly Lys Gln Ala Gly Val
        435                 440                 445

Ile Lys Ser His Asp Arg Val Val Val Cys Gln Lys Val Gly Asp Ala
    450                 455                 460

Ser Val Val Lys Ile Ile Glu Leu Glu Asp
465                 470
```

<210> SEQ ID NO 21
<211> LENGTH: 936
<212> TYPE: DNA
<213> ORGANISM: Arabidopsis thaliana

<400> SEQUENCE: 21

```
atggcgattt acagatctct aagaaagcta gttgaaatca atcaccggaa aacaagacca      60

ttcctcaccg ccgctacagc ttccggcgga accgtttctc tgactccacc gcagttttcg     120

ccgttgttcc cacatttctc acaccgttta tctccgcttt cgaaatggtt cgttcctctt     180

aatggacctc tcttcttatc ttctcctcct tggaaacttc tccagtctgc gacacctttg     240

cactggcgcg gaaacggctc tgttttgaaa aaagtcgaag ctctgaatct tagattggat     300

cgaattagaa gcagaactag gtttccgaga cagttagggt tacagtctgt ggtaccaaac     360

atattgacgg tggatcgcaa cgattccaag gaagaagatg gtggaaaatt agtcaagagt     420

tttgttaatg tgccgaatat gatatcaatg gcgagattag tatctggtcc tgtgctttgg     480

tggatgatct cgaatgagat gtattcttct gctttcttag ggttggctgt ttctggagct     540

agtgattggt tagatggtta cgtggctcgg aggatgaaga ttaactctgt ggttggctcg     600

taccttgatc ctcttgcaga caaggttctt atcgggtgtg tagcagtagc aatggtgcag     660

aaggatctct tacatcctgg actggttgga attgtgttgt tacgggatgt tgcactcgtt     720

ggtggtgcag tttacctaag ggcactaaac ttggactgga ggtggaaaac ttggagtgac     780

ttcttcaatc tagatggttc aagtcctcag aaagtagaac cattgtttat aagcaaggtg     840

aatacagttt tccagttgac tctagtcgct ggtgcaatac ttcaaccaga gtttgggaat     900

ccagacaccc agacatggat cacttatcta aggtaa                               936
```

<210> SEQ ID NO 22
<211> LENGTH: 311
<212> TYPE: PRT
<213> ORGANISM: Arabidopsis thaliana

<400> SEQUENCE: 22

```
Met Ala Ile Tyr Arg Ser Leu Arg Lys Leu Val Glu Ile Asn His Arg
1               5                   10                  15

Lys Thr Arg Pro Phe Leu Thr Ala Ala Thr Ala Ser Gly Gly Thr Val
            20                  25                  30

Ser Leu Thr Pro Pro Gln Phe Ser Pro Leu Phe Pro His Phe Ser His
        35                  40                  45

Arg Leu Ser Pro Leu Ser Lys Trp Phe Val Pro Leu Asn Gly Pro Leu
    50                  55                  60

Phe Leu Ser Ser Pro Pro Trp Lys Leu Leu Gln Ser Ala Thr Pro Leu
65                  70                  75                  80
```

His Trp Arg Gly Asn Gly Ser Val Leu Lys Lys Val Glu Ala Leu Asn
85 90 95

Leu Arg Leu Asp Arg Ile Arg Ser Arg Thr Arg Phe Pro Arg Gln Leu
100 105 110

Gly Leu Gln Ser Val Val Pro Asn Ile Leu Thr Val Asp Arg Asn Asp
115 120 125

Ser Lys Glu Glu Asp Gly Gly Lys Leu Val Lys Ser Phe Val Asn Val
130 135 140

Pro Asn Met Ile Ser Met Ala Arg Leu Val Ser Gly Pro Val Leu Trp
145 150 155 160

Trp Met Ile Ser Asn Glu Met Tyr Ser Ser Ala Phe Leu Gly Leu Ala
165 170 175

Val Ser Gly Ala Ser Asp Trp Leu Asp Gly Tyr Val Ala Arg Arg Met
180 185 190

Lys Ile Asn Ser Val Val Gly Ser Tyr Leu Asp Pro Leu Ala Asp Lys
195 200 205

Val Leu Ile Gly Cys Val Ala Val Ala Met Val Gln Lys Asp Leu Leu
210 215 220

His Pro Gly Leu Val Gly Ile Val Leu Leu Arg Asp Val Ala Leu Val
225 230 235 240

Gly Gly Ala Val Tyr Leu Arg Ala Leu Asn Leu Asp Trp Arg Trp Lys
245 250 255

Thr Trp Ser Asp Phe Phe Asn Leu Asp Gly Ser Ser Pro Gln Lys Val
260 265 270

Glu Pro Leu Phe Ile Ser Lys Val Asn Thr Val Phe Gln Leu Thr Leu
275 280 285

Val Ala Gly Ala Ile Leu Gln Pro Glu Phe Gly Asn Pro Asp Thr Gln
290 295 300

Thr Trp Ile Thr Tyr Leu Arg
305 310

<210> SEQ ID NO 23
<211> LENGTH: 2427
<212> TYPE: DNA
<213> ORGANISM: Arabidopsis thaliana

<400> SEQUENCE: 23
atggtaaagg aaactctaat tcctccgtca tctacgtcaa tgacgaccgg aacatcttct 60
tcttcgtctc tttcaatgac gttatcctca acaaacgcgt tatcgttttt gtcgaaagga 120
tggagagagg tatgggattc agcagatgcg gatttgcagc tgatgcgaga cagagctaac 180
tctgttaaga atctagcatc aacgttcgat agagagatcg agaatttcct caataactcg 240
gcgaggtctg cgtttcccgt tggttcacca tcggcgtcgt ctttctcaaa tgaaattggt 300
atcatgaaga agcttcagcc gaagatttcg gagtttcgta gggtttattc ggcgccggag 360
attagtcgca aggttatgga gagatgggga cctgcgagag cgaagcttgg aatggatcta 420
tcggcgatta agaaggcgat tgtgtctgag atggaattgg atgagcgtca gggagttttg 480
gagatgagta gattgaggag acggcgtaat agtgataggg ttaggtttac ggagtttttc 540
gcggaggctg agagagatgg agaagcttat ttcggtgatt gggaaccgat taggtctttg 600
aagagtagat ttaaagagtt tgagaaacga agctcgttag aaatattgag tggattcaag 660
aacagtgaat ttgttgagaa gctcaaaacc agctttaaat caatttacaa agaaactgat 720
gaggctaagg atgtccctcc gttggatgta cctgaactgt tggcatgttt ggttagacaa 780

-continued

```
tctgaacctt ttcttgatca gattggtgtt agaaaggata catgtgaccg aatagtagaa    840
agcctttgca aatgcaagag ccaacaactt tggcgtctgc catctgcaca agcatccgat    900
ttaattgaaa atgataacca tggagttgat ttggatatga ggatagccag tgttcttcaa    960
agcacaggac accattatga tggtgggttt tggactgatt ttgtgaagcc tgagacaccg   1020
gaaaacaaaa ggcatgtggc aattgttaca acagctagtc ttccttggat gaccggaaca   1080
gctgtaaatc cgctattcag agcggcgtat ttggcaaaag ctgcaaaaca gagtgttact   1140
ctcgtggttc cttggctctg cgaatctgat caagaactag tgtatccaaa caatctcacc   1200
ttcagctcac ctgaagaaca agagagttat atacgtaaat ggttggagga aaggattggt   1260
ttcaaggctg attttaaaat ctccttttac ccaggaaagt tttcaaaaga aaggcgcagc   1320
atatttcctg ctggtgacac ttctcaattt atatcgtcaa aagatgctga cattgctata   1380
cttgaagaac ctgaacatct caactggtat tatcacggca agcgttggac tgataaattc   1440
aaccatgttg ttggaattgt ccacacaaac tacttagagt acatcaagag ggagaagaat   1500
ggagctcttc aagcattttt tgtgaaccat gtaaacaatt gggtcacacg agcgtattgt   1560
gacaaggttc ttcgcctctc tgcggcaaca caagatttac caaagtctgt tgtatgcaat   1620
gtccatggtg tcaatcccaa gttccttatg attggggaga aattgctgaa agagagatcc   1680
cgtggtgaac aagctttctc aaaaggtgca tacttcttag gaaaaatggt gtgggctaaa   1740
ggatacagag aactaataga tctgatggct aaacacaaaa gcgaacttgg gagcttcaat   1800
ctagatgtat atgggaacgg tgaagatgca gtcgaggtcc aacgtgcagc aaagaaacat   1860
gacttgaatc tcaatttcct caaaggaagg gaccacgctg acgatgctct tcacaagtac   1920
aaagtgttca taaaccccag catcagcgat gttctatgca cagcaaccgc agaagcacta   1980
gccatgggga agtttgtggt gtgtgcagat cacccttcaa acgaattctt tagatcattc   2040
ccgaactgct taacttacaa aacatccgaa gactttgtgt ccaaagtgca agaagcaatg   2100
acgaaagagc cactacctct cactcctgaa caaatgtaca atctctcttg ggaagcagca   2160
acacagaggt tcatggagta ttcagatctc gataagatct taaacaatgg agagggagga   2220
aggaagatgc gaaaatcaag atcggttccg agctttaacg aggtggtcga tggaggattg   2280
gcattctcac actatgttct aacagggaac gatttcttga gactatgcac tggagcaaca   2340
ccaagaacaa aagactatga taatcaacat tgcaaggatc tgaatctcgt accacctcac   2400
gttcacaagc caatcttcgg ctggtag                                       2427
```

<210> SEQ ID NO 24
<211> LENGTH: 808
<212> TYPE: PRT
<213> ORGANISM: Arabidopsis thaliana

<400> SEQUENCE: 24

```
Met Val Lys Glu Thr Leu Ile Pro Pro Ser Ser Thr Ser Met Thr Thr
1               5                   10                  15

Gly Thr Ser Ser Ser Ser Ser Leu Ser Met Thr Leu Ser Ser Thr Asn
            20                  25                  30

Ala Leu Ser Phe Leu Ser Lys Gly Trp Arg Glu Val Trp Asp Ser Ala
        35                  40                  45

Asp Ala Asp Leu Gln Leu Met Arg Asp Arg Ala Asn Ser Val Lys Asn
    50                  55                  60

Leu Ala Ser Thr Phe Asp Arg Glu Ile Glu Asn Phe Leu Asn Asn Ser
65                  70                  75                  80

Ala Arg Ser Ala Phe Pro Val Gly Ser Pro Ser Ala Ser Ser Phe Ser
```

```
                85                  90                  95

Asn Glu Ile Gly Ile Met Lys Lys Leu Gln Pro Lys Ile Ser Glu Phe
            100                 105                 110

Arg Arg Val Tyr Ser Ala Pro Glu Ile Ser Arg Lys Val Met Glu Arg
        115                 120                 125

Trp Gly Pro Ala Arg Ala Lys Leu Gly Met Asp Leu Ser Ala Ile Lys
    130                 135                 140

Lys Ala Ile Val Ser Glu Met Glu Leu Asp Glu Arg Gln Gly Val Leu
145                 150                 155                 160

Glu Met Ser Arg Leu Arg Arg Arg Arg Asn Ser Asp Arg Val Arg Phe
                165                 170                 175

Thr Glu Phe Phe Ala Glu Ala Glu Arg Asp Gly Glu Ala Tyr Phe Gly
            180                 185                 190

Asp Trp Glu Pro Ile Arg Ser Leu Lys Ser Arg Phe Lys Glu Phe Glu
        195                 200                 205

Lys Arg Ser Ser Leu Glu Ile Leu Ser Gly Phe Lys Asn Ser Glu Phe
    210                 215                 220

Val Glu Lys Leu Lys Thr Ser Phe Lys Ser Ile Tyr Lys Glu Thr Asp
225                 230                 235                 240

Glu Ala Lys Asp Val Pro Pro Leu Asp Val Pro Glu Leu Leu Ala Cys
                245                 250                 255

Leu Val Arg Gln Ser Glu Pro Phe Leu Asp Gln Ile Gly Val Arg Lys
            260                 265                 270

Asp Thr Cys Asp Arg Ile Val Glu Ser Leu Cys Lys Cys Lys Ser Gln
        275                 280                 285

Gln Leu Trp Arg Leu Pro Ser Ala Gln Ala Ser Asp Leu Ile Glu Asn
    290                 295                 300

Asp Asn His Gly Val Asp Leu Asp Met Arg Ile Ala Ser Val Leu Gln
305                 310                 315                 320

Ser Thr Gly His His Tyr Asp Gly Gly Phe Trp Thr Asp Phe Val Lys
                325                 330                 335

Pro Glu Thr Pro Glu Asn Lys Arg His Val Ala Ile Val Thr Thr Ala
            340                 345                 350

Ser Leu Pro Trp Met Thr Gly Thr Ala Val Asn Pro Leu Phe Arg Ala
        355                 360                 365

Ala Tyr Leu Ala Lys Ala Ala Lys Gln Ser Val Thr Leu Val Val Pro
    370                 375                 380

Trp Leu Cys Glu Ser Asp Gln Glu Leu Val Tyr Pro Asn Asn Leu Thr
385                 390                 395                 400

Phe Ser Ser Pro Glu Glu Gln Glu Ser Tyr Ile Arg Lys Trp Leu Glu
                405                 410                 415

Glu Arg Ile Gly Phe Lys Ala Asp Phe Lys Ile Ser Phe Tyr Pro Gly
            420                 425                 430

Lys Phe Ser Lys Glu Arg Arg Ser Ile Phe Pro Ala Gly Asp Thr Ser
        435                 440                 445

Gln Phe Ile Ser Ser Lys Asp Ala Asp Ile Ala Ile Leu Glu Glu Pro
    450                 455                 460

Glu His Leu Asn Trp Tyr Tyr His Gly Lys Arg Trp Thr Asp Lys Phe
465                 470                 475                 480

Asn His Val Val Gly Ile Val His Thr Asn Tyr Leu Glu Tyr Ile Lys
                485                 490                 495

Arg Glu Lys Asn Gly Ala Leu Gln Ala Phe Phe Val Asn His Val Asn
            500                 505                 510
```

```
Asn Trp Val Thr Arg Ala Tyr Cys Asp Lys Val Leu Arg Leu Ser Ala
        515                 520                 525

Ala Thr Gln Asp Leu Pro Lys Ser Val Val Cys Asn Val His Gly Val
    530                 535                 540

Asn Pro Lys Phe Leu Met Ile Gly Glu Lys Ile Ala Glu Glu Arg Ser
545                 550                 555                 560

Arg Gly Glu Gln Ala Phe Ser Lys Gly Ala Tyr Phe Leu Gly Lys Met
                565                 570                 575

Val Trp Ala Lys Gly Tyr Arg Glu Leu Ile Asp Leu Met Ala Lys His
            580                 585                 590

Lys Ser Glu Leu Gly Ser Phe Asn Leu Asp Val Tyr Gly Asn Gly Glu
        595                 600                 605

Asp Ala Val Glu Val Gln Arg Ala Ala Lys Lys His Asp Leu Asn Leu
    610                 615                 620

Asn Phe Leu Lys Gly Arg Asp His Ala Asp Asp Ala Leu His Lys Tyr
625                 630                 635                 640

Lys Val Phe Ile Asn Pro Ser Ile Ser Asp Val Leu Cys Thr Ala Thr
                645                 650                 655

Ala Glu Ala Leu Ala Met Gly Lys Phe Val Val Cys Ala Asp His Pro
            660                 665                 670

Ser Asn Glu Phe Phe Arg Ser Phe Pro Asn Cys Leu Thr Tyr Lys Thr
        675                 680                 685

Ser Glu Asp Phe Val Ser Lys Val Gln Glu Ala Met Thr Lys Glu Pro
    690                 695                 700

Leu Pro Leu Thr Pro Glu Gln Met Tyr Asn Leu Ser Trp Glu Ala Ala
705                 710                 715                 720

Thr Gln Arg Phe Met Glu Tyr Ser Asp Leu Asp Lys Ile Leu Asn Asn
                725                 730                 735

Gly Glu Gly Gly Arg Lys Met Arg Lys Ser Arg Ser Val Pro Ser Phe
            740                 745                 750

Asn Glu Val Val Asp Gly Gly Leu Ala Phe Ser His Tyr Val Leu Thr
        755                 760                 765

Gly Asn Asp Phe Leu Arg Leu Cys Thr Gly Ala Thr Pro Arg Thr Lys
    770                 775                 780

Asp Tyr Asp Asn Gln His Cys Lys Asp Leu Asn Leu Val Pro Pro His
785                 790                 795                 800

Val His Lys Pro Ile Phe Gly Trp
                805
```

<210> SEQ ID NO 25
<211> LENGTH: 1176
<212> TYPE: DNA
<213> ORGANISM: Arabidopsis thaliana

<400> SEQUENCE: 25

```
atggcgactt ttgctgaact tgttttatcg acttctcgct gtacatgccc ttgccgttca      60

ttcactagaa aacccctaat tcgtccccct ttatctggtc tgcgtctccc cggtgatacc     120

aaaccattgt ttcgttccgg acttggtcgg atttctgtta gccggcgttt cctcacggcc     180

gttgctcgag ctgaatcaga ccagcttggt gatgatgacc actcaaaggg aattgataga     240

atccataact tgcagaatgt ggaagataag cagaagaaag caagccagct taagaaaaga     300

gtgatctttg gtattggcat tggtttacct gttggatgtg ttgtgttagc tggaggatgg     360

gttttcactg tagctttagc atcttctgtt tttatcggtt cccgcgaata tttcgagctt     420

gttagaagta gaggcatagc taaaggaatg actcctcctc cacgatatgt atctcgagtt     480
```

```
tgctcggtta tatgtgccct tatgcccata cttacactgt actttggtaa cattgatata    540

ttggtgacat ctgcagcatt tgttgttgca atagcattgt tagtacaaag aggatcccca    600

cgttttgctc agctgagtag tacaatgttt ggtctgtttt actgtggtta tctcccttct    660

ttctgggtta agcttcgctg tggtttagct gctcctgcgc ttaacactgg tatcggaagg    720

acatggccaa ttcttcttgg tggtcaagct cattggacag ttggacttgt ggcaacattg    780

atttctttca gcggtgtaat tgcgacagac acatttgctt ttctcggtgg aaagactttt    840

ggtaggacac ctcttactag tattagtccc aagaagacat gggaaggaac tattgtagga    900

cttgttggtt gtatagccat taccatatta ctctctaaat atctcagttg gccacaatct    960

ctgttcagct cagtagcttt tgggtttctt aacttctttg ggtcagtctt tggtgatctt   1020

actgaatcaa tgatcaagcg tgatgctggc gtcaaagact ctggttcact tatcccagga   1080

cacggtggaa tattagatag agttgatagt tacattttca ccggcgcatt agcttattca   1140

ttcatcaaaa catccctaaa actttacgga gtttga                             1176
```

```
<210> SEQ ID NO 26
<211> LENGTH: 391
<212> TYPE: PRT
<213> ORGANISM: Arabidopsis thaliana

<400> SEQUENCE: 26

Met Ala Thr Phe Ala Glu Leu Val Leu Ser Thr Ser Arg Cys Thr Cys
1               5                   10                  15

Pro Cys Arg Ser Phe Thr Arg Lys Pro Leu Ile Arg Pro Pro Leu Ser
            20                  25                  30

Gly Leu Arg Leu Pro Gly Asp Thr Lys Pro Leu Phe Arg Ser Gly Leu
        35                  40                  45

Gly Arg Ile Ser Val Ser Arg Arg Phe Leu Thr Ala Val Ala Arg Ala
    50                  55                  60

Glu Ser Asp Gln Leu Gly Asp Asp Asp His Ser Lys Gly Ile Asp Arg
65                  70                  75                  80

Ile His Asn Leu Gln Asn Val Glu Asp Lys Gln Lys Lys Ala Ser Gln
                85                  90                  95

Leu Lys Lys Arg Val Ile Phe Gly Ile Gly Ile Gly Leu Pro Val Gly
            100                 105                 110

Cys Val Val Leu Ala Gly Gly Trp Val Phe Thr Val Ala Leu Ala Ser
        115                 120                 125

Ser Val Phe Ile Gly Ser Arg Glu Tyr Phe Glu Leu Val Arg Ser Arg
    130                 135                 140

Gly Ile Ala Lys Gly Met Thr Pro Pro Pro Arg Tyr Val Ser Arg Val
145                 150                 155                 160

Cys Ser Val Ile Cys Ala Leu Met Pro Ile Leu Thr Leu Tyr Phe Gly
                165                 170                 175

Asn Ile Asp Ile Leu Val Thr Ser Ala Ala Phe Val Val Ala Ile Ala
            180                 185                 190

Leu Leu Val Gln Arg Gly Ser Pro Arg Phe Ala Gln Leu Ser Ser Thr
        195                 200                 205

Met Phe Gly Leu Phe Tyr Cys Gly Tyr Leu Pro Ser Phe Trp Val Lys
    210                 215                 220

Leu Arg Cys Gly Leu Ala Ala Pro Ala Leu Asn Thr Gly Ile Gly Arg
225                 230                 235                 240

Thr Trp Pro Ile Leu Leu Gly Gly Gln Ala His Trp Thr Val Gly Leu
                245                 250                 255
```

```
Val Ala Thr Leu Ile Ser Phe Ser Gly Val Ile Ala Thr Asp Thr Phe
            260                 265                 270

Ala Phe Leu Gly Gly Lys Thr Phe Gly Arg Thr Pro Leu Thr Ser Ile
        275                 280                 285

Ser Pro Lys Lys Thr Trp Glu Gly Thr Ile Val Gly Leu Val Gly Cys
    290                 295                 300

Ile Ala Ile Thr Ile Leu Leu Ser Lys Tyr Leu Ser Trp Pro Gln Ser
305                 310                 315                 320

Leu Phe Ser Ser Val Ala Phe Gly Phe Leu Asn Phe Phe Gly Ser Val
                325                 330                 335

Phe Gly Asp Leu Thr Glu Ser Met Ile Lys Arg Asp Ala Gly Val Lys
            340                 345                 350

Asp Ser Gly Ser Leu Ile Pro Gly His Gly Gly Ile Leu Asp Arg Val
        355                 360                 365

Asp Ser Tyr Ile Phe Thr Gly Ala Leu Ala Tyr Ser Phe Ile Lys Thr
    370                 375                 380

Ser Leu Lys Leu Tyr Gly Val
385                 390


<210> SEQ ID NO 27
<211> LENGTH: 798
<212> TYPE: DNA
<213> ORGANISM: Arabidopsis thaliana

<400> SEQUENCE: 27

atggctcaaa ccatgctgct tacttcaggc gtcaccgccg gccatttttt gaggaacaag      60

agccctttgg ctcagcccaa agttcaccat ctcttcctct ctggaaactc tccggttgca     120

ctaccatcta ggagacaatc attcgttcct ctcgctctct tcaaacccaa aaccaaagct     180

gctcctaaaa aggttgagaa gccgaagagc aaggttgagg atggcatctt tggaacgtct     240

ggtgggattg gtttcacaaa ggcgaatgag ctattcgttg gtcgtgttgc tatgatcggt     300

ttcgctgcat cgttgcttgg tgaggcgttg acgggaaaag ggatattagc tcagctgaat     360

ctggagacag ggataccgat ttacgaagca gagccattgc ttctcttctt catcttgttc     420

actctgttgg gagccattgg agctctcgga gacagaggaa aattcgtcga cgatcctccc     480

accgggctcg agaaagccgt cattcctccc ggcaaaaacg tccgatctgc cctcggtctc     540

aaagaacaag gtccattgtt tgggttcacg aaggcgaacg agttattcgt aggaagattg     600

gcacagttgg gaatagcatt ttcactgata ggagagatta ttaccgggaa aggagcatta     660

gctcaactca acattgagac cggtatacca attcaagata tcgaaccact tgtcctctta     720

aacgttgctt tcttcttctt cgctgccatt aatcctggta atggaaaatt catcaccgat     780

gatggtgaag aaagctaa                                                   798


<210> SEQ ID NO 28
<211> LENGTH: 265
<212> TYPE: PRT
<213> ORGANISM: Arabidopsis thaliana

<400> SEQUENCE: 28

Met Ala Gln Thr Met Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30

Leu Ser Gly Asn Ser Pro Val Ala Leu Pro Ser Arg Arg Gln Ser Phe
        35                  40                  45
```

```
Val Pro Leu Ala Leu Phe Lys Pro Lys Thr Lys Ala Ala Pro Lys Lys
    50                  55                  60

Val Glu Lys Pro Lys Ser Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Phe Ala Ala Ile Asn Pro Gly Asn Gly Lys
                245                 250                 255

Phe Ile Thr Asp Asp Gly Glu Glu Ser
            260                 265
```

<210> SEQ ID NO 29
<211> LENGTH: 1152
<212> TYPE: DNA
<213> ORGANISM: Arabidopsis thaliana

<400> SEQUENCE: 29

```
atgggtgcag gtggaagaat gccggttcct acttcttcca agaaatcgga aaccgacacc      60

acaaagcgtg tgccgtgcga gaaaccgcct ttctcggtgg gagatctgaa gaaagcaatc     120

ccgccgcatt gtttcaaacg ctcaatccct cgctctttct cctaccttat cagtgacatc     180

attatagcct catgcttcta ctacgtcgcc accaattact tctctctcct ccctcagcct     240

ctctcttact tggcttggcc actctattgg gcctgtcaag gctgtgtcct aactggtatc     300

tgggtcatag cccacgaatg cggtcaccac gcattcagcg actaccaatg gctggatgac     360

acagttggtc ttatcttcca ttccttcctc ctcgtccctt acttctcctg gaagtatagt     420

catcgccgtc accattccaa cactggatcc ctcgaaagag atgaagtatt tgtcccaaag     480

cagaaatcag caatcaagtg gtacgggaaa tacctcaaca accctcttgg acgcatcatg     540

atgttaaccg tccagtttgt cctcgggtgg cccttgtact tagcctttaa cgtctctggc     600

agaccgtatg acgggttcgc ttgccatttc ttccccaacg ctcccatcta caatgaccga     660

gaacgcctcc agatatacct ctctgatgcg ggtattctag ccgtctgttt tggtctttac     720

cgttacgctg ctgcacaagg gatggcctcg atgatctgcc tctacggagt accgcttctg     780

atagtgaatg cgttcctcgt cttgatcact tacttgcagc acactcatcc ctcgttgcct     840

cactacgatt catcagagtg ggactggctc aggggagctt tggctaccgt agacagagac     900
```

```
tacggaatct tgaacaaggt gttccacaac attacagaca cacacgtggc tcatcacctg    960

ttctcgacaa tgccgcctta taacgcaatg gaagctacaa aggcgataaa gccaattctg   1020

ggagactatt accagttcga tggaacaccg tggtatgtag cgatgtatag ggaggcaaag   1080

gagtgtatct atgtagaacc ggacagggaa ggtgacaaga aaggtgtgta ctggtacaac   1140

aataagttat ga                                                       1152


<210> SEQ ID NO 30
<211> LENGTH: 383
<212> TYPE: PRT
<213> ORGANISM: Arabidopsis thaliana

<400> SEQUENCE: 30

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Pro His Cys Phe Lys Arg Ser
        35                  40                  45

Ile Pro Arg Ser Phe Ser Tyr Leu Ile Ser Asp Ile Ile Ile Ala Ser
    50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro Pro Tyr Asn Ala Met Glu Ala Thr Lys Ala Ile
```

```
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380


<210> SEQ ID NO 31
<211> LENGTH: 1056
<212> TYPE: DNA
<213> ORGANISM: Brassica napus

<400> SEQUENCE: 31

atggcttcaa taaatgaaga tgtgtctatt ggaaacttag gcagtctcca aacactccca      60

gactcattca cctggaaact caccgctgct gactccattc tccctccctc ctccgccgct     120

gtgaaagagt ccattccggt catcgacctc tccgatcctg acgtcaccaa tttgttagga     180

aatgcatgca aaacgtgggg agcgtttcag atagccaacc acggggtctc tcaaagtctc     240

ctcgacgacg ttgaatctct ctccaaaacc tttttcgata tgccgtcaga gaggaaactc     300

gaggctgctt cctctaataa aggagttagt gggtacggag aacctcgaat ctctcttttc     360

ttcgagaaga aaatgtggtc tgaagggttg acaatcgccg acggctccta ccgcaaccag     420

ttccttacta tttggccccg tgattacacc aaatactgcg gaataatcga agagtacaag     480

ggtgaaatgg aaaaattagc aagcagactt ctatcatgca tattaggatc acttggtgtc     540

accgtagacg acatcgaatg ggctaagaag accgagaaat ctgaatcaaa aatgggccaa     600

agcgtcatac gactaaacca ttacccggtt tgtcctgagc cagaaagagc catgggtcta     660

gccgctcata ccgactcatg tcttctaacc attttgcacc agagcaacat gggagggcta     720

caagtgttca aagaagagtc cggttgggtt acggtagagc ccattcctgg tgttcttgtg     780

gtcaacatcg gcgacctctt tcacattcta tcgaatggga agtttcctag cgtggttcac     840

cgagcaaggg ttaaccgaac caagtcaaga atatcgatag cgtatctgtg gggtggtcca     900

gccggtgaag tggagataag tccaatatca aagatagttg gtccggttgg accgtgtcta     960

taccggccag ttacttggag tgaatatctc cgaatcaaat ttgaggtttt cgacaaggca    1020

ttggacgcaa ttggagtcgt taatcccacc aattga                              1056


<210> SEQ ID NO 32
<211> LENGTH: 351
<212> TYPE: PRT
<213> ORGANISM: Brassica napus

<400> SEQUENCE: 32

Met Ala Ser Ile Asn Glu Asp Val Ser Ile Gly Asn Leu Gly Ser Leu
1               5                   10                  15

Gln Thr Leu Pro Asp Ser Phe Thr Trp Lys Leu Thr Ala Ala Asp Ser
            20                  25                  30

Ile Leu Pro Pro Ser Ser Ala Ala Val Lys Glu Ser Ile Pro Val Ile
        35                  40                  45

Asp Leu Ser Asp Pro Asp Val Thr Asn Leu Leu Gly Asn Ala Cys Lys
    50                  55                  60

Thr Trp Gly Ala Phe Gln Ile Ala Asn His Gly Val Ser Gln Ser Leu
65                  70                  75                  80

Leu Asp Asp Val Glu Ser Leu Ser Lys Thr Phe Phe Asp Met Pro Ser
                85                  90                  95
```

-continued

```
Glu Arg Lys Leu Glu Ala Ala Ser Ser Asn Lys Gly Val Ser Gly Tyr
            100                 105                 110

Gly Glu Pro Arg Ile Ser Leu Phe Phe Glu Lys Lys Met Trp Ser Glu
        115                 120                 125

Gly Leu Thr Ile Ala Asp Gly Ser Tyr Arg Asn Gln Phe Leu Thr Ile
    130                 135                 140

Trp Pro Arg Asp Tyr Thr Lys Tyr Cys Gly Ile Ile Glu Glu Tyr Lys
145                 150                 155                 160

Gly Glu Met Glu Lys Leu Ala Ser Arg Leu Leu Ser Cys Ile Leu Gly
                165                 170                 175

Ser Leu Gly Val Thr Val Asp Asp Ile Glu Trp Ala Lys Lys Thr Glu
            180                 185                 190

Lys Ser Glu Ser Lys Met Gly Gln Ser Val Ile Arg Leu Asn His Tyr
        195                 200                 205

Pro Val Cys Pro Glu Pro Glu Arg Ala Met Gly Leu Ala Ala His Thr
    210                 215                 220

Asp Ser Cys Leu Leu Thr Ile Leu His Gln Ser Asn Met Gly Gly Leu
225                 230                 235                 240

Gln Val Phe Lys Glu Glu Ser Gly Trp Val Thr Val Glu Pro Ile Pro
                245                 250                 255

Gly Val Leu Val Val Asn Ile Gly Asp Leu Phe His Ile Leu Ser Asn
            260                 265                 270

Gly Lys Phe Pro Ser Val Val His Arg Ala Arg Val Asn Arg Thr Lys
        275                 280                 285

Ser Arg Ile Ser Ile Ala Tyr Leu Trp Gly Gly Pro Ala Gly Glu Val
    290                 295                 300

Glu Ile Ser Pro Ile Ser Lys Ile Val Gly Pro Val Gly Pro Cys Leu
305                 310                 315                 320

Tyr Arg Pro Val Thr Trp Ser Glu Tyr Leu Arg Ile Lys Phe Glu Val
                325                 330                 335

Phe Asp Lys Ala Leu Asp Ala Ile Gly Val Val Asn Pro Thr Asn
            340                 345                 350
```

<210> SEQ ID NO 33
<211> LENGTH: 639
<212> TYPE: DNA
<213> ORGANISM: Brassica napus

<400> SEQUENCE: 33

```
atggctacat tctcttgtaa ttcttatgaa caaaatcacg ctcctttcga ccgtcacgct      60

aatgatactg atattgatga tcctgatcat gatcatcatg atggtgttca gcaagaggag     120

agtggatgga caacttatct tgaagatttc tcaaatcaat acagaactca tcctgaagat     180

aacgatcatc aagataagag ttcgtgttcg attctggacg cctctccttc tctggtctcc     240

gacgccgcca ctgacgcatt ttctggccgg agttttccag ttaattttcc ggtgaaattg     300

aagtttggga aggcaagaac caaaaagatt tgtgaggatg attctttgga ggatacggct     360

agctctccgg ttaatagccc taaggtcagt cagattgaac atattcagac gcctcctaga     420

aaacatgagg actatgtctc ttctagtttc gttatgggaa atatgagtgg catgggggat     480

catcaaatcc aaatccaaga aggagatgaa caaaagttga cgatgatgag gaatctcaga     540

gaaggaaaca acagtaacag taataatatg gacttgaggg ctagaggatt atgcgtcgtc     600

cctatttcca tgttgggtaa ttttaatggc cgcttctga                            639
```

<210> SEQ ID NO 34
<211> LENGTH: 212
<212> TYPE: PRT
<213> ORGANISM: Brassica napus

<400> SEQUENCE: 34

```
Met Ala Thr Phe Ser Cys Asn Ser Tyr Glu Gln Asn His Ala Pro Phe
1               5                   10                  15

Asp Arg His Ala Asn Asp Thr Asp Ile Asp Asp Pro Asp His Asp His
            20                  25                  30

His Asp Gly Val Gln Gln Glu Glu Ser Gly Trp Thr Thr Tyr Leu Glu
        35                  40                  45

Asp Phe Ser Asn Gln Tyr Arg Thr His Pro Glu Asp Asn Asp His Gln
    50                  55                  60

Asp Lys Ser Ser Cys Ser Ile Leu Asp Ala Ser Pro Ser Leu Val Ser
65                  70                  75                  80

Asp Ala Ala Thr Asp Ala Phe Ser Gly Arg Ser Phe Pro Val Asn Phe
                85                  90                  95

Pro Val Lys Leu Lys Phe Gly Lys Ala Arg Thr Lys Lys Ile Cys Glu
            100                 105                 110

Asp Asp Ser Leu Glu Asp Thr Ala Ser Ser Pro Val Asn Ser Pro Lys
        115                 120                 125

Val Ser Gln Ile Glu His Ile Gln Thr Pro Pro Arg Lys His Glu Asp
    130                 135                 140

Tyr Val Ser Ser Ser Phe Val Met Gly Asn Met Ser Gly Met Gly Asp
145                 150                 155                 160

His Gln Ile Gln Ile Gln Glu Gly Asp Glu Gln Lys Leu Thr Met Met
                165                 170                 175

Arg Asn Leu Arg Glu Gly Asn Asn Ser Asn Ser Asn Asn Met Asp Leu
            180                 185                 190

Arg Ala Arg Gly Leu Cys Val Val Pro Ile Ser Met Leu Gly Asn Phe
        195                 200                 205

Asn Gly Arg Phe
    210
```

<210> SEQ ID NO 35
<211> LENGTH: 1143
<212> TYPE: DNA
<213> ORGANISM: Arabidopsis thaliana

<400> SEQUENCE: 35

```
atggcaacgg aatgcattgc aacggtccct caaatattca gtgaaaacaa aaccaaagag     60

gattcttcga tcttcgatgc aaagctcctt aatcagcact cacaccacat acctcaacag    120

ttcgtatggc ccgaccacga gaaaccttct acggatgttc aacctctcca agtcccactc    180

atagacctag ccggtttcct ctccggcgac tcgtgcttgg catcggaggc tactagactc    240

gtctcaaagg ctgcaacgaa acatggcttc ttcctaatca ctaaccatgg tatcgatgag    300

agcctcttgt ctcgtgccta tctgcatatg gactctttct ttaaggcccc ggcttgtgag    360

aagcagaagg ctcagaggaa gtggggtgag agctccggtt acgctagtag tttcgtcggg    420

agattctcct caaagctccc gtggaaggag actctgtcgt ttaagttctc tcccgaggag    480

aagatccatt cccaaaccgt taaagacttt gtttctaaga aaatgtgcga tggatacgaa    540

gatttcggga aggtttatca agaatacgcg gaggccatga acactctctc actaaagatc    600

atggagcttc ttggaatgag tcttggggtc gagaggagat attttaaaga gtttttcgaa    660

gacagcgatt caatattccg gttgaattac tacccgcagt gcaagcaacc ggagcttgca    720
```

```
ctagggacag gaccccactg cgacccaaca tctctaacca tacttcatca agaccaagtt     780

ggcggtctgc aagttttcgt ggacaacaaa tggcaatcca ttcctcctaa ccctcacgct     840

ttcgtggtga acataggcga caccttcatg gctctaacga atggaagata caagagttgt     900

ttgcatcggg cggtggtgaa cagcgagaga gaaaggaaga cgtttgcatt cttcctatgt     960

ccgaaagggg aaaaagtggt gaagccacca gaagaactag taaacggagt gaagtctggt    1020

gaaagaaagt atcctgattt tacgtggtct atgtttctcg agttcacaca gaagcattat    1080

agggcagaca tgaacactct tgacgagttc tcaatttggc ttaagaacag aagaagtttc    1140

taa                                                                  1143
```

```
<210> SEQ ID NO 36
<211> LENGTH: 380
<212> TYPE: PRT
<213> ORGANISM: Arabidopsis thaliana

<400> SEQUENCE: 36

Met Ala Thr Glu Cys Ile Ala Thr Val Pro Gln Ile Phe Ser Glu Asn
1               5                   10                  15

Lys Thr Lys Glu Asp Ser Ser Ile Phe Asp Ala Lys Leu Leu Asn Gln
            20                  25                  30

His Ser His His Ile Pro Gln Gln Phe Val Trp Pro Asp His Glu Lys
        35                  40                  45

Pro Ser Thr Asp Val Gln Pro Leu Gln Val Pro Leu Ile Asp Leu Ala
    50                  55                  60

Gly Phe Leu Ser Gly Asp Ser Cys Leu Ala Ser Glu Ala Thr Arg Leu
65                  70                  75                  80

Val Ser Lys Ala Ala Thr Lys His Gly Phe Phe Leu Ile Thr Asn His
                85                  90                  95

Gly Ile Asp Glu Ser Leu Leu Ser Arg Ala Tyr Leu His Met Asp Ser
            100                 105                 110

Phe Phe Lys Ala Pro Ala Cys Glu Lys Gln Lys Ala Gln Arg Lys Trp
        115                 120                 125

Gly Glu Ser Ser Gly Tyr Ala Ser Ser Phe Val Gly Arg Phe Ser Ser
    130                 135                 140

Lys Leu Pro Trp Lys Glu Thr Leu Ser Phe Lys Phe Ser Pro Glu Glu
145                 150                 155                 160

Lys Ile His Ser Gln Thr Val Lys Asp Phe Val Ser Lys Lys Met Cys
                165                 170                 175

Asp Gly Tyr Glu Asp Phe Gly Lys Val Tyr Gln Glu Tyr Ala Glu Ala
            180                 185                 190

Met Asn Thr Leu Ser Leu Lys Ile Met Glu Leu Leu Gly Met Ser Leu
        195                 200                 205

Gly Val Glu Arg Arg Tyr Phe Lys Glu Phe Phe Glu Asp Ser Asp Ser
    210                 215                 220

Ile Phe Arg Leu Asn Tyr Tyr Pro Gln Cys Lys Gln Pro Glu Leu Ala
225                 230                 235                 240

Leu Gly Thr Gly Pro His Cys Asp Pro Thr Ser Leu Thr Ile Leu His
                245                 250                 255

Gln Asp Gln Val Gly Gly Leu Gln Val Phe Val Asp Asn Lys Trp Gln
            260                 265                 270

Ser Ile Pro Pro Asn Pro His Ala Phe Val Val Asn Ile Gly Asp Thr
        275                 280                 285

Phe Met Ala Leu Thr Asn Gly Arg Tyr Lys Ser Cys Leu His Arg Ala
```

```
    290                 295                 300

Val Val Asn Ser Glu Arg Glu Arg Lys Thr Phe Ala Phe Phe Leu Cys
305                 310                 315                 320

Pro Lys Gly Glu Lys Val Val Lys Pro Pro Glu Glu Leu Val Asn Gly
                325                 330                 335

Val Lys Ser Gly Glu Arg Lys Tyr Pro Asp Phe Thr Trp Ser Met Phe
            340                 345                 350

Leu Glu Phe Thr Gln Lys His Tyr Arg Ala Asp Met Asn Thr Leu Asp
        355                 360                 365

Glu Phe Ser Ile Trp Leu Lys Asn Arg Arg Ser Phe
    370                 375                 380


<210> SEQ ID NO 37
<211> LENGTH: 1908
<212> TYPE: DNA
<213> ORGANISM: Arabidopsis thaliana

<400> SEQUENCE: 37

atggcgtcag agcaagcaag gagagaaaac aaggtgacgg agagagaagt tcaggtggag      60

aaagacagag tcccaaagat gacgagtcat ttcgagtcca tggccgaaaa aggcaaagat     120

tccgacacac acaggcatca aacagaaggt ggtgggacac agttcgtgtc tctctcagac     180

aaggggagta acatgccggt ttctgatgaa ggagagggag agacgaagat gaagaggact     240

cagatgcctc actccgttgg aaaattcgtt actagcagcg attcaggaac agggaagaag     300

aaggatgaga aagaggagca tgagaaggcg tcgctagagg atattcatgg gtatagagcc     360

aatgctcagc agaagtcaat ggatagtata aaagcagcag aggaaaggta taacaaggct     420

aaggagagtt tgagccatag tggacaagaa gctcgtggag gaagaggtga agaaatggtg     480

ggaaaagggc gggacagtgg tgtccgtgtt tctcacgttg ggctgttggt tggcggtggt     540

ggaggtgagg aaaaagagag tggtgtacat ggctttcatg gggagaaagc acgacatgct     600

gagcttttgg ctgccggagg tgaggagatg agagaacgtg aaggtaaaga atcagcaggt     660

ggtgttggtg gtcgtagcgt aaaagatacg gtagccgaga aaggacagca agctaaggaa     720

agtgtaggag aaggtgctca gaaagcgggc agtgctacga gtgagaaagc tcagagagct     780

tccgagtatg caacagagaa aggaaaagaa gctggaaata tgacagctga acaggcggcg     840

agagcaaaag actatgctct gcagaaagct gttgaagcta aagagactgc ggcggagaaa     900

gctcagagag cttccgagta tatgaaggaa acaggaagca cagcggctga acaggctgcg     960

agagctaaag attacactct tcagaaagct gtggaagcta aagatgttgc agctgagaaa    1020

gctcagagag cttcagaata catgacagag acaggaaaac aagccggaaa tgttgcagct    1080

cagaaagggc aagaggcagc ttcaatgaca gcaaaagcta aagattatac tgttcagaaa    1140

gccggtgaag cagctgggta cataaaagaa acgacagtgg aaggaggaaa aggagctgca    1200

cattatgcag gagtggcagc tgagaaagcc gctgcggttg ggtggacagc ggcacatttc    1260

accacggaga aagtggtgca agggacgaaa gcggttgcag gtacagtgga aggtgctgtg    1320

gggtacgcag ggcataaggc ggtggaagta ggatctaagg cagtggactt gactaaggag    1380

aaagctgcag tggctgctga tacggtggtt gggtatacgg cgaggaagaa agaggaagct    1440

caacacagag accaagagat gcatcaggga ggtgaggaag aaaagcaacc agggtttgtc    1500

tcaggagcaa ggagagactt tggagaagag tacggggaag aaagagggag tgagaaagat    1560

gtctacggct atggagcaaa aggaataccc ggagaaggga ggggagatgt tggggaggca    1620

gagtacggaa gagggagtga gaaagatgtc ttcggatatg gaccaaaagg cacggtcgaa    1680
```

```
gaagcaagga gagacgttgg agaagaatac ggaggaggaa gaggcagtga gagatatgtt   1740

gaagaagaag ggttggagc gggaggggtg cttggggcaa tcggcgagac tatagctgag   1800

attgcacaga cgacaaagaa catagtgatt ggtgatgcgc ctgtgaggac acatgagcat   1860

ggaactactg atcctgacta tatgagacgg gaacatggac aacgttga                1908
```

```
<210> SEQ ID NO 38
<211> LENGTH: 635
<212> TYPE: PRT
<213> ORGANISM: Arabidopsis thaliana

<400> SEQUENCE: 38

Met Ala Ser Glu Gln Ala Arg Arg Glu Asn Lys Val Thr Glu Arg Glu
1               5                   10                  15

Val Gln Val Glu Lys Asp Arg Val Pro Lys Met Thr Ser His Phe Glu
            20                  25                  30

Ser Met Ala Glu Lys Gly Lys Asp Ser Asp Thr His Arg His Gln Thr
        35                  40                  45

Glu Gly Gly Gly Thr Gln Phe Val Ser Leu Ser Asp Lys Gly Ser Asn
    50                  55                  60

Met Pro Val Ser Asp Glu Gly Glu Gly Glu Thr Lys Met Lys Arg Thr
65                  70                  75                  80

Gln Met Pro His Ser Val Gly Lys Phe Val Thr Ser Ser Asp Ser Gly
                85                  90                  95

Thr Gly Lys Lys Lys Asp Glu Lys Glu Glu His Glu Lys Ala Ser Leu
            100                 105                 110

Glu Asp Ile His Gly Tyr Arg Ala Asn Ala Gln Gln Lys Ser Met Asp
        115                 120                 125

Ser Ile Lys Ala Ala Glu Glu Arg Tyr Asn Lys Ala Lys Glu Ser Leu
    130                 135                 140

Ser His Ser Gly Gln Glu Ala Arg Gly Gly Arg Gly Glu Glu Met Val
145                 150                 155                 160

Gly Lys Gly Arg Asp Ser Gly Val Arg Val Ser His Val Gly Ala Val
                165                 170                 175

Gly Gly Gly Gly Gly Gly Glu Glu Lys Glu Ser Gly Val His Gly Phe
            180                 185                 190

His Gly Glu Lys Ala Arg His Ala Glu Leu Leu Ala Ala Gly Gly Glu
        195                 200                 205

Glu Met Arg Glu Arg Glu Gly Lys Glu Ser Ala Gly Gly Val Gly Gly
    210                 215                 220

Arg Ser Val Lys Asp Thr Val Ala Glu Lys Gly Gln Gln Ala Lys Glu
225                 230                 235                 240

Ser Val Gly Glu Gly Ala Gln Lys Ala Gly Ser Ala Thr Ser Glu Lys
                245                 250                 255

Ala Gln Arg Ala Ser Glu Tyr Ala Thr Glu Lys Gly Lys Glu Ala Gly
            260                 265                 270

Asn Met Thr Ala Glu Gln Ala Ala Arg Ala Lys Asp Tyr Ala Leu Gln
        275                 280                 285

Lys Ala Val Glu Ala Lys Glu Thr Ala Ala Glu Lys Ala Gln Arg Ala
    290                 295                 300

Ser Glu Tyr Met Lys Glu Thr Gly Ser Thr Ala Ala Glu Gln Ala Ala
305                 310                 315                 320

Arg Ala Lys Asp Tyr Thr Leu Gln Lys Ala Val Glu Ala Lys Asp Val
                325                 330                 335
```

```
Ala Ala Glu Lys Ala Gln Arg Ala Ser Glu Tyr Met Thr Glu Thr Gly
            340                 345                 350

Lys Gln Ala Gly Asn Val Ala Ala Gln Lys Gly Gln Glu Ala Ala Ser
        355                 360                 365

Met Thr Ala Lys Ala Lys Asp Tyr Thr Val Gln Lys Ala Gly Glu Ala
    370                 375                 380

Ala Gly Tyr Ile Lys Glu Thr Thr Val Glu Gly Gly Lys Gly Ala Ala
385                 390                 395                 400

His Tyr Ala Gly Val Ala Ala Glu Lys Ala Ala Ala Val Gly Trp Thr
                405                 410                 415

Ala Ala His Phe Thr Thr Glu Lys Val Val Gln Gly Thr Lys Ala Val
            420                 425                 430

Ala Gly Thr Val Glu Gly Ala Val Gly Tyr Ala Gly His Lys Ala Val
        435                 440                 445

Glu Val Gly Ser Lys Ala Val Asp Leu Thr Lys Glu Lys Ala Ala Val
    450                 455                 460

Ala Ala Asp Thr Val Val Gly Tyr Thr Ala Arg Lys Lys Glu Glu Ala
465                 470                 475                 480

Gln His Arg Asp Gln Glu Met His Gln Gly Gly Glu Glu Glu Lys Gln
                485                 490                 495

Pro Gly Phe Val Ser Gly Ala Arg Arg Asp Phe Gly Glu Glu Tyr Gly
            500                 505                 510

Glu Glu Arg Gly Ser Glu Lys Asp Val Tyr Gly Tyr Gly Ala Lys Gly
        515                 520                 525

Ile Pro Gly Glu Gly Arg Gly Asp Val Gly Glu Ala Glu Tyr Gly Arg
    530                 535                 540

Gly Ser Glu Lys Asp Val Phe Gly Tyr Gly Pro Lys Gly Thr Val Glu
545                 550                 555                 560

Glu Ala Arg Arg Asp Val Gly Glu Glu Tyr Gly Gly Gly Arg Gly Ser
                565                 570                 575

Glu Arg Tyr Val Glu Glu Glu Gly Val Gly Ala Gly Gly Val Leu Gly
            580                 585                 590

Ala Ile Gly Glu Thr Ile Ala Glu Ile Ala Gln Thr Thr Lys Asn Ile
        595                 600                 605

Val Ile Gly Asp Ala Pro Val Arg Thr His Glu His Gly Thr Thr Asp
    610                 615                 620

Pro Asp Tyr Met Arg Arg Glu His Gly Gln Arg
625                 630                 635
```

<210> SEQ ID NO 39
<211> LENGTH: 1461
<212> TYPE: DNA
<213> ORGANISM: Arabidopsis thaliana

<400> SEQUENCE: 39

```
atggctaagt cttgctattt cagaccagct cttcttcttc tgttagttct tttggttcat      60

gccgagtcac gcggtcggtt cgagccaaag attcttatgc cgacagagga agctaacccg     120

gctgaccaag acggagatgg tgtcggtaca agatgggcgg ttctcgtcgc tggttcttct     180

ggatatggaa actacagaca ccaggctgac atgtgtcacg catatcaaat actaagaaaa     240

ggaggtttaa aggaagagaa catagtcgtt ttgatgtatg atgatatcgc aaaccaccca     300

cttaatcctc gtccgggtac tctcatcaac catcctgacg gtgacgatgt ttacgccgga     360

gtccctaagg actatactgg tagtagtgtt acggctgcaa acttctacgc tgtactccta     420

ggcgaccaga aggctgttaa aggtggaagc ggtaaggtca tcgctagcaa gcccaacgat     480
```

```
cacattttcg tatattatgc ggatcatggt ggtcccggag ttcttgggat gccaaatacg    540

cctcacatat atgcagctga ttttattgaa acgcttaaga agaagcatgc ttccggaaca    600

tacaaagaga tggttatata cgtagaagcg tgtgaaagtg ggagtatttt cgaagggata    660

atgccaaagg acttgaacat ttacgtaaca acggcttcaa atgcacaaga gagtagttat    720

ggaacatatt gtcctggcat gaatccgtca cccccatctg aatatatcac ttgcttaggg    780

gatttatata gtgttgcttg gatggaagat agtgagactc acaatttaaa gaaagagacc    840

ataaagcaac aataccacac ggtgaagatg aggacatcaa actacaatac ctactcaggt    900

ggctctcatg tgatggaata cggtaacaat agtattaagt cggagaagct ttatctttac    960

caagggtttg atccagccac cgttaatctc ccactaaacg aattaccggt caagtcaaaa   1020

ataggagtcg ttaaccaacg cgatgcggac cttctcttcc tttggcatat gtatcggaca   1080

tcggaagatg ggtcaaggaa gaaggatgac acattgaagg aattaactga gacaacaagg   1140

cataggaaac atttagatgc aagcgtcgaa ttgatagcca caattttgtt tggtccgacg   1200

atgaatgttc ttaacttggt tagagaaccc ggtttgcctt tggttgacga ttgggaatgt   1260

cttaaatcga tggtacgtgt atttgaagag cattgtggat cactaacgca atatgggatg   1320

aaacatatgc gagcgtttgc aaacgtttgt aacaacggtg tgtccaaaga gctgatggag   1380

gaagcttcta ctgcggcatg cggtggttat agtgaggctc gctacacggt gcatccatca   1440

atcttaggct atagcgcctg a                                             1461
```

```
<210> SEQ ID NO 40
<211> LENGTH: 486
<212> TYPE: PRT
<213> ORGANISM: Arabidopsis thaliana

<400> SEQUENCE: 40

Met Ala Lys Ser Cys Tyr Phe Arg Pro Ala Leu Leu Leu Leu Leu Val
1               5                   10                  15

Leu Leu Val His Ala Glu Ser Arg Gly Arg Phe Glu Pro Lys Ile Leu
            20                  25                  30

Met Pro Thr Glu Glu Ala Asn Pro Ala Asp Gln Asp Gly Asp Gly Val
        35                  40                  45

Gly Thr Arg Trp Ala Val Leu Val Ala Gly Ser Ser Gly Tyr Gly Asn
    50                  55                  60

Tyr Arg His Gln Ala Asp Met Cys His Ala Tyr Gln Ile Leu Arg Lys
65                  70                  75                  80

Gly Gly Leu Lys Glu Glu Asn Ile Val Val Leu Met Tyr Asp Asp Ile
                85                  90                  95

Ala Asn His Pro Leu Asn Pro Arg Pro Gly Thr Leu Ile Asn His Pro
            100                 105                 110

Asp Gly Asp Asp Val Tyr Ala Gly Val Pro Lys Asp Tyr Thr Gly Ser
        115                 120                 125

Ser Val Thr Ala Ala Asn Phe Tyr Ala Val Leu Leu Gly Asp Gln Lys
    130                 135                 140

Ala Val Lys Gly Gly Ser Gly Lys Val Ile Ala Ser Lys Pro Asn Asp
145                 150                 155                 160

His Ile Phe Val Tyr Tyr Ala Asp His Gly Gly Pro Gly Val Leu Gly
                165                 170                 175

Met Pro Asn Thr Pro His Ile Tyr Ala Ala Asp Phe Ile Glu Thr Leu
            180                 185                 190

Lys Lys Lys His Ala Ser Gly Thr Tyr Lys Glu Met Val Ile Tyr Val
```

```
        195                 200                 205

Glu Ala Cys Glu Ser Gly Ser Ile Phe Glu Gly Ile Met Pro Lys Asp
    210                 215                 220

Leu Asn Ile Tyr Val Thr Thr Ala Ser Asn Ala Gln Glu Ser Ser Tyr
225                 230                 235                 240

Gly Thr Tyr Cys Pro Gly Met Asn Pro Ser Pro Pro Ser Glu Tyr Ile
                245                 250                 255

Thr Cys Leu Gly Asp Leu Tyr Ser Val Ala Trp Met Glu Asp Ser Glu
            260                 265                 270

Thr His Asn Leu Lys Lys Glu Thr Ile Lys Gln Gln Tyr His Thr Val
        275                 280                 285

Lys Met Arg Thr Ser Asn Tyr Asn Thr Tyr Ser Gly Gly Ser His Val
    290                 295                 300

Met Glu Tyr Gly Asn Asn Ser Ile Lys Ser Glu Lys Leu Tyr Leu Tyr
305                 310                 315                 320

Gln Gly Phe Asp Pro Ala Thr Val Asn Leu Pro Leu Asn Glu Leu Pro
                325                 330                 335

Val Lys Ser Lys Ile Gly Val Val Asn Gln Arg Asp Ala Asp Leu Leu
            340                 345                 350

Phe Leu Trp His Met Tyr Arg Thr Ser Glu Asp Gly Ser Arg Lys Lys
        355                 360                 365

Asp Asp Thr Leu Lys Glu Leu Thr Glu Thr Thr Arg His Arg Lys His
    370                 375                 380

Leu Asp Ala Ser Val Glu Leu Ile Ala Thr Ile Leu Phe Gly Pro Thr
385                 390                 395                 400

Met Asn Val Leu Asn Leu Val Arg Glu Pro Gly Leu Pro Leu Val Asp
                405                 410                 415

Asp Trp Glu Cys Leu Lys Ser Met Val Arg Val Phe Glu Glu His Cys
            420                 425                 430

Gly Ser Leu Thr Gln Tyr Gly Met Lys His Met Arg Ala Phe Ala Asn
        435                 440                 445

Val Cys Asn Asn Gly Val Ser Lys Glu Leu Met Glu Glu Ala Ser Thr
    450                 455                 460

Ala Ala Cys Gly Gly Tyr Ser Glu Ala Arg Tyr Thr Val His Pro Ser
465                 470                 475                 480

Ile Leu Gly Tyr Ser Ala
                485
```

<210> SEQ ID NO 41
<211> LENGTH: 1551
<212> TYPE: DNA
<213> ORGANISM: Arabidopsis thaliana

<400> SEQUENCE: 41

```
atggacggtg ccggagaatc acgactcggt ggtgatggtg gtggtgatgg ttctgttgga      60

gttcagatcc gacaaacacg gatgctaccg gattttctcc agagcgtgaa tctcaagtat     120

gtgaaattag gttaccatta cttaatctca aatctcttga ctctctgttt attccctctc     180

gccgttgtta tctccgtcga agcctctcag atgaacccag atgatctcaa acagctctgg     240

atccatctac aatacaatct ggttagtatc atcatctgtt cagcgattct agtcttcggg     300

ttaacggttt atgttatgac ccgacctaga cccgtttact tggttgattt ctcttgttat     360

ctcccacctg atcatctcaa agctccttac gctcggttca tggaacattc tagactcacc     420

ggagatttcg atgactctgc tctcgagttt caacgcaaga tccttgagcg ttctggttta     480
```

```
gggaagaca cttatgtccc tgaagctatg cattatgttc caccgagaat ttcaatggct    540

gctgctagag aagaagctga acaagtcatg tttggtgctt tagataacct tttcgctaac    600

actaatgtga aaccaaagga tattggaatc cttgttgtga attgtagtct ctttaatcca    660

actccttcgt tatctgcaat gattgtgaac aagtataagc ttagaggtaa cattagaagc    720

tacaatctag gcggtatggg ttgcagcgcg ggagttatcg ctgtggatct tgctaaagac    780

atgttgttgg tacataggaa cacttatgcg gttgttgttt ctactgagaa cattactcag    840

aattggtatt ttggtaacaa gaaatcgatg ttgataccga actgcttgtt tcgagttggt    900

ggctctgcgg ttttgctatc gaacaagtcg agggacaaga gacggtctaa gtacaggctt    960

gtacatgtag tcaggactca ccgtggagca gatgataaag ctttccgttg tgtttatcaa   1020

gagcaggatg atacagggag aaccggggtt tcgttgtcga aagatctaat ggcgattgca   1080

ggggaaactc tcaaaaccaa tatcactaca ttgggtcctc ttgttctacc gataagtgag   1140

cagattctct tctttatgac tctagttgtg aagaagctct ttaacggtaa agtgaaaccg   1200

tatatcccgg atttcaaact tgctttcgag catttctgta tccatgctgg tggaagagct   1260

gtgatcgatg agttagagaa gaatctgcag ctttcaccag ttcatgtcga ggcttcgagg   1320

atgactcttc atcgatttgg taacacatct tcgagctcca tttggtatga attggcttac   1380

attgaagcga agggaaggat gcgaagaggt aatcgtgttt ggcaaatcgc gttcggaagt   1440

ggatttaaat gtaatagcgc gatttgggaa gcattaaggc atgtgaaacc ttcgaacaac   1500

agtccttggg aagattgtat tgacaagtat ccggtaactt taagttatta g            1551
```

```
<210> SEQ ID NO 42
<211> LENGTH: 516
<212> TYPE: PRT
<213> ORGANISM: Arabidopsis thaliana

<400> SEQUENCE: 42

Met Asp Gly Ala Gly Glu Ser Arg Leu Gly Gly Asp Gly Gly Gly Asp
1               5                   10                  15

Gly Ser Val Gly Val Gln Ile Arg Gln Thr Arg Met Leu Pro Asp Phe
            20                  25                  30

Leu Gln Ser Val Asn Leu Lys Tyr Val Lys Leu Gly Tyr His Tyr Leu
        35                  40                  45

Ile Ser Asn Leu Leu Thr Leu Cys Leu Phe Pro Leu Ala Val Val Ile
    50                  55                  60

Ser Val Glu Ala Ser Gln Met Asn Pro Asp Asp Leu Lys Gln Leu Trp
65                  70                  75                  80

Ile His Leu Gln Tyr Asn Leu Val Ser Ile Ile Ile Cys Ser Ala Ile
                85                  90                  95

Leu Val Phe Gly Leu Thr Val Tyr Val Met Thr Arg Pro Arg Pro Val
            100                 105                 110

Tyr Leu Val Asp Phe Ser Cys Tyr Leu Pro Pro Asp His Leu Lys Ala
        115                 120                 125

Pro Tyr Ala Arg Phe Met Glu His Ser Arg Leu Thr Gly Asp Phe Asp
    130                 135                 140

Asp Ser Ala Leu Glu Phe Gln Arg Lys Ile Leu Glu Arg Ser Gly Leu
145                 150                 155                 160

Gly Glu Asp Thr Tyr Val Pro Glu Ala Met His Tyr Val Pro Pro Arg
                165                 170                 175

Ile Ser Met Ala Ala Ala Arg Glu Glu Ala Glu Gln Val Met Phe Gly
            180                 185                 190
```

```
Ala Leu Asp Asn Leu Phe Ala Asn Thr Asn Val Lys Pro Lys Asp Ile
        195                 200                 205

Gly Ile Leu Val Val Asn Cys Ser Leu Phe Asn Pro Thr Pro Ser Leu
    210                 215                 220

Ser Ala Met Ile Val Asn Lys Tyr Lys Leu Arg Gly Asn Ile Arg Ser
225                 230                 235                 240

Tyr Asn Leu Gly Gly Met Gly Cys Ser Ala Gly Val Ile Ala Val Asp
                245                 250                 255

Leu Ala Lys Asp Met Leu Leu Val His Arg Asn Thr Tyr Ala Val Val
            260                 265                 270

Val Ser Thr Glu Asn Ile Thr Gln Asn Trp Tyr Phe Gly Asn Lys Lys
        275                 280                 285

Ser Met Leu Ile Pro Asn Cys Leu Phe Arg Val Gly Gly Ser Ala Val
    290                 295                 300

Leu Leu Ser Asn Lys Ser Arg Asp Lys Arg Arg Ser Lys Tyr Arg Leu
305                 310                 315                 320

Val His Val Val Arg Thr His Arg Gly Ala Asp Asp Lys Ala Phe Arg
                325                 330                 335

Cys Val Tyr Gln Glu Gln Asp Asp Thr Gly Arg Thr Gly Val Ser Leu
            340                 345                 350

Ser Lys Asp Leu Met Ala Ile Ala Gly Glu Thr Leu Lys Thr Asn Ile
        355                 360                 365

Thr Thr Leu Gly Pro Leu Val Leu Pro Ile Ser Glu Gln Ile Leu Phe
    370                 375                 380

Phe Met Thr Leu Val Val Lys Lys Leu Phe Asn Gly Lys Val Lys Pro
385                 390                 395                 400

Tyr Ile Pro Asp Phe Lys Leu Ala Phe Glu His Phe Cys Ile His Ala
                405                 410                 415

Gly Gly Arg Ala Val Ile Asp Glu Leu Glu Lys Asn Leu Gln Leu Ser
            420                 425                 430

Pro Val His Val Glu Ala Ser Arg Met Thr Leu His Arg Phe Gly Asn
        435                 440                 445

Thr Ser Ser Ser Ser Ile Trp Tyr Glu Leu Ala Tyr Ile Glu Ala Lys
    450                 455                 460

Gly Arg Met Arg Arg Gly Asn Arg Val Trp Gln Ile Ala Phe Gly Ser
465                 470                 475                 480

Gly Phe Lys Cys Asn Ser Ala Ile Trp Glu Ala Leu Arg His Val Lys
                485                 490                 495

Pro Ser Asn Asn Ser Pro Trp Glu Asp Cys Ile Asp Lys Tyr Pro Val
            500                 505                 510

Thr Leu Ser Tyr
        515
```

<210> SEQ ID NO 43
<211> LENGTH: 639
<212> TYPE: DNA
<213> ORGANISM: Arabidopsis thaliana

<400> SEQUENCE: 43

```
atgtcgagag ctttgtcagt cgtttgtgtc ttgctcgcca tatccttcgt ctgtgcacgt     60

gctcgtcagg tgccgggaga gtctgatgag ggaaagacga cgggacatga cgatacaaca    120

acaatgccca tgcatgcaaa agcagctgat cagttaccac caaagagcgt cggcgacaaa    180

aaatgcatcg gaggagttgc tggagtcggt ggattcgccg gagttggtgg tgttgccggc    240

gtgggaggtc tagggatgcc actcatcggt ggtcttggcg ggatcggtaa gtatggtggc    300
```

```
ataggcggtg cagctggaat cggtggattt catagtatag gcggtgttgg cggtctaggc    360

ggtgtcggag gaggtgttgg cggtctaggc ggtgttggag ggggtgttgg tggtctaggt    420

ggcgttggcg gtctaggtgg agctggttta ggcggtgtag gtggtgttgg cggtggtatt    480

ggtaaagccg gtggtattgg cggtttaggt ggtctaggcg gagccggagg tggtttaggt    540

ggagttggtg gtctcggtaa ggctggtggt attggtgttg gtggtggtat cggtggtgga    600

cacggcgtgg tcggtggtgt gatcgatcca catccttaa                           639
```

<210> SEQ ID NO 44
<211> LENGTH: 212
<212> TYPE: PRT
<213> ORGANISM: Arabidopsis thaliana

<400> SEQUENCE: 44

```
Met Ser Arg Ala Leu Ser Val Val Cys Val Leu Leu Ala Ile Ser Phe
1               5                   10                  15

Val Cys Ala Arg Ala Arg Gln Val Pro Gly Glu Ser Asp Glu Gly Lys
            20                  25                  30

Thr Thr Gly His Asp Asp Thr Thr Thr Met Pro Met His Ala Lys Ala
        35                  40                  45

Ala Asp Gln Leu Pro Pro Lys Ser Val Gly Asp Lys Lys Cys Ile Gly
    50                  55                  60

Gly Val Ala Gly Val Gly Gly Phe Ala Gly Val Gly Gly Val Ala Gly
65                  70                  75                  80

Val Gly Gly Leu Gly Met Pro Leu Ile Gly Gly Leu Gly Gly Ile Gly
                85                  90                  95

Lys Tyr Gly Gly Ile Gly Gly Ala Ala Gly Ile Gly Gly Phe His Ser
            100                 105                 110

Ile Gly Gly Val Gly Gly Leu Gly Gly Val Gly Gly Gly Val Gly Gly
        115                 120                 125

Leu Gly Gly Val Gly Gly Gly Val Gly Gly Leu Gly Gly Val Gly Gly
    130                 135                 140

Leu Gly Gly Ala Gly Leu Gly Gly Val Gly Gly Val Gly Gly Gly Ile
145                 150                 155                 160

Gly Lys Ala Gly Gly Ile Gly Gly Leu Gly Gly Leu Gly Gly Ala Gly
                165                 170                 175

Gly Gly Leu Gly Gly Val Gly Gly Leu Gly Lys Ala Gly Gly Ile Gly
            180                 185                 190

Val Gly Gly Gly Ile Gly Gly Gly His Gly Val Val Gly Gly Val Ile
        195                 200                 205

Asp Pro His Pro
    210
```

<210> SEQ ID NO 45
<211> LENGTH: 684
<212> TYPE: DNA
<213> ORGANISM: Arabidopsis thaliana

<400> SEQUENCE: 45

```
atggcaagca gcgacgtgaa gctgatcggt gcatgggcga gtccctttgt gatgaggccg     60

aggattgctc taaacctcaa gtctgtcccc tacgagttcc tccaagagac gtttgggtct    120

aagagcgagt tgcttcttaa atcaaacccg gttcacaaga agatcccggt tctgcttcat    180

gctgataaac cggtgagtga gtccaacatc atcgttgagt atatcgatga cacttggagc    240

tcatctggac cgtccattct cccttccgat ccttacgatc gggccatggc tcggttctgg    300
```

gctgcttaca tcgacgaaaa gtggtttgtc gctctaagag gtttcctaaa agccggagga 360
gaagaagaga agaaagctgt gatagctcaa ctagaagaag ggaatgcgtt tctggagaag 420
gcgttcattg attgcagcaa aggaaaaccg ttcttcaacg gtgacaacat cggttacctc 480
gacattgctc tcgggtgctt cttggcttgg ttgagagtca ccgagttagc agtcagctat 540
aaaattcttg atgaggccaa gacaccttct ttgtccaaat gggctgagaa tttctgtaat 600
gatcccgctg taaaacctgt catgcccgag actgcaaagc ttgctgaatt cgcaaagaag 660
atctttccta agccgcaggc ctaa 684

<210> SEQ ID NO 46
<211> LENGTH: 227
<212> TYPE: PRT
<213> ORGANISM: Arabidopsis thaliana

<400> SEQUENCE: 46

Met Ala Ser Ser Asp Val Lys Leu Ile Gly Ala Trp Ala Ser Pro Phe
1 5 10 15

Val Met Arg Pro Arg Ile Ala Leu Asn Leu Lys Ser Val Pro Tyr Glu
20 25 30

Phe Leu Gln Glu Thr Phe Gly Ser Lys Ser Glu Leu Leu Leu Lys Ser
35 40 45

Asn Pro Val His Lys Lys Ile Pro Val Leu Leu His Ala Asp Lys Pro
50 55 60

Val Ser Glu Ser Asn Ile Ile Val Glu Tyr Ile Asp Asp Thr Trp Ser
65 70 75 80

Ser Ser Gly Pro Ser Ile Leu Pro Ser Asp Pro Tyr Asp Arg Ala Met
85 90 95

Ala Arg Phe Trp Ala Ala Tyr Ile Asp Glu Lys Trp Phe Val Ala Leu
100 105 110

Arg Gly Phe Leu Lys Ala Gly Gly Glu Glu Glu Lys Lys Ala Val Ile
115 120 125

Ala Gln Leu Glu Glu Gly Asn Ala Phe Leu Glu Lys Ala Phe Ile Asp
130 135 140

Cys Ser Lys Gly Lys Pro Phe Phe Asn Gly Asp Asn Ile Gly Tyr Leu
145 150 155 160

Asp Ile Ala Leu Gly Cys Phe Leu Ala Trp Leu Arg Val Thr Glu Leu
165 170 175

Ala Val Ser Tyr Lys Ile Leu Asp Glu Ala Lys Thr Pro Ser Leu Ser
180 185 190

Lys Trp Ala Glu Asn Phe Cys Asn Asp Pro Ala Val Lys Pro Val Met
195 200 205

Pro Glu Thr Ala Lys Leu Ala Glu Phe Ala Lys Lys Ile Phe Pro Lys
210 215 220

Pro Gln Ala
225

<210> SEQ ID NO 47
<211> LENGTH: 279
<212> TYPE: DNA
<213> ORGANISM: Arabidopsis thaliana

<400> SEQUENCE: 47
atggcgtctc aacaagagaa gaagcagctg gatgagaggg caaagaaggg cgagaccgtc 60
gtgccaggtg gtacgggagg caaaagcttc gaagctcaac agcatctcgc tgaagggagg 120
agccgaggag ggcaaactcg aaaggagcag ttaggaactg aaggatatca gcagatggga 180
cgcaaaggtg gtcttagcac cggagacaag cctggtgggg aacacgctga ggaggaagga 240
gtcgagatag acgaatccaa attcaggacc aagacctaa 279

<210> SEQ ID NO 48
<211> LENGTH: 92
<212> TYPE: PRT
<213> ORGANISM: Arabidopsis thaliana

<400> SEQUENCE: 48

Met Ala Ser Gln Gln Glu Lys Lys Gln Leu Asp Glu Arg Ala Lys Lys
1 5 10 15

Gly Glu Thr Val Val Pro Gly Gly Thr Gly Gly Lys Ser Phe Glu Ala
20 25 30

Gln Gln His Leu Ala Glu Gly Arg Ser Arg Gly Gly Gln Thr Arg Lys
35 40 45

Glu Gln Leu Gly Thr Glu Gly Tyr Gln Gln Met Gly Arg Lys Gly Gly
50 55 60

Leu Ser Thr Gly Asp Lys Pro Gly Gly Glu His Ala Glu Glu Glu Gly
65 70 75 80

Val Glu Ile Asp Glu Ser Lys Phe Arg Thr Lys Thr
85 90

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 49
atggcgcgcc cgacatgaag cgacgttgaa cg 32

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 50
gcttaattaa ctttccgcag ccttcaggcc gc 32

<210> SEQ ID NO 51
<211> LENGTH: 1131
<212> TYPE: DNA
<213> ORGANISM: Arabidopsis thaliana

<400> SEQUENCE: 51
atggctcctt caacaaaagt tctctcttta cttctcttat atggcgtcgt gtcattagcc 60
tccggtgatg agtccatcat caacgaccat ctccaacttc catcggacgg caagtggaga 120
accgatgaag aagtgaggtc catctactta caatggtccg cagaacacgg gaaaactaac 180
aacaacaaca acggtatcat caacgaccaa gacaaaagat tcaatatttt caaagacaac 240
ttaagattca tcgatctaca caacgaaaac aacaagaacg ctacttacaa gcttggtctc 300
accaaattta ccgatctcac taacgatgag taccgcaagt tgtacctcgg ggcaagaact 360
gagcccgccc gccgcatcgc taaggccaag aatgtcaacc agaaatactc agccgctgta 420
aacggcaagg aggttccaga gacggttgat tggagacaga aaggagccgt taaccccatc 480

```
aaagaccaag gaacttgcgg aagttgttgg gcgttttcga ctactgcagc agtagaaggt    540

ataaacaaga tcgtaacagg agaactcata tctctatcag aacaagaact tgttgactgc    600

gacaaatcct acaatcaagg ttgcaacggc ggtttaatgg actacgcttt tcaattcatc    660

atgaaaaatg gtggcttaaa cactgagaaa gattatcctt accgtggatt cggcggaaaa    720

tgcaattctt tcttgaagaa ttctagagtt gtgagtattg atgggtacga agatgttcct    780

actaaagacg agactgcgtt gaagaaagct atttcatacc aaccggttag tgtagctatt    840

gaagccggtg gaagaatttt tcaacattac caatcgggta tttttaccgg aagttgtggt    900

acaaatcttg atcacgcggt agttgctgtc gggtacggat cagagaacgg tgttgactac    960

tggattgtaa ggaactcttg gggtccacgt tggggtgagg aaggttacat tagaatggag   1020

agaaacttgg cagcctccaa atccggtaag tgtgggattg cggttgaagc ctcgtacccg   1080

gttaagtaca gcccaaaccc ggttcgtgga aatactatca gcagtgtttg a            1131


<210> SEQ ID NO 52
<211> LENGTH: 376
<212> TYPE: PRT
<213> ORGANISM: Arabidopsis thaliana

<400> SEQUENCE: 52

Met Ala Pro Ser Thr Lys Val Leu Ser Leu Leu Leu Leu Tyr Gly Val
1               5                   10                  15

Val Ser Leu Ala Ser Gly Asp Glu Ser Ile Ile Asn Asp His Leu Gln
            20                  25                  30

Leu Pro Ser Asp Gly Lys Trp Arg Thr Asp Glu Glu Val Arg Ser Ile
        35                  40                  45

Tyr Leu Gln Trp Ser Ala Glu His Gly Lys Thr Asn Asn Asn Asn Asn
    50                  55                  60

Gly Ile Ile Asn Asp Gln Asp Lys Arg Phe Asn Ile Phe Lys Asp Asn
65                  70                  75                  80

Leu Arg Phe Ile Asp Leu His Asn Glu Asn Asn Lys Asn Ala Thr Tyr
                85                  90                  95

Lys Leu Gly Leu Thr Lys Phe Thr Asp Leu Thr Asn Asp Glu Tyr Arg
            100                 105                 110

Lys Leu Tyr Leu Gly Ala Arg Thr Glu Pro Ala Arg Arg Ile Ala Lys
        115                 120                 125

Ala Lys Asn Val Asn Gln Lys Tyr Ser Ala Ala Val Asn Gly Lys Glu
    130                 135                 140

Val Pro Glu Thr Val Asp Trp Arg Gln Lys Gly Ala Val Asn Pro Ile
145                 150                 155                 160

Lys Asp Gln Gly Thr Cys Gly Ser Cys Trp Ala Phe Ser Thr Thr Ala
                165                 170                 175

Ala Val Glu Gly Ile Asn Lys Ile Val Thr Gly Glu Leu Ile Ser Leu
            180                 185                 190

Ser Glu Gln Glu Leu Val Asp Cys Asp Lys Ser Tyr Asn Gln Gly Cys
        195                 200                 205

Asn Gly Gly Leu Met Asp Tyr Ala Phe Gln Phe Ile Met Lys Asn Gly
    210                 215                 220

Gly Leu Asn Thr Glu Lys Asp Tyr Pro Tyr Arg Gly Phe Gly Gly Lys
225                 230                 235                 240

Cys Asn Ser Phe Leu Lys Asn Ser Arg Val Val Ser Ile Asp Gly Tyr
                245                 250                 255

Glu Asp Val Pro Thr Lys Asp Glu Thr Ala Leu Lys Lys Ala Ile Ser
            260                 265                 270
```

```
Tyr Gln Pro Val Ser Val Ala Ile Glu Ala Gly Gly Arg Ile Phe Gln
        275                 280                 285

His Tyr Gln Ser Gly Ile Phe Thr Gly Ser Cys Gly Thr Asn Leu Asp
    290                 295                 300

His Ala Val Val Ala Val Gly Tyr Gly Ser Glu Asn Gly Val Asp Tyr
305                 310                 315                 320

Trp Ile Val Arg Asn Ser Trp Gly Pro Arg Trp Gly Glu Glu Gly Tyr
                325                 330                 335

Ile Arg Met Glu Arg Asn Leu Ala Ala Ser Lys Ser Gly Lys Cys Gly
            340                 345                 350

Ile Ala Val Glu Ala Ser Tyr Pro Val Lys Tyr Ser Pro Asn Pro Val
        355                 360                 365

Arg Gly Asn Thr Ile Ser Ser Val
    370                 375


<210> SEQ ID NO 53
<211> LENGTH: 1653
<212> TYPE: DNA
<213> ORGANISM: Arabidopsis thaliana

<400> SEQUENCE: 53

atgcggtgct ttccacctcc cttatggtgc acctccttgg tcgttttctt gtcggttacc     60

ggagccctag ccgccgatcc ctacgtcttc ttcgattgga ctgtctctta cctctctgct    120

tctcctctcg gcactcgtca acaggtaatt gggataaatg ggcaatttcc tggtccgatt    180

ctaaacgtaa ctacgaattg gaatgttgtt atgaatgtga agaataatct tgatgagcca    240

ttgcttctta catggaatgg aatccaacat aggaaaaact catggcaaga tggtgttttg    300

ggaactaatt gtccaattcc ttctggttgg aattggactt atgagtttca agttaaagat    360

cagattggta gtttctttta ttttccttct acaaattttc aaagagcttc tggtggttat    420

ggagggatta ttgtcaataa tcgcgctatc attccggttc ctttcgctct tcctgatggt    480

gatgttactc tctttatcag tgattggtat actaagagcc ataagaagct gaggaaggat    540

gttgagagta agaacggcct tcgacctccg gatggtattg tcatcaatgg atttggacct    600

tttgcttcta atggtagtcc ttttgggacc ataaacgttg aaccaggacg aacatatcgt    660

tttcgtgttc acaatagtgg cattgcgacc agcttgaatt tcagaataca gaatcataac    720

ctgcttcttg ttgagacaga agggtcatac acaattcagc agaattatac gaatatggat    780

atacatgtgg gtcaatcttt ctcatttctg gtcactatgg atcagtctgg tagtaatgac    840

tactacattg ttgccagccc aaggtttgct acatccatca aagctagtgg agtcgctgtc    900

ttgcgctact ctaattccca aggacccgct tcaggtccac tccctgatcc tcctattgag    960

ttggacacat tttctcaat gaaccaagca cgatccttaa ggttgaattt gtcatctgga    1020

gctgcccgtc caaacccgca gggatctttc aaatatggcc agattacagt aactgatgtg   1080

tatgtgattg tcaaccgacc accagagatg atagagggac gattgcgtgc aactcttaat   1140

ggtatatcat acttacctcc tgcaacaccc ctaaagcttg ctcagcaata caacatctca   1200

ggggtataca agttggattt cccaaaaagg ccaatgaata ggcaccccag ggttgatacc   1260

tcagtcataa acggcacgtt caagggattc gtggaaatca tatttcaaaa tagtgacacc   1320

actgttaaga gctaccactt ggatggttat gcatttttg ttgttgggat ggactttggt    1380

ctgtggacag aaaatagcag aagcacatac aacaagggtg atgcagttgc tcgatctact   1440

acgcaggtgt ttcctggtgc atggacggcc gtcttggttt ctttggacaa tgctggcatg   1500
```

```
tggaaccttc gaatagacaa tctagcctca tggtatcttg gccaagaact atacttgagt   1560

gtggttaatc cagagattga cattgactca tctgagaatt ccgttcctaa aaactctata   1620

tattgtggtc ggctctcacc attacaaaag taa                                1653


<210> SEQ ID NO 54
<211> LENGTH: 550
<212> TYPE: PRT
<213> ORGANISM: Arabidopsis thaliana

<400> SEQUENCE: 54

Met Arg Cys Phe Pro Pro Pro Leu Trp Cys Thr Ser Leu Val Val Phe
1               5                   10                  15

Leu Ser Val Thr Gly Ala Leu Ala Ala Asp Pro Tyr Val Phe Phe Asp
            20                  25                  30

Trp Thr Val Ser Tyr Leu Ser Ala Ser Pro Leu Gly Thr Arg Gln Gln
        35                  40                  45

Val Ile Gly Ile Asn Gly Gln Phe Pro Gly Pro Ile Leu Asn Val Thr
    50                  55                  60

Thr Asn Trp Asn Val Val Met Asn Val Lys Asn Asn Leu Asp Glu Pro
65                  70                  75                  80

Leu Leu Leu Thr Trp Asn Gly Ile Gln His Arg Lys Asn Ser Trp Gln
                85                  90                  95

Asp Gly Val Leu Gly Thr Asn Cys Pro Ile Pro Ser Gly Trp Asn Trp
            100                 105                 110

Thr Tyr Glu Phe Gln Val Lys Asp Gln Ile Gly Ser Phe Phe Tyr Phe
        115                 120                 125

Pro Ser Thr Asn Phe Gln Arg Ala Ser Gly Gly Tyr Gly Gly Ile Ile
    130                 135                 140

Val Asn Asn Arg Ala Ile Ile Pro Val Pro Phe Ala Leu Pro Asp Gly
145                 150                 155                 160

Asp Val Thr Leu Phe Ile Ser Asp Trp Tyr Thr Lys Ser His Lys Lys
                165                 170                 175

Leu Arg Lys Asp Val Glu Ser Lys Asn Gly Leu Arg Pro Pro Asp Gly
            180                 185                 190

Ile Val Ile Asn Gly Phe Gly Pro Phe Ala Ser Asn Gly Ser Pro Phe
        195                 200                 205

Gly Thr Ile Asn Val Glu Pro Gly Arg Thr Tyr Arg Phe Arg Val His
    210                 215                 220

Asn Ser Gly Ile Ala Thr Ser Leu Asn Phe Arg Ile Gln Asn His Asn
225                 230                 235                 240

Leu Leu Leu Val Glu Thr Glu Gly Ser Tyr Thr Ile Gln Gln Asn Tyr
                245                 250                 255

Thr Asn Met Asp Ile His Val Gly Gln Ser Phe Ser Phe Leu Val Thr
            260                 265                 270

Met Asp Gln Ser Gly Ser Asn Asp Tyr Tyr Ile Val Ala Ser Pro Arg
        275                 280                 285

Phe Ala Thr Ser Ile Lys Ala Ser Gly Val Ala Val Leu Arg Tyr Ser
    290                 295                 300

Asn Ser Gln Gly Pro Ala Ser Gly Pro Leu Pro Asp Pro Pro Ile Glu
305                 310                 315                 320

Leu Asp Thr Phe Phe Ser Met Asn Gln Ala Arg Ser Leu Arg Leu Asn
                325                 330                 335

Leu Ser Ser Gly Ala Ala Arg Pro Asn Pro Gln Gly Ser Phe Lys Tyr
            340                 345                 350
```

```
Gly Gln Ile Thr Val Thr Asp Val Tyr Val Ile Val Asn Arg Pro Pro
        355                 360                 365

Glu Met Ile Glu Gly Arg Leu Arg Ala Thr Leu Asn Gly Ile Ser Tyr
    370                 375                 380

Leu Pro Pro Ala Thr Pro Leu Lys Leu Ala Gln Gln Tyr Asn Ile Ser
385                 390                 395                 400

Gly Val Tyr Lys Leu Asp Phe Pro Lys Arg Pro Met Asn Arg His Pro
                405                 410                 415

Arg Val Asp Thr Ser Val Ile Asn Gly Thr Phe Lys Gly Phe Val Glu
            420                 425                 430

Ile Ile Phe Gln Asn Ser Asp Thr Thr Val Lys Ser Tyr His Leu Asp
        435                 440                 445

Gly Tyr Ala Phe Phe Val Val Gly Met Asp Phe Gly Leu Trp Thr Glu
    450                 455                 460

Asn Ser Arg Ser Thr Tyr Asn Lys Gly Asp Ala Val Ala Arg Ser Thr
465                 470                 475                 480

Thr Gln Val Phe Pro Gly Ala Trp Thr Ala Val Leu Val Ser Leu Asp
                485                 490                 495

Asn Ala Gly Met Trp Asn Leu Arg Ile Asp Asn Leu Ala Ser Trp Tyr
            500                 505                 510

Leu Gly Gln Glu Leu Tyr Leu Ser Val Val Asn Pro Glu Ile Asp Ile
        515                 520                 525

Asp Ser Ser Glu Asn Ser Val Pro Lys Asn Ser Ile Tyr Cys Gly Arg
    530                 535                 540

Leu Ser Pro Leu Gln Lys
545                 550


<210> SEQ ID NO 55
<211> LENGTH: 615
<212> TYPE: DNA
<213> ORGANISM: Arabidopsis thaliana

<400> SEQUENCE: 55

atgcttctaa ttctagcgat ttggtcacca atttcacact cgcttcactt cgatctacac      60

tcaggtcgca caaagtgtat cgccgaagac atcaaaagca attcaatgac tgttggtaaa     120

tacaacatcg ataatcctca cgaaggtcaa gctttaccac aaactcacaa aatttccgtc     180

aaggtgacgt ctaattccgg taacaattac catcacgcgg aacaagtaga ttcaggacaa     240

ttcgcattct cggctgttga agcaggtgat tacatggctt gtttcactgc tgttgatcat     300

aagcctgagg tttcgttgag tattgacttt gagtggaaga ctggtgttca atctaaaagc     360

tgggctaatg ttgctaagaa gagtcaagtc gaagttatgg aatttgaagt aaagagtctt     420

cttgatactg ttaactcgat tcatgaagag atgtattatc ttagagatag ggaagaagag     480

atgcaagact tgaaccggtc cactaacaca aaaatggcgt ggttgagtgt tctctcgttt     540

ttcgtctgca taggagttgc agggatgcag tttttgcact tgaagacgtt tttcgagaag     600

aagaaggtta tctga                                                      615


<210> SEQ ID NO 56
<211> LENGTH: 204
<212> TYPE: PRT
<213> ORGANISM: Arabidopsis thaliana

<400> SEQUENCE: 56

Met Leu Leu Ile Leu Ala Ile Trp Ser Pro Ile Ser His Ser Leu His
1               5                   10                  15
```

```
Phe Asp Leu His Ser Gly Arg Thr Lys Cys Ile Ala Glu Asp Ile Lys
            20                  25                  30

Ser Asn Ser Met Thr Val Gly Lys Tyr Asn Ile Asp Asn Pro His Glu
        35                  40                  45

Gly Gln Ala Leu Pro Gln Thr His Lys Ile Ser Val Lys Val Thr Ser
    50                  55                  60

Asn Ser Gly Asn Asn Tyr His His Ala Glu Gln Val Asp Ser Gly Gln
65                  70                  75                  80

Phe Ala Phe Ser Ala Val Glu Ala Gly Asp Tyr Met Ala Cys Phe Thr
                85                  90                  95

Ala Val Asp His Lys Pro Glu Val Ser Leu Ser Ile Asp Phe Glu Trp
            100                 105                 110

Lys Thr Gly Val Gln Ser Lys Ser Trp Ala Asn Val Ala Lys Lys Ser
        115                 120                 125

Gln Val Glu Val Met Glu Phe Glu Val Lys Ser Leu Leu Asp Thr Val
    130                 135                 140

Asn Ser Ile His Glu Glu Met Tyr Tyr Leu Arg Asp Arg Glu Glu Glu
145                 150                 155                 160

Met Gln Asp Leu Asn Arg Ser Thr Asn Thr Lys Met Ala Trp Leu Ser
                165                 170                 175

Val Leu Ser Phe Phe Val Cys Ile Gly Val Ala Gly Met Gln Phe Leu
            180                 185                 190

His Leu Lys Thr Phe Phe Glu Lys Lys Lys Val Ile
        195                 200
```

<210> SEQ ID NO 57
<211> LENGTH: 969
<212> TYPE: DNA
<213> ORGANISM: Arabidopsis thaliana

<400> SEQUENCE: 57

```
atggcacatg ccacgtttac gtcggaaggg cagaatatgg agtcgtttcg actcttgagt      60

ggccacaaaa tcccagccgt tggactcggc acgtggcgat ctgggtctca agccgcccac     120

gccgttgtca ctgcaatcgt cgagggtggc tataggcaca tagatacagc ttgggagtat     180

ggtgatcaga gagaggtcgg tcaaggaata aagagggcga tgcacgctgg ccttgaaagg     240

agggacctct ttgtgacctc gaagctttgg tgcactgagt tatctcctga gagagtgcgt     300

cctgctctgc aaaacaccct taaagagctt caattagagt accttgatct ctacttgatt     360

cactggccta tccggctaag agaaggagcc agtaagccac caaaggcagg ggacgttctt     420

gactttgaca tggaaggagt ttggagagaa atggagaatc tttccaagga cagtctcgtc     480

aggaatatcg gtgtctgtaa ctttacagtc actaagctca ataagctgct aggatttgct     540

gaactgatcc ctgccgtttg ccagatggaa atgcatcctg gttggagaaa cgataggata     600

ctcgaattct gcaagaagaa tgagatccat gttactgcct attctccatt gggatctcaa     660

gaaggcggga gagatctgat acacgatcag acggtggata ggatagcgaa gaagctgaat     720

aagacaccgg gacagattct agtgaaatgg ggtttgcaga gaggaacaag tgtcatccct     780

aagtcattga atccagagag gatcaaagag aacatcaaag tgtttgattg ggtgatccct     840

gaacaagact tccaagctct caacagcatc actgaccaga aacgagtgat agacggtgag     900

gatcttttcg tcaacaagac cgaaggtcca ttccgtagtg tggctgatct atgggaccat     960

gaagactaa                                                             969
```

<210> SEQ ID NO 58

<211> LENGTH: 322
<212> TYPE: PRT
<213> ORGANISM: Arabidopsis thaliana

<400> SEQUENCE: 58

```
Met Ala His Ala Thr Phe Thr Ser Glu Gly Gln Asn Met Glu Ser Phe
1               5                   10                  15

Arg Leu Leu Ser Gly His Lys Ile Pro Ala Val Gly Leu Gly Thr Trp
            20                  25                  30

Arg Ser Gly Ser Gln Ala Ala His Ala Val Val Thr Ala Ile Val Glu
        35                  40                  45

Gly Gly Tyr Arg His Ile Asp Thr Ala Trp Glu Tyr Gly Asp Gln Arg
    50                  55                  60

Glu Val Gly Gln Gly Ile Lys Arg Ala Met His Ala Gly Leu Glu Arg
65                  70                  75                  80

Arg Asp Leu Phe Val Thr Ser Lys Leu Trp Cys Thr Glu Leu Ser Pro
                85                  90                  95

Glu Arg Val Arg Pro Ala Leu Gln Asn Thr Leu Lys Glu Leu Gln Leu
            100                 105                 110

Glu Tyr Leu Asp Leu Tyr Leu Ile His Trp Pro Ile Arg Leu Arg Glu
        115                 120                 125

Gly Ala Ser Lys Pro Pro Lys Ala Gly Asp Val Leu Asp Phe Asp Met
    130                 135                 140

Glu Gly Val Trp Arg Glu Met Glu Asn Leu Ser Lys Asp Ser Leu Val
145                 150                 155                 160

Arg Asn Ile Gly Val Cys Asn Phe Thr Val Thr Lys Leu Asn Lys Leu
                165                 170                 175

Leu Gly Phe Ala Glu Leu Ile Pro Ala Val Cys Gln Met Glu Met His
            180                 185                 190

Pro Gly Trp Arg Asn Asp Arg Ile Leu Glu Phe Cys Lys Lys Asn Glu
        195                 200                 205

Ile His Val Thr Ala Tyr Ser Pro Leu Gly Ser Gln Glu Gly Gly Arg
    210                 215                 220

Asp Leu Ile His Asp Gln Thr Val Asp Arg Ile Ala Lys Lys Leu Asn
225                 230                 235                 240

Lys Thr Pro Gly Gln Ile Leu Val Lys Trp Gly Leu Gln Arg Gly Thr
                245                 250                 255

Ser Val Ile Pro Lys Ser Leu Asn Pro Glu Arg Ile Lys Glu Asn Ile
            260                 265                 270

Lys Val Phe Asp Trp Val Ile Pro Glu Gln Asp Phe Gln Ala Leu Asn
        275                 280                 285

Ser Ile Thr Asp Gln Lys Arg Val Ile Asp Gly Glu Asp Leu Phe Val
    290                 295                 300

Asn Lys Thr Glu Gly Pro Phe Arg Ser Val Ala Asp Leu Trp Asp His
305                 310                 315                 320

Glu Asp
```

<210> SEQ ID NO 59
<211> LENGTH: 867
<212> TYPE: DNA
<213> ORGANISM: Arabidopsis thaliana

<400> SEQUENCE: 59

```
atggcgtctg agaaacaaaa acaacatgca caacctggca aagaacatgt catggaatca      60

agcccacaat tctctagctc agattaccaa ccttccaaca agcttcgtgg taaggtggcg     120
```

```
ttgataactg gtggagactc tgggattggt cgagccgtgg gatactgttt tgcatccgaa    180

ggagctactg tggctttcac ttacgtgaag ggtcaagaag aaaaagatgc acaagagacc    240

ctacaaatgt tgaaggaggt caaaacctcg gactccaagg aacctatcgc cattccaacg    300

gatttaggat ttgacgaaaa ctgcaaaagg gtcgttgatg aggtcgttaa tgcttttggc    360

cgcatcgatg ttttgatcaa taacgcagca gagcagtacg agagcagcac aatcgaagag    420

attgatgagc ctaggcttga gcgagtcttc cgtacaaaca tcttttctta cttctttctc    480

acaaggcatg cgttgaagca tatgaaggaa ggaagcagca ttatcaacac cacttcggtg    540

aatgcctaca agggaaacgc ttcacttctc gactacaccg ctacaaaagg agcgattgtg    600

gcgtttactc gaggacttgc acttcagcta gctgagaaag gaatccgtgt caatggtgtg    660

gctcctggtc caatatggac acccccttatc ccagcatcat tcaatgagga gaagattaag    720

aattttgggt ctgaggttcc gatgaaaaga gcgggtcagc caattgaagt ggcaccatcc    780

tatgttttct tggcgtgtaa ccactgctct tcttacttca ctggtcaagt tcttcaccct    840

aatggaggag ctgtggtaaa tgcgtaa                                        867


<210> SEQ ID NO 60
<211> LENGTH: 288
<212> TYPE: PRT
<213> ORGANISM: Arabidopsis thaliana

<400> SEQUENCE: 60

Met Ala Ser Glu Lys Gln Lys Gln His Ala Gln Pro Gly Lys Glu His
1               5                   10                  15

Val Met Glu Ser Ser Pro Gln Phe Ser Ser Ser Asp Tyr Gln Pro Ser
            20                  25                  30

Asn Lys Leu Arg Gly Lys Val Ala Leu Ile Thr Gly Gly Asp Ser Gly
        35                  40                  45

Ile Gly Arg Ala Val Gly Tyr Cys Phe Ala Ser Glu Gly Ala Thr Val
    50                  55                  60

Ala Phe Thr Tyr Val Lys Gly Gln Glu Glu Lys Asp Ala Gln Glu Thr
65                  70                  75                  80

Leu Gln Met Leu Lys Glu Val Lys Thr Ser Asp Ser Lys Glu Pro Ile
                85                  90                  95

Ala Ile Pro Thr Asp Leu Gly Phe Asp Glu Asn Cys Lys Arg Val Val
            100                 105                 110

Asp Glu Val Val Asn Ala Phe Gly Arg Ile Asp Val Leu Ile Asn Asn
        115                 120                 125

Ala Ala Glu Gln Tyr Glu Ser Ser Thr Ile Glu Glu Ile Asp Glu Pro
    130                 135                 140

Arg Leu Glu Arg Val Phe Arg Thr Asn Ile Phe Ser Tyr Phe Phe Leu
145                 150                 155                 160

Thr Arg His Ala Leu Lys His Met Lys Glu Gly Ser Ser Ile Ile Asn
                165                 170                 175

Thr Thr Ser Val Asn Ala Tyr Lys Gly Asn Ala Ser Leu Leu Asp Tyr
            180                 185                 190

Thr Ala Thr Lys Gly Ala Ile Val Ala Phe Thr Arg Gly Leu Ala Leu
        195                 200                 205

Gln Leu Ala Glu Lys Gly Ile Arg Val Asn Gly Val Ala Pro Gly Pro
    210                 215                 220

Ile Trp Thr Pro Leu Ile Pro Ala Ser Phe Asn Glu Glu Lys Ile Lys
225                 230                 235                 240

Asn Phe Gly Ser Glu Val Pro Met Lys Arg Ala Gly Gln Pro Ile Glu
```

```
                245                 250                 255

Val Ala Pro Ser Tyr Val Phe Leu Ala Cys Asn His Cys Ser Ser Tyr
            260                 265                 270

Phe Thr Gly Gln Val Leu His Pro Asn Gly Gly Ala Val Val Asn Ala
        275                 280                 285


<210> SEQ ID NO 61
<211> LENGTH: 1326
<212> TYPE: DNA
<213> ORGANISM: Arabidopsis thaliana

<400> SEQUENCE: 61

atggattcaa cgaagcttag tgagctaaag gtcttcatcg atcaatgcaa gtctgaccct      60

tcccttctca ctactccttc actctccttc ttccgtgact atctcgagag tcttggtgct     120

aagataccta ctggtgtcca tgaagaagac aaagacacta agccgaggag tttcgtagtg     180

gaagagagtg atgatgatat ggatgaaact gaagaagtaa aaccgaaagt ggaggaagaa     240

gaagaagagg atgagattgt tgaatctgat gtagagcttg aaggagacac tgttgagcct     300

gataatgatc ctcctcagaa gatgggggat tcatcagtgg aggtgactga tgagaatcgt     360

gaagctgctc aagaagctaa gggcaaagcc atggaggccc tttctgaagg aaactttgat     420

gaagcaattg agcatttaac tcgggcaata acgttgaacc cgacttcagc tattatgtat     480

ggaaacagag ctagtgtcta cattaagttg aagaagccaa acgctgctat tcgagatgca     540

aacgcagcat tggagattaa ccctgattct gccaagggat acaagtcacg aggtatggct     600

cgtgccatgc ttggagaatg ggcagaggct gcaaaagacc ttcaccttgc atctacgata     660

gactatgatg aggaaattag tgctgttctc aaaaaggttg aacctaatgc acataagctt     720

gaggagcacc gtagaaagta tgacagatta cgtaaggaaa gagaggacaa aaaggctgaa     780

cgggatagat tacgtcgccg tgctgaagca caggctgcct atgataaagc taagaaagaa     840

gaacagtcat catctagcag accatcagga ggcggtttcc caggaggtat gcccggtggt     900

ttcccaggag gtatgcccgg tggattccca ggaggaatgg gaggcatgcc cggcggattc     960

ccgggaggaa tgggtggtat gggcggtatg cccggtggat tcccaggagg aatgggcggt    1020

ggtatgcctg caggaatggg cggtggtatg cccggaatgg gcggtggtat gcctgctgga    1080

atgggtggtg gcggtatgcc aggtgcaggc ggtggtatgc ctggtggtgg cggtatgcct    1140

ggtggtatgg acttcagcaa aatattgaat gatcctgagc taatgacggc atttagcgac    1200

cctgaagtca tggctgctct tcaagatgtg atgaagaacc ctgcgaatct agcgaagcat    1260

caggcgaatc cgaaggtggc tcccgtgatt gcaaagatga tgggcaaatt tgcaggacct    1320

cagtaa                                                               1326


<210> SEQ ID NO 62
<211> LENGTH: 441
<212> TYPE: PRT
<213> ORGANISM: Arabidopsis thaliana

<400> SEQUENCE: 62

Met Asp Ser Thr Lys Leu Ser Glu Leu Lys Val Phe Ile Asp Gln Cys
1               5                   10                  15

Lys Ser Asp Pro Ser Leu Leu Thr Thr Pro Ser Leu Ser Phe Phe Arg
            20                  25                  30

Asp Tyr Leu Glu Ser Leu Gly Ala Lys Ile Pro Thr Gly Val His Glu
        35                  40                  45

Glu Asp Lys Asp Thr Lys Pro Arg Ser Phe Val Val Glu Glu Ser Asp
```

```
    50                  55                  60

Asp Asp Met Asp Glu Thr Glu Glu Val Lys Pro Lys Val Glu Glu Glu
65                  70                  75                  80

Glu Glu Glu Asp Glu Ile Val Glu Ser Asp Val Glu Leu Glu Gly Asp
                85                  90                  95

Thr Val Glu Pro Asp Asn Asp Pro Pro Gln Lys Met Gly Asp Ser Ser
            100                 105                 110

Val Glu Val Thr Asp Glu Asn Arg Glu Ala Ala Gln Glu Ala Lys Gly
        115                 120                 125

Lys Ala Met Glu Ala Leu Ser Glu Gly Asn Phe Asp Glu Ala Ile Glu
    130                 135                 140

His Leu Thr Arg Ala Ile Thr Leu Asn Pro Thr Ser Ala Ile Met Tyr
145                 150                 155                 160

Gly Asn Arg Ala Ser Val Tyr Ile Lys Leu Lys Lys Pro Asn Ala Ala
                165                 170                 175

Ile Arg Asp Ala Asn Ala Ala Leu Glu Ile Asn Pro Asp Ser Ala Lys
            180                 185                 190

Gly Tyr Lys Ser Arg Gly Met Ala Arg Ala Met Leu Gly Glu Trp Ala
        195                 200                 205

Glu Ala Ala Lys Asp Leu His Leu Ala Ser Thr Ile Asp Tyr Asp Glu
    210                 215                 220

Glu Ile Ser Ala Val Leu Lys Lys Val Glu Pro Asn Ala His Lys Leu
225                 230                 235                 240

Glu Glu His Arg Arg Lys Tyr Asp Arg Leu Arg Lys Glu Arg Glu Asp
                245                 250                 255

Lys Lys Ala Glu Arg Asp Arg Leu Arg Arg Arg Ala Glu Ala Gln Ala
            260                 265                 270

Ala Tyr Asp Lys Ala Lys Lys Glu Glu Gln Ser Ser Ser Ser Arg Pro
        275                 280                 285

Ser Gly Gly Gly Phe Pro Gly Gly Met Pro Gly Gly Phe Pro Gly Gly
    290                 295                 300

Met Pro Gly Gly Phe Pro Gly Gly Met Gly Gly Met Pro Gly Gly Phe
305                 310                 315                 320

Pro Gly Gly Met Gly Gly Met Gly Gly Met Pro Gly Gly Phe Pro Gly
                325                 330                 335

Gly Met Gly Gly Gly Met Pro Ala Gly Met Gly Gly Gly Met Pro Gly
            340                 345                 350

Met Gly Gly Gly Met Pro Ala Gly Met Gly Gly Gly Gly Met Pro Gly
        355                 360                 365

Ala Gly Gly Gly Met Pro Gly Gly Gly Gly Met Pro Gly Gly Met Asp
    370                 375                 380

Phe Ser Lys Ile Leu Asn Asp Pro Glu Leu Met Thr Ala Phe Ser Asp
385                 390                 395                 400

Pro Glu Val Met Ala Ala Leu Gln Asp Val Met Lys Asn Pro Ala Asn
                405                 410                 415

Leu Ala Lys His Gln Ala Asn Pro Lys Val Ala Pro Val Ile Ala Lys
            420                 425                 430

Met Met Gly Lys Phe Ala Gly Pro Gln
        435                 440
```

<210> SEQ ID NO 63
<211> LENGTH: 2448
<212> TYPE: DNA
<213> ORGANISM: Arabidopsis thaliana

<400> SEQUENCE: 63

```
atgaaggttc acgagacaag atctcacgct cacatgtctg gagacgaaca aaagaaggga     60
aatttgcgga agcacaaagc agaagggaaa cttccagaat ctgaacagtc tcagaagaag    120
gcaaagcctg aaaacgatga cggacgttct gtcaacggcg ccggagatgc tgcttcagag    180
tacaatgagt tctgcaaagc ggttgaggag aatctgtcca ttgatcagat taaagaagtt    240
ctcgaaatca acggccaaga ttgttctgct ccagaagaga ccttgctagc tcaatgtcaa    300
gatttgctgt tctatggggc attagctaaa tgtcctttat gcggaggaac tttaatttgc    360
gacaatgaaa agagatttgt atgtggaggt gagataagtg agtggtgcag ttgcgtgttt    420
agtacgaaag atcctcctag aaaggaagag ccagttaaaa tccctgattc tgtcatgaac    480
tctgctatat ctgacttgat caagaaacac caggacccta aagccgacc taaaagagag     540
ttaggctctg ctgataaacc ctttgtggga atgatgatct ctctcatggg acgtctcacg    600
agaacacatc aatattggaa gaaaaagatc gagagaaacg gtgggaaagt ctccaatact    660
gttcaaggcg taacatgttt ggtggtttcg ccagctgaaa gagaacgagg tggtacgtca    720
aagatggtgg aggcaatgga acaaggtcta ccggttgtga gcgaagcatg gttgatcgac    780
agcgtggaga agcatgaagc tcagccactt gaagcttatg acgtggtcag tgatctttca    840
gtggaaggga aaggaattcc atgggataag caagatccta gtgaggaggc aattgaatcc    900
ttttctgctg agctcaaaat gtatgggaaa agaggagtgt acatggacac aaaacttcag    960
gagagaggag gaaagatctt cgagaaagat ggactcttgt ataactgtgc cttctcgata   1020
tgcgatttgg gaaaagggcg taatgagtat tgtattatgc agctagtcac ggtacccgat   1080
agtaacctga acatgtactt caagagaggg aaagtaggag atgaccctaa tgccgaagag   1140
aggctcgagg aatgggagga cgaagaagct gcgatcaaag agtttgcaag gcttttttgag  1200
gagatagcag ggaatgagtt tgagccatgg gaacgtgaga agaagattca aaagaagcct   1260
cataagtttt tcccaattga tatggatgat ggaatcgaag taaggagtgg ggctcttggt   1320
ctaaggcagc ttggcattgc ttctgctcat tgcaagcttg attcgtttgt tgcaaacttc   1380
attaaagttc tgtgtggtca agagatttac aattacgcgt tgatggagct tggattggat   1440
ccgcccgatc tacctatggg aatgctaact gatatccact tgaaacgatg cgaagaggta   1500
ttactcgagt ttgttgagaa ggtcaaaaca acaaaaagaga caggtcagaa agctgaagca  1560
atgtgggcag acttcagctc acgatggttc tctttgatgc acagcactag gccgatgcga   1620
ttacacgatg tcaatgaact tgcagaccat gcggcctctg cttttgagac ggtgagggac   1680
ataaacacag catctcgttt gatagggggac atgcgaggag acacactcga tgatccgttg  1740
tctgataggt acaaaaaact tggctgcaag atatctgtgg tagacaaaga gtctgaagat   1800
tacaagatgg ttgtgaagta tctcgagact acttatgagc ctgtgaaagt ctctgatgtt   1860
gagtacggtg tgtcagtgca gaatgttttt gcggttgagt cagatgcaat tccttcatta   1920
gatgatatca agaagttacc aaataaggtc cttttatggt gtgggtctcg gagctcaaat   1980
ctattgagac atatctacaa aggggttctta cctgctgtat gctctcttcc ggttcctggt  2040
tatatgtttg ggagagcgat agtgtgttca gatgcagctg cagaagcagc aaggtatggt   2100
tttacggctg tggatagacc agaagggttt cttgtattag ccgtagcatc acttggtgag   2160
gaagttacag aatttacaag tccaccagag gatacgaaga cgttggaaga taaaaagatt   2220
ggagtgaaag gattagggag gaagaaaact gaagagtcgg agcatttcat gtggagagat   2280
gacataaaag ttccttgtgg acggttggtt ccatcggaac ataaggacag tccacttgag   2340
```

```
tacaacgagt acgcggttta tgatccgaaa cagacaagta taaggttctt ggtggaagtg   2400

aagtacgagg agaagggaac tgagatagtc gatgtcgaac cagagtag                2448


<210> SEQ ID NO 64
<211> LENGTH: 815
<212> TYPE: PRT
<213> ORGANISM: Arabidopsis thaliana

<400> SEQUENCE: 64

Met Lys Val His Glu Thr Arg Ser His Ala His Met Ser Gly Asp Glu
1               5                   10                  15

Gln Lys Lys Gly Asn Leu Arg Lys His Lys Ala Glu Gly Lys Leu Pro
            20                  25                  30

Glu Ser Glu Gln Ser Gln Lys Lys Ala Lys Pro Glu Asn Asp Asp Gly
        35                  40                  45

Arg Ser Val Asn Gly Ala Gly Asp Ala Ala Ser Glu Tyr Asn Glu Phe
    50                  55                  60

Cys Lys Ala Val Glu Glu Asn Leu Ser Ile Asp Gln Ile Lys Glu Val
65                  70                  75                  80

Leu Glu Ile Asn Gly Gln Asp Cys Ser Ala Pro Glu Glu Thr Leu Leu
                85                  90                  95

Ala Gln Cys Gln Asp Leu Leu Phe Tyr Gly Ala Leu Ala Lys Cys Pro
            100                 105                 110

Leu Cys Gly Gly Thr Leu Ile Cys Asp Asn Glu Lys Arg Phe Val Cys
        115                 120                 125

Gly Gly Glu Ile Ser Glu Trp Cys Ser Cys Val Phe Ser Thr Lys Asp
    130                 135                 140

Pro Pro Arg Lys Glu Glu Pro Val Lys Ile Pro Asp Ser Val Met Asn
145                 150                 155                 160

Ser Ala Ile Ser Asp Leu Ile Lys Lys His Gln Asp Pro Lys Ser Arg
                165                 170                 175

Pro Lys Arg Glu Leu Gly Ser Ala Asp Lys Pro Phe Val Gly Met Met
            180                 185                 190

Ile Ser Leu Met Gly Arg Leu Thr Arg Thr His Gln Tyr Trp Lys Lys
        195                 200                 205

Lys Ile Glu Arg Asn Gly Gly Lys Val Ser Asn Thr Val Gln Gly Val
    210                 215                 220

Thr Cys Leu Val Val Ser Pro Ala Glu Arg Glu Arg Gly Gly Thr Ser
225                 230                 235                 240

Lys Met Val Glu Ala Met Glu Gln Gly Leu Pro Val Val Ser Glu Ala
                245                 250                 255

Trp Leu Ile Asp Ser Val Glu Lys His Glu Ala Gln Pro Leu Glu Ala
            260                 265                 270

Tyr Asp Val Val Ser Asp Leu Ser Val Glu Gly Lys Gly Ile Pro Trp
        275                 280                 285

Asp Lys Gln Asp Pro Ser Glu Glu Ala Ile Glu Ser Phe Ser Ala Glu
    290                 295                 300

Leu Lys Met Tyr Gly Lys Arg Gly Val Tyr Met Asp Thr Lys Leu Gln
305                 310                 315                 320

Glu Arg Gly Gly Lys Ile Phe Glu Lys Asp Gly Leu Leu Tyr Asn Cys
                325                 330                 335

Ala Phe Ser Ile Cys Asp Leu Gly Lys Gly Arg Asn Glu Tyr Cys Ile
            340                 345                 350

Met Gln Leu Val Thr Val Pro Asp Ser Asn Leu Asn Met Tyr Phe Lys
        355                 360                 365
```

```
Arg Gly Lys Val Gly Asp Asp Pro Asn Ala Glu Glu Arg Leu Glu Glu
    370                 375                 380

Trp Glu Asp Glu Glu Ala Ala Ile Lys Glu Phe Ala Arg Leu Phe Glu
385                 390                 395                 400

Glu Ile Ala Gly Asn Glu Phe Glu Pro Trp Glu Arg Glu Lys Lys Ile
                405                 410                 415

Gln Lys Lys Pro His Lys Phe Phe Pro Ile Asp Met Asp Asp Gly Ile
            420                 425                 430

Glu Val Arg Ser Gly Ala Leu Gly Leu Arg Gln Leu Gly Ile Ala Ser
        435                 440                 445

Ala His Cys Lys Leu Asp Ser Phe Val Ala Asn Phe Ile Lys Val Leu
    450                 455                 460

Cys Gly Gln Glu Ile Tyr Asn Tyr Ala Leu Met Glu Leu Gly Leu Asp
465                 470                 475                 480

Pro Pro Asp Leu Pro Met Gly Met Leu Thr Asp Ile His Leu Lys Arg
                485                 490                 495

Cys Glu Glu Val Leu Leu Glu Phe Val Glu Lys Val Lys Thr Thr Lys
            500                 505                 510

Glu Thr Gly Gln Lys Ala Glu Ala Met Trp Ala Asp Phe Ser Ser Arg
        515                 520                 525

Trp Phe Ser Leu Met His Ser Thr Arg Pro Met Arg Leu His Asp Val
    530                 535                 540

Asn Glu Leu Ala Asp His Ala Ala Ser Ala Phe Glu Thr Val Arg Asp
545                 550                 555                 560

Ile Asn Thr Ala Ser Arg Leu Ile Gly Asp Met Arg Gly Asp Thr Leu
                565                 570                 575

Asp Asp Pro Leu Ser Asp Arg Tyr Lys Lys Leu Gly Cys Lys Ile Ser
            580                 585                 590

Val Val Asp Lys Glu Ser Glu Asp Tyr Lys Met Val Val Lys Tyr Leu
        595                 600                 605

Glu Thr Thr Tyr Glu Pro Val Lys Val Ser Asp Val Glu Tyr Gly Val
    610                 615                 620

Ser Val Gln Asn Val Phe Ala Val Glu Ser Asp Ala Ile Pro Ser Leu
625                 630                 635                 640

Asp Asp Ile Lys Lys Leu Pro Asn Lys Val Leu Leu Trp Cys Gly Ser
                645                 650                 655

Arg Ser Ser Asn Leu Leu Arg His Ile Tyr Lys Gly Phe Leu Pro Ala
            660                 665                 670

Val Cys Ser Leu Pro Val Pro Gly Tyr Met Phe Gly Arg Ala Ile Val
        675                 680                 685

Cys Ser Asp Ala Ala Ala Glu Ala Ala Arg Tyr Gly Phe Thr Ala Val
    690                 695                 700

Asp Arg Pro Glu Gly Phe Leu Val Leu Ala Val Ala Ser Leu Gly Glu
705                 710                 715                 720

Glu Val Thr Glu Phe Thr Ser Pro Pro Glu Asp Thr Lys Thr Leu Glu
                725                 730                 735

Asp Lys Lys Ile Gly Val Lys Gly Leu Gly Arg Lys Lys Thr Glu Glu
            740                 745                 750

Ser Glu His Phe Met Trp Arg Asp Asp Ile Lys Val Pro Cys Gly Arg
        755                 760                 765

Leu Val Pro Ser Glu His Lys Asp Ser Pro Leu Glu Tyr Asn Glu Tyr
    770                 775                 780

Ala Val Tyr Asp Pro Lys Gln Thr Ser Ile Arg Phe Leu Val Glu Val
```

```
785                 790                 795                 800

Lys Tyr Glu Glu Lys Gly Thr Glu Ile Val Asp Val Glu Pro Glu
                805                 810                 815


<210> SEQ ID NO 65
<211> LENGTH: 2430
<212> TYPE: DNA
<213> ORGANISM: Arabidopsis thaliana

<400> SEQUENCE: 65

atgtctaccc cagctgaatc ttcagactcg aaatcgaaga aagatttcag tactgctatt     60

ctcgagagga agaagtctcc gaaccgtctc gtcgtcgatg aggctatcaa cgatgataac    120

tccgtcgtct ctcttcaccc tgcaaccatg gagaagcttc agctcttccg tggtgatacc    180

attctcatca agggtaagaa gaggaaggac actgtctgca ttgctcttgc tgatgagaca    240

tgtgaggagc caaagatcag aatgaataaa gtagtcagat ctaacttgag ggttagactg    300

ggagatgtta tatctgttca ccaatgccca gacgtcaagt acggaaagcg tgttcacatc    360

ctgcctgttg atgatactgt tgaaggagtg actggaaacc tatttgatgc ttacctgaaa    420

ccttatttcc ttgaggcata ccgtccagtg aggaagggtg atctcttcct agtcagagga    480

ggaatgagga gtgtggagtt caaagttata gagacagatc ctgctgagta ctgcgtggtt    540

gctccagaca cagagatttt ctgtgagggt gagcctgtga agagagagga tgaagaaagg    600

ctagatgatg taggttatga tgatgttggt ggtgtcagga aacagatggc tcagattagg    660

gaacttgttg aacttccctt gaggcatcca cagctattca agtcgattgg tgttaagcca    720

ccgaagggaa ttcttcttta tggaccacct gggtctggaa agactttgat cgctcgtgct    780

gtggctaatg aaacgggtgc ctttttcttc tgtatcaacg gacctgagat catgtccaaa    840

ttggctggtg agagtgagag caacctcagg aaagcattcg aggaggctga gaaaaatgcg    900

ccttcaatca tattcattga tgagatcgac tctattgcac cgaaaagaga gaagactaat    960

ggagaggttg agaggaggat tgtctctcag ctccttacgc taatggatgg actgaaatct   1020

cgtgctcatg ttatcgtcat gggagcaacc aatcgcccca acagtatcga cccagctttg   1080

agaaggtttg gaagatttga cagggagatc gatattggag ttcctgacga aattggacgt   1140

cttgaagttc tgaggatcca tacaaagaac atgaagctgg ctgaagatgt ggatctcgaa   1200

aggatctcaa aggacacaca cggttacgtc ggtgctgatc ttgcagcttt gtgcacagag   1260

gccgccctgc aatgcatcag ggagaagatg gatgtgattg atctggaaga tgactccata   1320

gacgctgaaa tcctcaattc catggcagtc actaatgaac atttccacac tgctctcggg   1380

aacagcaacc catctgcact tcgtgaaact gttgtggagg ttcccaacgt ctcttggaat   1440

gatattggag gtcttgagaa tgtcaagaga gagctccagg agactgttca atacccagtc   1500

gagcacccag agaagtttga gaaattcggg atgtctccat caaagggagt cctttctac    1560

ggtcctcctg gatgtgggaa aacccttttg gccaaagcta ttgccaacga gtgccaagct   1620

aatttcatca gtgtcaaggg tcccgagctt ctgacaatgt ggtttggaga gagtgaagca   1680

aatgttcgtg aaatcttcga caaggcccgt caatccgctc catgtgttct ttctttgat    1740

gagctcgact ccattgcaac tcagagagga ggtggaagtg gtggcgatgg aggtggtgct   1800

gcggacagag tcttgaacca gcttttgact gagatggacg gaatgaatgc caagaaaacc   1860

gtcttcatca tcggagctac caacagacct gacattatcg attcagctct tctccgtcct   1920

ggaaggcttg accagctcat ttacattcca ctaccagatg aggattcccg tctcaatatc   1980

ttcaaggccg ccttgaggaa atctcctatt gctaaagatg tagacatcgg tgcacttgct   2040
```

```
aaatacactc agggtttcag tggtgctgat atcactgaga tttgccagag agcttgcaag   2100

tacgccatca gagaaaacat tgagaaggac attgaaaagg agaagaggag gagcgagaac   2160

ccagaggcaa tggaggaaga tggagtggat gaagtatcag agatcaaagc tgcacacttt   2220

gaggagtcga tgaagtatgc gcgtaggagt gtgagtgatg cagacatcag gaagtaccaa   2280

gcctttgctc agacgttgca gcagtctaga gggttcggtt ctgagttcag gttcgagaat   2340

tctgctggtt caggtgccac cactggagtc gcagatccgt ttgccacgtc tgcagccgct   2400

gctggggacg atgatgatct ctacaattag                                    2430


<210> SEQ ID NO 66
<211> LENGTH: 809
<212> TYPE: PRT
<213> ORGANISM: Arabidopsis thaliana

<400> SEQUENCE: 66

Met Ser Thr Pro Ala Glu Ser Ser Asp Ser Lys Ser Lys Lys Asp Phe
1               5                   10                  15

Ser Thr Ala Ile Leu Glu Arg Lys Lys Ser Pro Asn Arg Leu Val Val
            20                  25                  30

Asp Glu Ala Ile Asn Asp Asp Asn Ser Val Val Ser Leu His Pro Ala
        35                  40                  45

Thr Met Glu Lys Leu Gln Leu Phe Arg Gly Asp Thr Ile Leu Ile Lys
    50                  55                  60

Gly Lys Lys Arg Lys Asp Thr Val Cys Ile Ala Leu Ala Asp Glu Thr
65                  70                  75                  80

Cys Glu Glu Pro Lys Ile Arg Met Asn Lys Val Val Arg Ser Asn Leu
                85                  90                  95

Arg Val Arg Leu Gly Asp Val Ile Ser Val His Gln Cys Pro Asp Val
            100                 105                 110

Lys Tyr Gly Lys Arg Val His Ile Leu Pro Val Asp Asp Thr Val Glu
        115                 120                 125

Gly Val Thr Gly Asn Leu Phe Asp Ala Tyr Leu Lys Pro Tyr Phe Leu
    130                 135                 140

Glu Ala Tyr Arg Pro Val Arg Lys Gly Asp Leu Phe Leu Val Arg Gly
145                 150                 155                 160

Gly Met Arg Ser Val Glu Phe Lys Val Ile Glu Thr Asp Pro Ala Glu
                165                 170                 175

Tyr Cys Val Val Ala Pro Asp Thr Glu Ile Phe Cys Glu Gly Glu Pro
            180                 185                 190

Val Lys Arg Glu Asp Glu Glu Arg Leu Asp Asp Val Gly Tyr Asp Asp
        195                 200                 205

Val Gly Gly Val Arg Lys Gln Met Ala Gln Ile Arg Glu Leu Val Glu
    210                 215                 220

Leu Pro Leu Arg His Pro Gln Leu Phe Lys Ser Ile Gly Val Lys Pro
225                 230                 235                 240

Pro Lys Gly Ile Leu Leu Tyr Gly Pro Pro Gly Ser Gly Lys Thr Leu
                245                 250                 255

Ile Ala Arg Ala Val Ala Asn Glu Thr Gly Ala Phe Phe Phe Cys Ile
            260                 265                 270

Asn Gly Pro Glu Ile Met Ser Lys Leu Ala Gly Glu Ser Glu Ser Asn
        275                 280                 285

Leu Arg Lys Ala Phe Glu Glu Ala Glu Lys Asn Ala Pro Ser Ile Ile
    290                 295                 300
```

```
Phe Ile Asp Glu Ile Asp Ser Ile Ala Pro Lys Arg Glu Lys Thr Asn
305                 310                 315                 320

Gly Glu Val Glu Arg Arg Ile Val Ser Gln Leu Leu Thr Leu Met Asp
                325                 330                 335

Gly Leu Lys Ser Arg Ala His Val Ile Val Met Gly Ala Thr Asn Arg
            340                 345                 350

Pro Asn Ser Ile Asp Pro Ala Leu Arg Arg Phe Gly Arg Phe Asp Arg
        355                 360                 365

Glu Ile Asp Ile Gly Val Pro Asp Glu Ile Gly Arg Leu Glu Val Leu
    370                 375                 380

Arg Ile His Thr Lys Asn Met Lys Leu Ala Glu Asp Val Asp Leu Glu
385                 390                 395                 400

Arg Ile Ser Lys Asp Thr His Gly Tyr Val Gly Ala Asp Leu Ala Ala
                405                 410                 415

Leu Cys Thr Glu Ala Ala Leu Gln Cys Ile Arg Glu Lys Met Asp Val
            420                 425                 430

Ile Asp Leu Glu Asp Asp Ser Ile Asp Ala Glu Ile Leu Asn Ser Met
        435                 440                 445

Ala Val Thr Asn Glu His Phe His Thr Ala Leu Gly Asn Ser Asn Pro
    450                 455                 460

Ser Ala Leu Arg Glu Thr Val Val Glu Val Pro Asn Val Ser Trp Asn
465                 470                 475                 480

Asp Ile Gly Gly Leu Glu Asn Val Lys Arg Glu Leu Gln Glu Thr Val
                485                 490                 495

Gln Tyr Pro Val Glu His Pro Glu Lys Phe Glu Lys Phe Gly Met Ser
            500                 505                 510

Pro Ser Lys Gly Val Leu Phe Tyr Gly Pro Pro Gly Cys Gly Lys Thr
        515                 520                 525

Leu Leu Ala Lys Ala Ile Ala Asn Glu Cys Gln Ala Asn Phe Ile Ser
    530                 535                 540

Val Lys Gly Pro Glu Leu Leu Thr Met Trp Phe Gly Glu Ser Glu Ala
545                 550                 555                 560

Asn Val Arg Glu Ile Phe Asp Lys Ala Arg Gln Ser Ala Pro Cys Val
                565                 570                 575

Leu Phe Phe Asp Glu Leu Asp Ser Ile Ala Thr Gln Arg Gly Gly Gly
            580                 585                 590

Ser Gly Gly Asp Gly Gly Gly Ala Ala Asp Arg Val Leu Asn Gln Leu
        595                 600                 605

Leu Thr Glu Met Asp Gly Met Asn Ala Lys Lys Thr Val Phe Ile Ile
    610                 615                 620

Gly Ala Thr Asn Arg Pro Asp Ile Ile Asp Ser Ala Leu Leu Arg Pro
625                 630                 635                 640

Gly Arg Leu Asp Gln Leu Ile Tyr Ile Pro Leu Pro Asp Glu Asp Ser
                645                 650                 655

Arg Leu Asn Ile Phe Lys Ala Ala Leu Arg Lys Ser Pro Ile Ala Lys
            660                 665                 670

Asp Val Asp Ile Gly Ala Leu Ala Lys Tyr Thr Gln Gly Phe Ser Gly
        675                 680                 685

Ala Asp Ile Thr Glu Ile Cys Gln Arg Ala Cys Lys Tyr Ala Ile Arg
    690                 695                 700

Glu Asn Ile Glu Lys Asp Ile Glu Lys Glu Lys Arg Arg Ser Glu Asn
705                 710                 715                 720

Pro Glu Ala Met Glu Glu Asp Gly Val Asp Glu Val Ser Glu Ile Lys
                725                 730                 735
```

```
Ala Ala His Phe Glu Glu Ser Met Lys Tyr Ala Arg Arg Ser Val Ser
            740                 745                 750

Asp Ala Asp Ile Arg Lys Tyr Gln Ala Phe Ala Gln Thr Leu Gln Gln
        755                 760                 765

Ser Arg Gly Phe Gly Ser Glu Phe Arg Phe Glu Asn Ser Ala Gly Ser
    770                 775                 780

Gly Ala Thr Thr Gly Val Ala Asp Pro Phe Ala Thr Ser Ala Ala Ala
785                 790                 795                 800

Ala Gly Asp Asp Asp Asp Leu Tyr Asn
                805
```

```
<210> SEQ ID NO 67
<211> LENGTH: 2847
<212> TYPE: DNA
<213> ORGANISM: Arabidopsis thaliana

<400> SEQUENCE: 67

atggacaaat ctagtaccat gcttgttcac tatgacaaag ggactccagc agttgctaat      60

gagattaaag aagctctcga aggaaatgat gttgaagcta aagttgatgc catgaagaag     120

gcaattatgc ttttgctgaa tggtgaaacc attcctcagc ttttcattac cattataaga     180

tatgtgctgc cttctgaaga ccacaccatc caaaagcttc tgttgctgta cctggagctg     240

attgaaaaga cagattcgaa ggggaaggtg ttgcctgaaa tgattttgat atgccagaat     300

cttcgtaata accttcagca tccgaatgag tacatccgtg gagtgacact gaggtttctc     360

tgtcggatga aggagactga aatagtggaa cctttgactc catcagtgtt acaaaatctg     420

gagcatcgcc atccatttgt tcgcaggaat gcaattctgg caatcatgtc gatatataaa     480

cttccacatg gcgaccaact cttcgtggat gcacctgaaa tgatcgagaa agttctatca     540

acagaacaag atccttctgc caagagaaat gcatttctaa tgctctttac ctgtgccgaa     600

gaacgtgcag tgaattatct tctgagcaat gttgacaagg tttcagactg gaatgaatca     660

cttcagatgg tggtgctgga gctgattcga agtgtgtgta agactaaacc agcggagaag     720

ggaaaatata ttaaaattat tatttctctg ttaagtgcta cttcttctgc agttatctat     780

gaatgtgctg ggacacttgt ttctctctca tctgccccta ctgctattcg agctgctgcc     840

aacacctact gccaacttct tctttctcag agtgacaaca atgtgaagct tatcttgctc     900

gatcggttgt atgagcttaa gacattgcac agagatatca tggttgagct gataatcgat     960

gtgctcagag cactctcaag cccaaacctt gatatccgca ggaagacact tgacattgcc    1020

cttgacttga ttacccatca taatattaat gaagtcgttc aaatgttgaa gaaagaagtt    1080

gtgaagacac agagtggaga acttgagaag aatggagagt acaggcaaat gcttattcaa    1140

gccatccatg cttgtgcagt taagttcccc gaagttgcaa gcacagtggt ccatcttctg    1200

atggatttcc tgggagatag caacgtggct tcagctcttg acgtggttgt tttcgttaga    1260

gagataatag aaacaaatcc caagttgaga gtttcaatca tcaccaggtt gttggacacg    1320

ttctatcaga tccgtgcagg aaaggtctgc ccttgtgcac tttggatcat tggtgagtat    1380

tgcctatcac tttcagaagt tgagagtggc atttcaacta ttacacaatg ccttggcgaa    1440

ttaccatttt actctgtttc tgaggagtct gagccaactg agacatcaaa gaagattcag    1500

cctacctctt ctgccatggt gtcctctaga aagccagtta ttcttgctga tggaacttat    1560

gctacacaaa gcgcagcctc tgaaaccaca ttctcctcgc ctacagttgt tcaaggatca    1620

ctgacttctg gaaatttgag ggcactcctt ctaactggtg atttttttcct cggagctgtg    1680
```

```
gttgcttgca cgttgaccaa acttgttctt aggttggaag aggttcagtc ttccaaaact   1740

gaagtaaaca agacagtatc acaggctttg ctaatcatgg tttctatttt gcaacttggg   1800

caatctcctg tttctccaca ccctattgat aatgattcgt atgagcggat tatgttgtgc   1860

ataaaattgc tttgccatag gaatgttgag atgaaaaaga tatggttgga atcctgccgc   1920

cagagttttg tcaagatgat ttctgaaaaa cagcttagag agatggagga actgaaggca   1980

aagacccaaa caactcatgc tcaaccggat gatctaattg acttcttcca tctaaagagt   2040

cggaagggaa tgagtcaact tgagttggaa gaccaggtac aagatgacct aaagcgtgca   2100

actggagaat tcaccaagga cgagaacgat gctaacaaac ttaaccgcat tcttcaactc   2160

acaggattca gtgacccagt ctatgctgaa gcatatgtaa cggtacacca ttatgatatt   2220

gctcttgaag ttacagtaat caaccgaacc aaggaaaccc ttcagaactt gtgcttggag   2280

ttagcaacca tgggtgatct caaacttgtt gagcgtcctc agaactatag tctggcacct   2340

gaaagaagca tgcagattaa agcaaacatc aaggtctcgt ccacagagac aggagtcata   2400

ttcgggaaca tcgtctatga gacatcaaat gtaatggagc gcaatgttgt ggttcttaac   2460

gacatacaca ttgatatcat ggactatatc tcccctgctg tgtgctcaga ggttgctttc   2520

agaactatgt gggcagagtt tgaatgggaa aacaaggttg ctgtgaacac cacaattcaa   2580

aacgaaagag aattcctcga ccacattatc aaatccacaa acatgaaatg tctcactgct   2640

ccatctgcaa tagcaggtga atgtggattc cttgcagcaa acttatatgc aaaaagtgta   2700

tttggtgagg atgctcttgt gaatttgagt attgagaagc aaacggatgg aacattgagt   2760

ggttacataa ggataaggag caagacgcaa gggattgctc taagtcttgg agacaaaatc   2820

accctcaaac aaaagggtgg tagctga                                       2847
```

<210> SEQ ID NO 68
<211> LENGTH: 948
<212> TYPE: PRT
<213> ORGANISM: Arabidopsis thaliana

<400> SEQUENCE: 68

```
Met Asp Lys Ser Ser Thr Met Leu Val His Tyr Asp Lys Gly Thr Pro
1               5                   10                  15

Ala Val Ala Asn Glu Ile Lys Glu Ala Leu Glu Gly Asn Asp Val Glu
            20                  25                  30

Ala Lys Val Asp Ala Met Lys Lys Ala Ile Met Leu Leu Leu Asn Gly
        35                  40                  45

Glu Thr Ile Pro Gln Leu Phe Ile Thr Ile Ile Arg Tyr Val Leu Pro
    50                  55                  60

Ser Glu Asp His Thr Ile Gln Lys Leu Leu Leu Leu Tyr Leu Glu Leu
65                  70                  75                  80

Ile Glu Lys Thr Asp Ser Lys Gly Lys Val Leu Pro Glu Met Ile Leu
                85                  90                  95

Ile Cys Gln Asn Leu Arg Asn Asn Leu Gln His Pro Asn Glu Tyr Ile
            100                 105                 110

Arg Gly Val Thr Leu Arg Phe Leu Cys Arg Met Lys Glu Thr Glu Ile
        115                 120                 125

Val Glu Pro Leu Thr Pro Ser Val Leu Gln Asn Leu Glu His Arg His
    130                 135                 140

Pro Phe Val Arg Arg Asn Ala Ile Leu Ala Ile Met Ser Ile Tyr Lys
145                 150                 155                 160

Leu Pro His Gly Asp Gln Leu Phe Val Asp Ala Pro Glu Met Ile Glu
                165                 170                 175
```

```
Lys Val Leu Ser Thr Glu Gln Asp Pro Ser Ala Lys Arg Asn Ala Phe
            180                 185                 190

Leu Met Leu Phe Thr Cys Ala Glu Glu Arg Ala Val Asn Tyr Leu Leu
        195                 200                 205

Ser Asn Val Asp Lys Val Ser Asp Trp Asn Glu Ser Leu Gln Met Val
    210                 215                 220

Val Leu Glu Leu Ile Arg Ser Val Cys Lys Thr Lys Pro Ala Glu Lys
225                 230                 235                 240

Gly Lys Tyr Ile Lys Ile Ile Ile Ser Leu Leu Ser Ala Thr Ser Ser
                245                 250                 255

Ala Val Ile Tyr Glu Cys Ala Gly Thr Leu Val Ser Leu Ser Ser Ala
            260                 265                 270

Pro Thr Ala Ile Arg Ala Ala Ala Asn Thr Tyr Cys Gln Leu Leu Leu
        275                 280                 285

Ser Gln Ser Asp Asn Asn Val Lys Leu Ile Leu Leu Asp Arg Leu Tyr
    290                 295                 300

Glu Leu Lys Thr Leu His Arg Asp Ile Met Val Glu Leu Ile Ile Asp
305                 310                 315                 320

Val Leu Arg Ala Leu Ser Ser Pro Asn Leu Asp Ile Arg Arg Lys Thr
                325                 330                 335

Leu Asp Ile Ala Leu Asp Leu Ile Thr His His Asn Ile Asn Glu Val
            340                 345                 350

Val Gln Met Leu Lys Lys Glu Val Val Lys Thr Gln Ser Gly Glu Leu
        355                 360                 365

Glu Lys Asn Gly Glu Tyr Arg Gln Met Leu Ile Gln Ala Ile His Ala
    370                 375                 380

Cys Ala Val Lys Phe Pro Glu Val Ala Ser Thr Val Val His Leu Leu
385                 390                 395                 400

Met Asp Phe Leu Gly Asp Ser Asn Val Ala Ser Ala Leu Asp Val Val
                405                 410                 415

Val Phe Val Arg Glu Ile Ile Glu Thr Asn Pro Lys Leu Arg Val Ser
            420                 425                 430

Ile Ile Thr Arg Leu Leu Asp Thr Phe Tyr Gln Ile Arg Ala Gly Lys
        435                 440                 445

Val Cys Pro Cys Ala Leu Trp Ile Ile Gly Glu Tyr Cys Leu Ser Leu
    450                 455                 460

Ser Glu Val Glu Ser Gly Ile Ser Thr Ile Thr Gln Cys Leu Gly Glu
465                 470                 475                 480

Leu Pro Phe Tyr Ser Val Ser Glu Glu Ser Glu Pro Thr Glu Thr Ser
                485                 490                 495

Lys Lys Ile Gln Pro Thr Ser Ser Ala Met Val Ser Ser Arg Lys Pro
            500                 505                 510

Val Ile Leu Ala Asp Gly Thr Tyr Ala Thr Gln Ser Ala Ala Ser Glu
        515                 520                 525

Thr Thr Phe Ser Ser Pro Thr Val Val Gln Gly Ser Leu Thr Ser Gly
    530                 535                 540

Asn Leu Arg Ala Leu Leu Leu Thr Gly Asp Phe Phe Leu Gly Ala Val
545                 550                 555                 560

Val Ala Cys Thr Leu Thr Lys Leu Val Leu Arg Leu Glu Glu Val Gln
                565                 570                 575

Ser Ser Lys Thr Glu Val Asn Lys Thr Val Ser Gln Ala Leu Leu Ile
            580                 585                 590

Met Val Ser Ile Leu Gln Leu Gly Gln Ser Pro Val Ser Pro His Pro
```

```
        595                 600                 605

Ile Asp Asn Asp Ser Tyr Glu Arg Ile Met Leu Cys Ile Lys Leu Leu
    610                 615                 620

Cys His Arg Asn Val Glu Met Lys Lys Ile Trp Leu Glu Ser Cys Arg
625                 630                 635                 640

Gln Ser Phe Val Lys Met Ile Ser Glu Lys Gln Leu Arg Glu Met Glu
                645                 650                 655

Glu Leu Lys Ala Lys Thr Gln Thr Thr His Ala Gln Pro Asp Asp Leu
            660                 665                 670

Ile Asp Phe Phe His Leu Lys Ser Arg Lys Gly Met Ser Gln Leu Glu
        675                 680                 685

Leu Glu Asp Gln Val Gln Asp Asp Leu Lys Arg Ala Thr Gly Glu Phe
    690                 695                 700

Thr Lys Asp Glu Asn Asp Ala Asn Lys Leu Asn Arg Ile Leu Gln Leu
705                 710                 715                 720

Thr Gly Phe Ser Asp Pro Val Tyr Ala Glu Ala Tyr Val Thr Val His
                725                 730                 735

His Tyr Asp Ile Ala Leu Glu Val Thr Val Ile Asn Arg Thr Lys Glu
            740                 745                 750

Thr Leu Gln Asn Leu Cys Leu Glu Leu Ala Thr Met Gly Asp Leu Lys
        755                 760                 765

Leu Val Glu Arg Pro Gln Asn Tyr Ser Leu Ala Pro Glu Arg Ser Met
    770                 775                 780

Gln Ile Lys Ala Asn Ile Lys Val Ser Ser Thr Glu Thr Gly Val Ile
785                 790                 795                 800

Phe Gly Asn Ile Val Tyr Glu Thr Ser Asn Val Met Glu Arg Asn Val
                805                 810                 815

Val Val Leu Asn Asp Ile His Ile Asp Ile Met Asp Tyr Ile Ser Pro
            820                 825                 830

Ala Val Cys Ser Glu Val Ala Phe Arg Thr Met Trp Ala Glu Phe Glu
        835                 840                 845

Trp Glu Asn Lys Val Ala Val Asn Thr Thr Ile Gln Asn Glu Arg Glu
    850                 855                 860

Phe Leu Asp His Ile Ile Lys Ser Thr Asn Met Lys Cys Leu Thr Ala
865                 870                 875                 880

Pro Ser Ala Ile Ala Gly Glu Cys Gly Phe Leu Ala Ala Asn Leu Tyr
                885                 890                 895

Ala Lys Ser Val Phe Gly Glu Asp Ala Leu Val Asn Leu Ser Ile Glu
            900                 905                 910

Lys Gln Thr Asp Gly Thr Leu Ser Gly Tyr Ile Arg Ile Arg Ser Lys
        915                 920                 925

Thr Gln Gly Ile Ala Leu Ser Leu Gly Asp Lys Ile Thr Leu Lys Gln
    930                 935                 940

Lys Gly Gly Ser
945
```

<210> SEQ ID NO 69
<211> LENGTH: 1086
<212> TYPE: DNA
<213> ORGANISM: Arabidopsis thaliana

<400> SEQUENCE: 69

```
atggcgaaat ctcagatctg gtttggtttt gcgttactcg cgttgcttct ggtttcagcc      60

gtagctgacg atgtggttgt tttgactgac gatagcttcg aaaaggaagt tggtaaagat     120
```

```
aaaggagctc tcgtcgagtt ttacgctccc tggtgtggtc actgcaagaa acttgctcca    180

gagtatgaaa agctaggggc aagcttcaag aaggctaagt ctgtgttgat tgcaaaggtt    240

gattgtgatg agcaaaagag tgtctgtact aaatatggtg ttagtggata cccaaccatt    300

cagtggtttc ctaaaggatc tcttgaacct caaaagtatg agggtccacg caatgctgaa    360

gctttggctg aatacgtgaa caaggaagga ggcaccaacg taaaattagc tgcagttcca    420

caaaacgtgg ttgttttgac acctgacaat ttcgatgaga ttgttctgga tcaaaacaaa    480

gatgtcctag tcgaatttta tgcaccatgg tgtggccact gcaaatcact cgctcccaca    540

tacgaaaagg tagccacagt gtttaaacag gaagaaggtg tagtcatcgc caatttggat    600

gctgatgcac acaaagccct tggcgagaaa tatggagtga gtggattccc aacattgaaa    660

ttcttcccaa aggacaacaa agctggtcac gattatgacg gtggcaggga tttagatgac    720

tttgtaagct tcatcaacga gaaatctggg accagcaggg acagtaaagg gcagcttact    780

tcaaaggctg gtatagtcga aagcttagat gctttggtaa aagagttagt tgcagctagt    840

gaagatgaga agaaggcagt gttgtctcgc atagaagagg aagcaagtac ccttaagggc    900

tccaccacga ggtatggaaa gctttacttg aaactcgcaa agagctacat agaaaaaggt    960

tcagactatg ctagcaaaga aacggagagg cttggacggg tgcttgggaa gtcgataagt   1020

ccagtgaaag ctgatgaact cactctcaag agaaatatcc taaccacgtt cgttgcttct   1080

tcttaa                                                              1086


<210> SEQ ID NO 70
<211> LENGTH: 361
<212> TYPE: PRT
<213> ORGANISM: Arabidopsis thaliana

<400> SEQUENCE: 70

Met Ala Lys Ser Gln Ile Trp Phe Gly Phe Ala Leu Leu Ala Leu Leu
1               5                   10                  15

Leu Val Ser Ala Val Ala Asp Asp Val Val Val Leu Thr Asp Asp Ser
            20                  25                  30

Phe Glu Lys Glu Val Gly Lys Asp Lys Gly Ala Leu Val Glu Phe Tyr
        35                  40                  45

Ala Pro Trp Cys Gly His Cys Lys Lys Leu Ala Pro Glu Tyr Glu Lys
    50                  55                  60

Leu Gly Ala Ser Phe Lys Lys Ala Lys Ser Val Leu Ile Ala Lys Val
65                  70                  75                  80

Asp Cys Asp Glu Gln Lys Ser Val Cys Thr Lys Tyr Gly Val Ser Gly
                85                  90                  95

Tyr Pro Thr Ile Gln Trp Phe Pro Lys Gly Ser Leu Glu Pro Gln Lys
            100                 105                 110

Tyr Glu Gly Pro Arg Asn Ala Glu Ala Leu Ala Glu Tyr Val Asn Lys
        115                 120                 125

Glu Gly Gly Thr Asn Val Lys Leu Ala Ala Val Pro Gln Asn Val Val
    130                 135                 140

Val Leu Thr Pro Asp Asn Phe Asp Glu Ile Val Leu Asp Gln Asn Lys
145                 150                 155                 160

Asp Val Leu Val Glu Phe Tyr Ala Pro Trp Cys Gly His Cys Lys Ser
                165                 170                 175

Leu Ala Pro Thr Tyr Glu Lys Val Ala Thr Val Phe Lys Gln Glu Glu
            180                 185                 190

Gly Val Val Ile Ala Asn Leu Asp Ala Asp Ala His Lys Ala Leu Gly
        195                 200                 205
```

```
Glu Lys Tyr Gly Val Ser Gly Phe Pro Thr Leu Lys Phe Phe Pro Lys
    210                 215                 220

Asp Asn Lys Ala Gly His Asp Tyr Asp Gly Gly Arg Asp Leu Asp Asp
225                 230                 235                 240

Phe Val Ser Phe Ile Asn Glu Lys Ser Gly Thr Ser Arg Asp Ser Lys
                245                 250                 255

Gly Gln Leu Thr Ser Lys Ala Gly Ile Val Glu Ser Leu Asp Ala Leu
            260                 265                 270

Val Lys Glu Leu Val Ala Ala Ser Glu Asp Glu Lys Lys Ala Val Leu
        275                 280                 285

Ser Arg Ile Glu Glu Glu Ala Ser Thr Leu Lys Gly Ser Thr Thr Arg
    290                 295                 300

Tyr Gly Lys Leu Tyr Leu Lys Leu Ala Lys Ser Tyr Ile Glu Lys Gly
305                 310                 315                 320

Ser Asp Tyr Ala Ser Lys Glu Thr Glu Arg Leu Gly Arg Val Leu Gly
                325                 330                 335

Lys Ser Ile Ser Pro Val Lys Ala Asp Glu Leu Thr Leu Lys Arg Asn
            340                 345                 350

Ile Leu Thr Thr Phe Val Ala Ser Ser
        355                 360


<210> SEQ ID NO 71
<211> LENGTH: 744
<212> TYPE: DNA
<213> ORGANISM: Arabidopsis thaliana

<400> SEQUENCE: 71

atggcgtcga gcgatgagcg tccaggagcg tatccggcac gtgacggatc agagaactta      60

cctccgggag atccaaagac gatgaagacg gtggtgatgg ataaaggagc ggcgatgatg     120

caatcgttga aaccgatcaa acagatgagt ctccatttgt gttctttcgc ttgttatggt     180

cacgatccta gccgtcagat tgaagtcaac ttctatgttc atcgactcaa ccaagacttt     240

cttcaatgtg ctgtttacga ttgcgactcc tctaaacccc atctcatcgg gatcgagtat     300

attgtgtcgg agaggttatt tgagagtctt gatccggagg agcaaaagct ttggcactct     360

catgactatg agatccaaac aggccttcta gtaactccaa gggtccctga gcttgtagct     420

aagacagagc ttgaaaatat tgccaaaact tatgggaagt tttggtgcac ttggcagacc     480

gatcgcgggg ataaattgcc acttggtgca ccatcactta tgatgtcacc acaagacgtg     540

aatatgggaa agatcaagcc agggctattg aagaaacgtg acgatgagta tggaatctcg     600

acggaatctt tgaagacgtc tcgagttgga attatgggac cggagaagaa aaattcgatg     660

gctgattatt gggttcatca cggaaaagga ttagcggttg acataatcga aactgagatg     720

cagaaattgg ctccgttccc gtaa                                            744


<210> SEQ ID NO 72
<211> LENGTH: 247
<212> TYPE: PRT
<213> ORGANISM: Arabidopsis thaliana

<400> SEQUENCE: 72

Met Ala Ser Ser Asp Glu Arg Pro Gly Ala Tyr Pro Ala Arg Asp Gly
1               5                   10                  15

Ser Glu Asn Leu Pro Pro Gly Asp Pro Lys Thr Met Lys Thr Val Val
            20                  25                  30

Met Asp Lys Gly Ala Ala Met Met Gln Ser Leu Lys Pro Ile Lys Gln
```

```
        35                  40                  45

Met Ser Leu His Leu Cys Ser Phe Ala Cys Tyr Gly His Asp Pro Ser
    50                  55                  60

Arg Gln Ile Glu Val Asn Phe Tyr Val His Arg Leu Asn Gln Asp Phe
65                  70                  75                  80

Leu Gln Cys Ala Val Tyr Asp Cys Asp Ser Ser Lys Pro His Leu Ile
                85                  90                  95

Gly Ile Glu Tyr Ile Val Ser Glu Arg Leu Phe Glu Ser Leu Asp Pro
            100                 105                 110

Glu Glu Gln Lys Leu Trp His Ser His Asp Tyr Glu Ile Gln Thr Gly
        115                 120                 125

Leu Leu Val Thr Pro Arg Val Pro Glu Leu Val Ala Lys Thr Glu Leu
    130                 135                 140

Glu Asn Ile Ala Lys Thr Tyr Gly Lys Phe Trp Cys Thr Trp Gln Thr
145                 150                 155                 160

Asp Arg Gly Asp Lys Leu Pro Leu Gly Ala Pro Ser Leu Met Met Ser
                165                 170                 175

Pro Gln Asp Val Asn Met Gly Lys Ile Lys Pro Gly Leu Leu Lys Lys
            180                 185                 190

Arg Asp Asp Glu Tyr Gly Ile Ser Thr Glu Ser Leu Lys Thr Ser Arg
        195                 200                 205

Val Gly Ile Met Gly Pro Glu Lys Lys Asn Ser Met Ala Asp Tyr Trp
    210                 215                 220

Val His His Gly Lys Gly Leu Ala Val Asp Ile Ile Glu Thr Glu Met
225                 230                 235                 240

Gln Lys Leu Ala Pro Phe Pro
                245
```

<210> SEQ ID NO 73
<211> LENGTH: 954
<212> TYPE: DNA
<213> ORGANISM: Arabidopsis thaliana

<400> SEQUENCE: 73

```
atggcgactc ttaaggtttc tgattctgtt cctgctcctt ctgatgatgc tgagcaattg      60

agaaccgctt ttgaaggatg gggtacgaac gaggacttga tcatatcaat cttggctcac     120

agaagtgctg aacagaggaa agtcatcagg caagcatacc acgaaaccta cggcgaagac     180

cttctcaaga ctcttgacaa ggagctctct aacgatttcg agagagctat cttgttgtgg     240

actcttgaac ccggtgagcg tgatgcttta ttggctaatg aagctacaaa aagatggact     300

tcaagcaacc aagttcttat ggaagttgct tgcacaagga catcaacgca gctgcttcac     360

gctaggcaag cttaccatgc tcgctacaag aagtctcttg aagaggacgt tgctcaccac     420

actaccggtg acttcagaaa gcttttggtt tctcttgtta cctcatacag gtacgaagga     480

gatgaagtga acatgacatt ggctaagcaa gaagctaagc tggtccatga gaaaatcaag     540

gacaagcact acaatgatga ggatgttatt agaatcttgt ccacaagaag caaagctcag     600

atcaatgcta cttttaaccg ttaccaagat gatcatggcg aggaaattct caagagtctt     660

gaggaaggag atgatgatga caagttcctt gcacttttga ggtcaaccat tcagtgcttg     720

acaagaccag agctttactt tgtcgatgtt cttcgttcag caatcaacaa aactggaact     780

gatgaaggag cactcactag aattgtgacc acaagagctg agattgactt gaaggtcatt     840

ggagaggagt accagcgcag gaacagcatt cctttggaga aagctattac caaagacact     900

cgtggagatt acgagaagat gctcgtcgca cttctcggtg aagatgatgc ttaa           954
```

<210> SEQ ID NO 74
<211> LENGTH: 317
<212> TYPE: PRT
<213> ORGANISM: Arabidopsis thaliana

<400> SEQUENCE: 74

```
Met Ala Thr Leu Lys Val Ser Asp Ser Val Pro Ala Pro Ser Asp Asp
1               5                   10                  15

Ala Glu Gln Leu Arg Thr Ala Phe Glu Gly Trp Gly Thr Asn Glu Asp
            20                  25                  30

Leu Ile Ile Ser Ile Leu Ala His Arg Ser Ala Glu Gln Arg Lys Val
        35                  40                  45

Ile Arg Gln Ala Tyr His Glu Thr Tyr Gly Glu Asp Leu Leu Lys Thr
    50                  55                  60

Leu Asp Lys Glu Leu Ser Asn Asp Phe Glu Arg Ala Ile Leu Leu Trp
65                  70                  75                  80

Thr Leu Glu Pro Gly Glu Arg Asp Ala Leu Leu Ala Asn Glu Ala Thr
                85                  90                  95

Lys Arg Trp Thr Ser Ser Asn Gln Val Leu Met Glu Val Ala Cys Thr
            100                 105                 110

Arg Thr Ser Thr Gln Leu Leu His Ala Arg Gln Ala Tyr His Ala Arg
        115                 120                 125

Tyr Lys Lys Ser Leu Glu Glu Asp Val Ala His His Thr Thr Gly Asp
    130                 135                 140

Phe Arg Lys Leu Leu Val Ser Leu Val Thr Ser Tyr Arg Tyr Glu Gly
145                 150                 155                 160

Asp Glu Val Asn Met Thr Leu Ala Lys Gln Glu Ala Lys Leu Val His
                165                 170                 175

Glu Lys Ile Lys Asp Lys His Tyr Asn Asp Glu Asp Val Ile Arg Ile
            180                 185                 190

Leu Ser Thr Arg Ser Lys Ala Gln Ile Asn Ala Thr Phe Asn Arg Tyr
        195                 200                 205

Gln Asp Asp His Gly Glu Glu Ile Leu Lys Ser Leu Glu Glu Gly Asp
    210                 215                 220

Asp Asp Asp Lys Phe Leu Ala Leu Leu Arg Ser Thr Ile Gln Cys Leu
225                 230                 235                 240

Thr Arg Pro Glu Leu Tyr Phe Val Asp Val Leu Arg Ser Ala Ile Asn
                245                 250                 255

Lys Thr Gly Thr Asp Glu Gly Ala Leu Thr Arg Ile Val Thr Thr Arg
            260                 265                 270

Ala Glu Ile Asp Leu Lys Val Ile Gly Glu Glu Tyr Gln Arg Arg Asn
        275                 280                 285

Ser Ile Pro Leu Glu Lys Ala Ile Thr Lys Asp Thr Arg Gly Asp Tyr
    290                 295                 300

Glu Lys Met Leu Val Ala Leu Leu Gly Glu Asp Asp Ala
305                 310                 315
```

<210> SEQ ID NO 75
<211> LENGTH: 1170
<212> TYPE: DNA
<213> ORGANISM: Arabidopsis thaliana

<400> SEQUENCE: 75

```
atggtggatc tattgaactc ggtgatgaac ctggtggcgc ctccagcgac catggtggtg      60

atggcctttg catggccatt actgtctttc attagcttct ccgaacgggc ttacaactct     120
```

```
tatttcgcca ccgaaaatat ggaagataaa gtagttgtca tcaccggagc ttcatcggcc    180

attggagagc aaatagcata tgaatatgca aaaagaggag cgaatttggt gttggtggcg    240

aggagagagc agagactgag agttgtgagt aataaggcta aacagattgg agccaaccat    300

gtgatcatca tcgctgctga tgtcatcaaa gaagatgact gccgccgttt tatcacccaa    360

gccgtcaact attacggccg cgtggatcat ctagtgaata cagcgagtct tggacacact    420

ttttactttg aggaagtgag tgacacgact gtgtttccac atttgctgga cataaacttc    480

tggggaatg tttatccgac atacgtagcg ttgccatacc ttcaccagac gaatggccga     540

atagtcgtga atgcatcggt tgaaaactgg ttgcctctac cacggatgag tctttattct    600

gctgcaaaag cagcattagt caacttctat gagacgctgc gtttcgagct aaatggagac    660

gttggtataa ctatcgcgac tcacgggtgg attggcagtg agatgagtgg aggaaagttc    720

atgctagaag aaggtgctga gatgcaatgg aaggaagaga gagaagtacc tgcaaatggt    780

ggaccgctag aggaatttgc aaagatgatt gtggcaggag cttgtagggg agatgcatat    840

gtgaagtttc caaactggta cgatgtcttt ctcctctatc gagtcttcac accgaatgta    900

ctgagatgga cattcaagtt gttactgtct actgagggta cacgtagaag ctcccttgtt    960

ggggtcgggt caggtatgcc tgtggatgaa tcctcttcac aaatgaaact tatgcttgaa   1020

ggaggaccac ctcgagttcc tgcaagccca cctaggtata ccgcaagccc acctcattat   1080

accgcaagcc caccacggta tcctgcaagc ccacctcggt atcctgcgag cccacctcgg   1140

ttttcacagt ttaatatcca agagttgtaa                                    1170
```

```
<210> SEQ ID NO 76
<211> LENGTH: 389
<212> TYPE: PRT
<213> ORGANISM: Arabidopsis thaliana

<400> SEQUENCE: 76

Met Val Asp Leu Leu Asn Ser Val Met Asn Leu Val Ala Pro Pro Ala
1               5                   10                  15

Thr Met Val Val Met Ala Phe Ala Trp Pro Leu Leu Ser Phe Ile Ser
            20                  25                  30

Phe Ser Glu Arg Ala Tyr Asn Ser Tyr Phe Ala Thr Glu Asn Met Glu
        35                  40                  45

Asp Lys Val Val Val Ile Thr Gly Ala Ser Ser Ala Ile Gly Glu Gln
    50                  55                  60

Ile Ala Tyr Glu Tyr Ala Lys Arg Gly Ala Asn Leu Val Leu Val Ala
65                  70                  75                  80

Arg Arg Glu Gln Arg Leu Arg Val Val Ser Asn Lys Ala Lys Gln Ile
                85                  90                  95

Gly Ala Asn His Val Ile Ile Ile Ala Ala Asp Val Ile Lys Glu Asp
            100                 105                 110

Asp Cys Arg Arg Phe Ile Thr Gln Ala Val Asn Tyr Tyr Gly Arg Val
        115                 120                 125

Asp His Leu Val Asn Thr Ala Ser Leu Gly His Thr Phe Tyr Phe Glu
    130                 135                 140

Glu Val Ser Asp Thr Thr Val Phe Pro His Leu Leu Asp Ile Asn Phe
145                 150                 155                 160

Trp Gly Asn Val Tyr Pro Thr Tyr Val Ala Leu Pro Tyr Leu His Gln
                165                 170                 175

Thr Asn Gly Arg Ile Val Val Asn Ala Ser Val Glu Asn Trp Leu Pro
            180                 185                 190
```

```
Leu Pro Arg Met Ser Leu Tyr Ser Ala Ala Lys Ala Ala Leu Val Asn
        195                 200                 205

Phe Tyr Glu Thr Leu Arg Phe Glu Leu Asn Gly Asp Val Gly Ile Thr
    210                 215                 220

Ile Ala Thr His Gly Trp Ile Gly Ser Glu Met Ser Gly Gly Lys Phe
225                 230                 235                 240

Met Leu Glu Glu Gly Ala Glu Met Gln Trp Lys Glu Glu Arg Glu Val
                245                 250                 255

Pro Ala Asn Gly Gly Pro Leu Glu Glu Phe Ala Lys Met Ile Val Ala
            260                 265                 270

Gly Ala Cys Arg Gly Asp Ala Tyr Val Lys Phe Pro Asn Trp Tyr Asp
        275                 280                 285

Val Phe Leu Leu Tyr Arg Val Phe Thr Pro Asn Val Leu Arg Trp Thr
    290                 295                 300

Phe Lys Leu Leu Leu Ser Thr Glu Gly Thr Arg Arg Ser Ser Leu Val
305                 310                 315                 320

Gly Val Gly Ser Gly Met Pro Val Asp Glu Ser Ser Ser Gln Met Lys
                325                 330                 335

Leu Met Leu Glu Gly Gly Pro Pro Arg Val Pro Ala Ser Pro Pro Arg
            340                 345                 350

Tyr Thr Ala Ser Pro Pro His Tyr Thr Ala Ser Pro Pro Arg Tyr Pro
        355                 360                 365

Ala Ser Pro Pro Arg Tyr Pro Ala Ser Pro Pro Arg Phe Ser Gln Phe
    370                 375                 380

Asn Ile Gln Glu Leu
385
```

<210> SEQ ID NO 77
<211> LENGTH: 990
<212> TYPE: DNA
<213> ORGANISM: Arabidopsis thaliana

<400> SEQUENCE: 77

```
atggctggaa aactcatgca cgctcttcag tacaactctt acggtggtgg cgccgccgga     60

ttagagcatg ttcaagttcc ggttccaaca ccaaagagta atgaggtttg cctgaaatta    120

gaagctacta gtctaaaccc tgttgattgg aaaattcaga aaggaatgat ccgcccattt    180

ctgccccgca agttcccctg cattccagct actgatgttg ctggagaggt cgttgaggtt    240

ggatcaggag taaaaaattt taaggctggt gacaaagttg tagcggttct tagccatcta    300

ggtggaggtg gacttgctga gttcgctgtt gcaaccgaga agctgactgt caaaagacct    360

caagaagtgg gagcagctga agcagcagct ttacctgtgg cgggtctaac cgctctccaa    420

gctcttacta atcctgcggg gttgaagctg gatggtacag gcaagaaggc gaacatcctg    480

gtcacagcag catctggtgg ggttggtcac tatgcagtcc agctggcaaa acttgcaaat    540

gctcacgtaa ccgctacatg tggtgcccgg aacatagagt ttgtcaaatc gttgggagcg    600

gatgaggttc tcgactacaa gactcccgag ggagccgccc tcaagagtcc gtcgggtaaa    660

aaatatgacg ctgtggtcca ttgtgcaaac gggattccat tttcggtatt cgaaccaaat    720

ttgtcggaaa acgggaaggt gatagacatc acaccggggc ctaatgcaat gtggacttat    780

gcggttaaga aaataaccat gtcaaagaag cagttagtgc cactcttgtt gatcccaaaa    840

gctgagaatt tggagtttat ggtgaatcta gtgaaagaag ggaaagtgaa gacagtgatt    900

gactcaaagc atcctttgag caaagcggag gatgcttggg ccaaaagtat cgatggtcat    960
```

```
gctactggga agatcattgt cgagccataa                                   990


<210> SEQ ID NO 78
<211> LENGTH: 329
<212> TYPE: PRT
<213> ORGANISM: Arabidopsis thaliana

<400> SEQUENCE: 78

Met Ala Gly Lys Leu Met His Ala Leu Gln Tyr Asn Ser Tyr Gly Gly
1               5                   10                  15

Gly Ala Ala Gly Leu Glu His Val Gln Val Pro Val Pro Thr Pro Lys
            20                  25                  30

Ser Asn Glu Val Cys Leu Lys Leu Glu Ala Thr Ser Leu Asn Pro Val
        35                  40                  45

Asp Trp Lys Ile Gln Lys Gly Met Ile Arg Pro Phe Leu Pro Arg Lys
    50                  55                  60

Phe Pro Cys Ile Pro Ala Thr Asp Val Ala Gly Glu Val Val Glu Val
65                  70                  75                  80

Gly Ser Gly Val Lys Asn Phe Lys Ala Gly Asp Lys Val Val Ala Val
                85                  90                  95

Leu Ser His Leu Gly Gly Gly Gly Leu Ala Glu Phe Ala Val Ala Thr
            100                 105                 110

Glu Lys Leu Thr Val Lys Arg Pro Gln Glu Val Gly Ala Ala Glu Ala
        115                 120                 125

Ala Ala Leu Pro Val Ala Gly Leu Thr Ala Leu Gln Ala Leu Thr Asn
    130                 135                 140

Pro Ala Gly Leu Lys Leu Asp Gly Thr Gly Lys Lys Ala Asn Ile Leu
145                 150                 155                 160

Val Thr Ala Ala Ser Gly Gly Val Gly His Tyr Ala Val Gln Leu Ala
                165                 170                 175

Lys Leu Ala Asn Ala His Val Thr Ala Thr Cys Gly Ala Arg Asn Ile
            180                 185                 190

Glu Phe Val Lys Ser Leu Gly Ala Asp Glu Val Leu Asp Tyr Lys Thr
        195                 200                 205

Pro Glu Gly Ala Ala Leu Lys Ser Pro Ser Gly Lys Lys Tyr Asp Ala
    210                 215                 220

Val Val His Cys Ala Asn Gly Ile Pro Phe Ser Val Phe Glu Pro Asn
225                 230                 235                 240

Leu Ser Glu Asn Gly Lys Val Ile Asp Ile Thr Pro Gly Pro Asn Ala
                245                 250                 255

Met Trp Thr Tyr Ala Val Lys Lys Ile Thr Met Ser Lys Lys Gln Leu
            260                 265                 270

Val Pro Leu Leu Leu Ile Pro Lys Ala Glu Asn Leu Glu Phe Met Val
        275                 280                 285

Asn Leu Val Lys Glu Gly Lys Val Lys Thr Val Ile Asp Ser Lys His
    290                 295                 300

Pro Leu Ser Lys Ala Glu Asp Ala Trp Ala Lys Ser Ile Asp Gly His
305                 310                 315                 320

Ala Thr Gly Lys Ile Ile Val Glu Pro
                325


<210> SEQ ID NO 79
<211> LENGTH: 1389
<212> TYPE: DNA
<213> ORGANISM: Physcomitrella patens

<400> SEQUENCE: 79
```

```
atggaaattc ccttaggtcg agatggcgag ggtatgcagt caaagcagtg cccgcgcggc     60
cactggcgtc cagcggaaga cgacaagctg cgagaactag tgtcccagtt tggacctcaa    120
aactggaatc tcatagcaga gaaacttcag ggtcgatcag ggaaaagctg caggctacgg    180
tggttcaatc agctggaccc tcgcatcaac cggcacccat tctcggaaga agaggaagag    240
cggctgctta tagcacacaa gcgctacggc aacaagtggg cattgatcgc gcgcctcttt    300
ccgggccgca cagacaacgc ggtgaagaat cactggcacg ttgtgacggc aagacagtcc    360
cgtgaacgga cacgaactta cggccgtatc aaaggtccgg tacatcgaag aggcaagggt    420
aaccgtatca atacctccgc acttggaaat taccatcacg attcgaaggg agctctcaca    480
gcctggattg agtcgaagta tgcgacagtc gagcagtctg cggaagggct cgctaggtct    540
ccttgtaccg gcagaggctc tcctcctcta cccaccggtt tcagtatacc gcagatttcc    600
ggcggcgcct tccatcgacc gacaaacatg agtactagtc ctcttagcga tgtgactatc    660
gagtcgccaa agtttagcaa ctccgaaaat gcgcaaataa taaccgcgcc cgtcctgcaa    720
aagccaatgg gagatcccag gtcagtatgc ttgccgaatt cgactgtttc cgacaagcag    780
caagtgctgc agagtaattc catcgacggt cagatctcct ccgggctcca gacaagcgca    840
atagtagcgc atgatgagaa atcgggcgtc atttcaatga atcatcaagc accggatatg    900
tcctgtgttg gattgaagtc aaattttcag gggagtctcc atcctggcgc tgttagatct    960
tcttggaatc aatcccttcc ccactgtttt ggccacagta acaagttggt ggaggagtgc   1020
aggagttcta caggcgcatg cactgaacgc tctgagattc tgcaagaaca gcattctagc   1080
cttcagttta aatgcagcac tgcgtacaat actggaagat atcaacatga aaacctttgt   1140
gggccagcat tctcgcaaca agacacagcg aacgaggttg cgaatttttc tacgttggca   1200
ttctccggcc tagtgaagca tcgccaagag aggttgtgca aagatagtgg atctgctctc   1260
aagctgggac tatcatgggt tacatccgat agcactcttg acttgagtgt tgccaaaatg   1320
tcagcatcgc agccagagca gtctgcgccg gttgcattca ttgattttct aggcgtggga   1380
gcggcctga                                                            1389
```

<210> SEQ ID NO 80
<211> LENGTH: 462
<212> TYPE: PRT
<213> ORGANISM: Physcomitrella patens

<400> SEQUENCE: 80

```
Met Glu Ile Pro Leu Gly Arg Asp Gly Glu Gly Met Gln Ser Lys Gln
1               5                   10                  15

Cys Pro Arg Gly His Trp Arg Pro Ala Glu Asp Asp Lys Leu Arg Glu
            20                  25                  30

Leu Val Ser Gln Phe Gly Pro Gln Asn Trp Asn Leu Ile Ala Glu Lys
        35                  40                  45

Leu Gln Gly Arg Ser Gly Lys Ser Cys Arg Leu Arg Trp Phe Asn Gln
    50                  55                  60

Leu Asp Pro Arg Ile Asn Arg His Pro Phe Ser Glu Glu Glu Glu Glu
65                  70                  75                  80

Arg Leu Leu Ile Ala His Lys Arg Tyr Gly Asn Lys Trp Ala Leu Ile
                85                  90                  95

Ala Arg Leu Phe Pro Gly Arg Thr Asp Asn Ala Val Lys Asn His Trp
            100                 105                 110

His Val Val Thr Ala Arg Gln Ser Arg Glu Arg Thr Arg Thr Tyr Gly
        115                 120                 125
```

```
Arg Ile Lys Gly Pro Val His Arg Arg Gly Lys Gly Asn Arg Ile Asn
    130                 135                 140

Thr Ser Ala Leu Gly Asn Tyr His His Asp Ser Lys Gly Ala Leu Thr
145                 150                 155                 160

Ala Trp Ile Glu Ser Lys Tyr Ala Thr Val Glu Gln Ser Ala Glu Gly
                165                 170                 175

Leu Ala Arg Ser Pro Cys Thr Gly Arg Gly Ser Pro Pro Leu Pro Thr
            180                 185                 190

Gly Phe Ser Ile Pro Gln Ile Ser Gly Gly Ala Phe His Arg Pro Thr
        195                 200                 205

Asn Met Ser Thr Ser Pro Leu Ser Asp Val Thr Ile Glu Ser Pro Lys
    210                 215                 220

Phe Ser Asn Ser Glu Asn Ala Gln Ile Ile Thr Ala Pro Val Leu Gln
225                 230                 235                 240

Lys Pro Met Gly Asp Pro Arg Ser Val Cys Leu Pro Asn Ser Thr Val
                245                 250                 255

Ser Asp Lys Gln Gln Val Leu Gln Ser Asn Ser Ile Asp Gly Gln Ile
            260                 265                 270

Ser Ser Gly Leu Gln Thr Ser Ala Ile Val Ala His Asp Glu Lys Ser
        275                 280                 285

Gly Val Ile Ser Met Asn His Gln Ala Pro Asp Met Ser Cys Val Gly
    290                 295                 300

Leu Lys Ser Asn Phe Gln Gly Ser Leu His Pro Gly Ala Val Arg Ser
305                 310                 315                 320

Ser Trp Asn Gln Ser Leu Pro His Cys Phe Gly His Ser Asn Lys Leu
                325                 330                 335

Val Glu Glu Cys Arg Ser Ser Thr Gly Ala Cys Thr Glu Arg Ser Glu
            340                 345                 350

Ile Leu Gln Glu Gln His Ser Ser Leu Gln Phe Lys Cys Ser Thr Ala
        355                 360                 365

Tyr Asn Thr Gly Arg Tyr Gln His Glu Asn Leu Cys Gly Pro Ala Phe
    370                 375                 380

Ser Gln Gln Asp Thr Ala Asn Glu Val Ala Asn Phe Ser Thr Leu Ala
385                 390                 395                 400

Phe Ser Gly Leu Val Lys His Arg Gln Glu Arg Leu Cys Lys Asp Ser
                405                 410                 415

Gly Ser Ala Leu Lys Leu Gly Leu Ser Trp Val Thr Ser Asp Ser Thr
            420                 425                 430

Leu Asp Leu Ser Val Ala Lys Met Ser Ala Ser Gln Pro Glu Gln Ser
        435                 440                 445

Ala Pro Val Ala Phe Ile Asp Phe Leu Gly Val Gly Ala Ala
    450                 455                 460
```

<210> SEQ ID NO 81
<211> LENGTH: 963
<212> TYPE: DNA
<213> ORGANISM: Arabidopsis thaliana

<400> SEQUENCE: 81

```
atggagatga acattaagtt tccagttata gacttgtcta agctcaatgg tgaagagaga     60

gaccaaacca tggctttgat cgacgatgct tgtcaaaact ggggcttctt cgagctggtg    120

aaccatggac taccatatga tctaatggac aacattgaga ggatgacaaa ggaacactac    180

aagaaacata tggaacaaaa gttcaaagaa atgcttcgtt ccaaaggttt agataccctc    240
```

```
gagaccgaag ttgaagatgt cgattgggaa agcactttct acctccatca tctccctcaa    300

tctaacctat acgacatccc tgatatgtca aatgaatacc gattggcaat gaaggatttt    360

gggaagaggc ttgagattct agctgaagag ctattggact tgttgtgtga gaatctaggg    420

ttggagaaag ggtacttgaa gaaggtgttt catgggacaa cgggtccaac ttttgcgaca    480

aagcttagca actatccacc atgtcctaaa ccagagatga tcaaagggct tagggctcac    540

acagatgcag gaggcctcat tttgctgttt caagatgata aggtcagtgg tctccagctt    600

cttaaagatg gtgattgggt tgatgttcct cctctcaagc attccattgt catcaacctt    660

ggtgaccaac ttgaggtgat aacaaacggg aagtacaaga gtgtaatgca ccgtgtgatg    720

acccagaaag aaggaaacag gatgtctatc gcgtcgtttt acaaccccgg aagcgatgct    780

gagatctctc cggcaacatc tcttgtggat aaagactcaa aatacccaag ctttgtgttt    840

gatgactaca tgaaactcta tgccggactc aagtttcagg ccaaggagcc acggttcgag    900

gcgatgaaaa atgctgaagc agctgcggat ttgaatccgg tggctgtggt tgagacattc    960

taa                                                                  963
```

<210> SEQ ID NO 82
<211> LENGTH: 320
<212> TYPE: PRT
<213> ORGANISM: Arabidopsis thaliana

<400> SEQUENCE: 82

```
Met Glu Met Asn Ile Lys Phe Pro Val Ile Asp Leu Ser Lys Leu Asn
1               5                   10                  15

Gly Glu Glu Arg Asp Gln Thr Met Ala Leu Ile Asp Asp Ala Cys Gln
            20                  25                  30

Asn Trp Gly Phe Phe Glu Leu Val Asn His Gly Leu Pro Tyr Asp Leu
        35                  40                  45

Met Asp Asn Ile Glu Arg Met Thr Lys Glu His Tyr Lys Lys His Met
    50                  55                  60

Glu Gln Lys Phe Lys Glu Met Leu Arg Ser Lys Gly Leu Asp Thr Leu
65                  70                  75                  80

Glu Thr Glu Val Glu Asp Val Asp Trp Glu Ser Thr Phe Tyr Leu His
                85                  90                  95

His Leu Pro Gln Ser Asn Leu Tyr Asp Ile Pro Asp Met Ser Asn Glu
            100                 105                 110

Tyr Arg Leu Ala Met Lys Asp Phe Gly Lys Arg Leu Glu Ile Leu Ala
        115                 120                 125

Glu Glu Leu Leu Asp Leu Leu Cys Glu Asn Leu Gly Leu Glu Lys Gly
    130                 135                 140

Tyr Leu Lys Lys Val Phe His Gly Thr Thr Gly Pro Thr Phe Ala Thr
145                 150                 155                 160

Lys Leu Ser Asn Tyr Pro Pro Cys Pro Lys Pro Glu Met Ile Lys Gly
                165                 170                 175

Leu Arg Ala His Thr Asp Ala Gly Gly Leu Ile Leu Leu Phe Gln Asp
            180                 185                 190

Asp Lys Val Ser Gly Leu Gln Leu Leu Lys Asp Gly Asp Trp Val Asp
        195                 200                 205

Val Pro Pro Leu Lys His Ser Ile Val Ile Asn Leu Gly Asp Gln Leu
    210                 215                 220

Glu Val Ile Thr Asn Gly Lys Tyr Lys Ser Val Met His Arg Val Met
225                 230                 235                 240

Thr Gln Lys Glu Gly Asn Arg Met Ser Ile Ala Ser Phe Tyr Asn Pro
```

```
            245                 250                 255

Gly Ser Asp Ala Glu Ile Ser Pro Ala Thr Ser Leu Val Asp Lys Asp
            260                 265                 270

Ser Lys Tyr Pro Ser Phe Val Phe Asp Asp Tyr Met Lys Leu Tyr Ala
        275                 280                 285

Gly Leu Lys Phe Gln Ala Lys Glu Pro Arg Phe Glu Ala Met Lys Asn
    290                 295                 300

Ala Glu Ala Ala Ala Asp Leu Asn Pro Val Ala Val Val Glu Thr Phe
305                 310                 315                 320


<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 83

atggcgcgcc atggcaatct tccgaagtac actagt                              36


<210> SEQ ID NO 84
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 84

gcttaattaa ttaagggcac ttgagacggc ca                                  32


<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 85

atggcgcgcc aacaatggag aatggagcaa cgacg                               35


<210> SEQ ID NO 86
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 86

gcttaattaa ctatatggtt ggatattgag tcttggc                             37


<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 87

atggcgcgcc atggctgaaa aagtaaagtc tggtca                              36


<210> SEQ ID NO 88
<211> LENGTH: 34
<212> TYPE: DNA
<213> ORGANISM: Artificial Sequence
<220> FEATURE:
```

<223> OTHER INFORMATION: Description of Artificial Sequence: Primer

<400> SEQUENCE: 88
gcttaattaa ttatagctcc tcagatccct ccga 34

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 89
atggcgcgcc atggctggag aagaaataga gaggg 35

<210> SEQ ID NO 90
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 90
gcttaattaa ttaaacagag gcttctctac tctcactt 38

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 91
atggcgcgcc atggctggag tgatgaagtt ggc 33

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 92
gcttaattaa tcacctcacg gtgttgcagt tg 32

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 93
atggcgcgcc aaacaatggg gcttgctgtg gtgg 34

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 94
gcttaattaa ttactgcaag gctttcaata tatttc 36

<210> SEQ ID NO 95

<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 95
atggcgcgcc aacaatggcg ttcacggcgc ttgt 34

<210> SEQ ID NO 96
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 96
gcttaattaa tcaacaagta ggataaggaa caccaca 37

<210> SEQ ID NO 97
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 97
atggcgcgcc aacaatggcc cttgatgagc ttctcaag 38

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 98
gcttaattaa tcagagagaa gcagagtttg ttcgc 35

<210> SEQ ID NO 99
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 99
atggcgcgcc aacaatggcg caatcccgat tattag 36

<210> SEQ ID NO 100
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 100
gcttaattaa ttaaaaccac tcgcctctca tttc 34

<210> SEQ ID NO 101
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 101
atggcgcgcc atgtccgtgg ctcgattcga t 31

<210> SEQ ID NO 102
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 102
gcttaattaa ctaatcctct agctcgatga ttttgac 37

<210> SEQ ID NO 103
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 103
atggcgcgcc aacaatggcg atttacagat ctctaagaaa g 41

<210> SEQ ID NO 104
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 104
gcttaattaa ttaccttaga taagtgatcc atgtctgg 38

<210> SEQ ID NO 105
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 105
atggcgcgcc aacaatggta aaggaaactc taattcctcc g 41

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 106
gcttaattaa ctaccagccg aagattggct tgt 33

<210> SEQ ID NO 107
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 107
atggcgcgcc atttggagag caatggcgac tt 32

<210> SEQ ID NO 108
<211> LENGTH: 34
<212> TYPE: DNA
<213> ORGANISM: Artificial Sequence
<220> FEATURE:

<223> OTHER INFORMATION: Description of Artificial Sequence: Primer

<400> SEQUENCE: 108
gcttaattaa ttacatcgaa cgaagaagca tcaa 34

<210> SEQ ID NO 109
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 109
atggcgcgcc catcctcaga aagaatggct caaa 34

<210> SEQ ID NO 110
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 110
gcttaattaa ttagctttct tcaccatcat cggtg 35

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 111
atggcgcgcc aacaatgggt gcaggtggaa gaatgcc 37

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 112
gcttaattaa tcataactta ttgttgtacc agtacacacc 40

<210> SEQ ID NO 113
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 113
atggcgcgcc aacaatggct tcaataaatg aagatgtgtc t 41

<210> SEQ ID NO 114
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 114
gacttaatta atcaattggt gggattaacg actcca 36

<210> SEQ ID NO 115

<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 115
atggcgcgcc aacaatggct acattctctt gtaattctta tga 43

<210> SEQ ID NO 116
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 116
gacttaatta atcagaagcg gccattaaaa ttaccca 37

<210> SEQ ID NO 117
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 117
ataagaatgc ggccgccatg gcaacggaat gcattgca 38

<210> SEQ ID NO 118
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 118
ataagaatgc ggccgcttag aaacttcttc tgttctt 37

<210> SEQ ID NO 119
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 119
ataagaatgc ggccgccatg gcgtcagagc aagcaagg 38

<210> SEQ ID NO 120
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 120
ataagaatgc ggccgctcaa cgttgtccat gttcccg 37

<210> SEQ ID NO 121
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 121
ataagaatgc ggccgccatg gctaagtctt gctatttca 39

<210> SEQ ID NO 122
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 122
ataagaatgc ggccgctcag gcgctatagc ctaagatt 38

<210> SEQ ID NO 123
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 123
ataagaatgc ggccgccatg gacggtgccg gagaatcacg a 41

<210> SEQ ID NO 124
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 124
ataagaatgc ggccgcctaa taacttaaag ttaccgga 38

<210> SEQ ID NO 125
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 125
ataagaatgc ggccgccatg tcgagagctt tgtcagtcg 39

<210> SEQ ID NO 126
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 126
ataagaatgc ggccgccatg tcgagagctt tgtcagtcg 39

<210> SEQ ID NO 127
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 127
ataagaatgc ggccgccatg gcaagcagcg acgtgaagct 40

<210> SEQ ID NO 128
<211> LENGTH: 38
<212> TYPE: DNA
<213> ORGANISM: Artificial Sequence
<220> FEATURE:

<223> OTHER INFORMATION: Description of Artificial Sequence: Primer

<400> SEQUENCE: 128
ataagaatgc ggccgctcaa ccaagccaag aagcaccc 38

<210> SEQ ID NO 129
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 129
ataagaatgc ggccgccatg gcgtctcaac aagagaaga 39

<210> SEQ ID NO 130
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 130
ataagaatgc ggccgcttag gtcttggtcc tgaatttg 38

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 131
ggttaattaa ggcgcgcccc cggaagcgat gctgag 36

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 132
atctcgagga cgtcccacag ccaccggatt c 31

<210> SEQ ID NO 133
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 133
ataagaatgc ggccgccatg gctccttcaa caaaagttc 39

<210> SEQ ID NO 134
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 134
ataagaatgc ggccgctcaa acactgctga tagtattt 38

<210> SEQ ID NO 135

<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 135
ataagaatgc ggccgccatg cggtgctttc cacctccct 39

<210> SEQ ID NO 136
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 136
ataagaatgc ggccgcttac ttttgtaatg gtgagagc 38

<210> SEQ ID NO 137
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 137
ataagaatgc ggccgccatg cttctaattc tagcgattt 39

<210> SEQ ID NO 138
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 138
ataagaatgc ggccgctcag ataaccttct tcttctcg 38

<210> SEQ ID NO 139
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 139
attgcggccg cacaatggca catgccacgt ttacg 35

<210> SEQ ID NO 140
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 140
attgcggccg cttagtcttc atggtcccat agatc 35

<210> SEQ ID NO 141
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 141
gcggccgcca tggcgtctga gaaacaaaaa c 31

<210> SEQ ID NO 142
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 142
aggcctttac gcatttacca cagctcc 27

<210> SEQ ID NO 143
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 143
gcggccgcat ggattcaacg aagcttagtg agc 33

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 144
aggcctttac tgaggtcctg caaatttg 28

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 145
gcggccgcca tgaaggttca cgagacaaga 30

<210> SEQ ID NO 146
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 146
aggcctctac tctggttcga catcgac 27

<210> SEQ ID NO 147
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 147
gcggccgcca tgtctacccc agctgaatc 29

<210> SEQ ID NO 148
<211> LENGTH: 27
<212> TYPE: DNA
<213> ORGANISM: Artificial Sequence
<220> FEATURE:

<223> OTHER INFORMATION: Description of Artificial Sequence: Primer

<400> SEQUENCE: 148
aggcctctaa ttgtagagat catcatc 27

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 149
gcggccgcca tggacaaatc tagtaccatg 30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 150
aggccttcag ctaccaccct tttgtttgag 30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 151
gcggccgcca tggcgaaatc tcagatctgg 30

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 152
aggcctttaa gaagaagcaa cgaacgtg 28

<210> SEQ ID NO 153
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 153
gcggccgcca tggcgtcgag cgatgagcg 29

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 154
gatatcttac gggaacggag ccaatttc 28

<210> SEQ ID NO 155

<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 155
gcggccgcca tggcgactct taaggtttct g 31

<210> SEQ ID NO 156
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 156
aggcctttaa gcatcatctt caccgag 27

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 157
gcggccgcca tggtggatct attgaactcg 30

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 158
aggcctttac aactcttgga tattaaac 28

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 159
gcggccgcca tggctggaaa actcatgcac 30

<210> SEQ ID NO 160
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 160
aggcctttat ggctcgacaa tgatcttc 28

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 161

```
caggaaacag ctatgacc                                               18


<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 162

ctaaagggaa caaaagctg                                              19


<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 163

tgtaaaacga cggccagt                                               18
```

SUGAR AND LIPID METABOLISM REGULATORS IN PLANTS IV

CROSS REFERENCE TO RELATED APPLICATIONS

This application is a divisional application of U.S. application Ser. No. 10/523,503 filed Jul. 13, 2005, which is a national stage application (under 35 U.S.C. §371) of PCT/US2003/24364 filed Aug. 4, 2003, which claims benefit U.S. Provisional Patent Application Ser. No. 60/400,803 filed Aug. 2, 2002. The entire contents of each of these applications are hereby incorporated by reference herein.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List__12810__01083_US. The size of the text file is 207 KB, and the text file was created on Nov. 8, 2010.

BACKGROUND OF THE INVENTION

1. Field of the Invention

This invention relates generally to nucleic acid sequences encoding proteins that are related to the presence of seed storage compounds in plants. More specifically, the present invention relates to nucleic acid sequences encoding sugar and lipid metabolism regulator proteins and the use of these sequences in transgenic plants. The invention further relates to methods of applying these novel plant polypeptides to the identification and stimulation of plant growth and/or to the increase of yield of seed storage compounds.

2. Background Art

The study and genetic manipulation of plants has a long history that began even before the framed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al., 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164), rapeseed (Töpfer et al., 1995, Science 268:681-686), and non-traditional oil seed plants such as tobacco (Cahoon et al., 1992, Proc. Natl. Acad. Sci. USA 89:11184-11188).

Plant seed oils comprise both neutral and polar lipids (See Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes, and the cell membrane. The neutral and polar lipids contain several common fatty acids (See Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al., 1993, Unusual Fatty Acids in Lipid Metabolism in Plants pp. 91-126, editor T S Moore Jr. CRC Press; Millar et al., 2000, Trends Plant Sci. 5:95-101).

TABLE 1

| Plant Lipid Classes | |
|---|---|
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

| Common Plant Fatty Acids | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid * |
| 20:0 | Arachidic acid |
| 20:1 | Eicosenoic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

In Table 2, the fatty acids denoted with an asterisk do not normally occur in plant seed oils, but their production in transgenic plant seed oil is of importance in plant biotechnology.

Lipids are synthesized from fatty acids, and their synthesis may be divided into two parts: the prokaryotic pathway and the eukaryotic pathway (Browse et al., 1986, Biochemical J. 235:25-31; Ohlrogge & Browse, 1995, Plant Cell 7:957-970). The prokaryotic pathway is located in plastids, the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction in which the acyl group from acetyl-CoA is transferred to malonyl-ACP to form 3-ketobutyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16-carbon or 18-carbon saturated fatty acid chain is formed. The plastidial delta-9 acyl-ACP desaturase introduces the first unsaturated double bond into the fatty acid. Thioesterases cleave the fatty acids from the ACP cofactor, and free fatty acids are exported to the cytoplasm where they participate as fatty acyl-CoA esters in the eukaryotic pathway. In the eukaryotic pathway, the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker, 1996, Genetic Engineering ed. Setlow 18:111-113; Shanklin & Cahoon, 1998, Annu. Rev. Plant Physiol. Plant Mol. Biol. 49:611-641; Frentzen, 1998, Lipids 100:161-166; Millar et al., 2000, Trends Plant Sci. 5:95-101).

Storage lipids in seeds are synthesized from carbohydrate-derived precursors. Plants have a complete glycolytic pathway in the cytosol (Plaxton, 1996, Annu. Rev. Plant Physiol. Plant Mol. Biol. 47:185-214), and it has been shown that a complete pathway also exists in the plastids of rapeseeds (Kang & Rawsthorne, 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions, and the exact contribution of each reaction is still being debated (Ohlrogge & Browse, 1995, Plant Cell 7:957-970). It is accepted, however, that a large part of the acetyl-CoA is derived from glucose-6-phosphate and pyruvate that are imported from the cytoplasm into the plastids. Sucrose is produced in the source organs (leaves, or anywhere that photosynthesis occurs) and is transported to the developing seeds that are also termed sink organs. In the developing seeds, the sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (See, e.g., Töpfer et al. 1995, Science 268:681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al., 1995, Proc. Natl. Acad. Sci. USA 92:6743-6747). Tobacco plants have also been engineered to produce low levels of petroselinic acid by the introduction and expression of an acyl-ACP desaturase from coriander (Cahoon et al., 1992, Proc. Natl. Acad. Sci. USA 89:11184-11188).

The modification of seed oil content in plants has significant medical, nutritional, and economic ramifications. With regard to the medical ramifications, the long chain fatty acids (C18 and longer) found in many seed oils have been linked to reductions in hypercholesterolemia and other clinical disorders related to coronary heart disease (Brenner, 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^{6}$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as *Brassica*, soybean, carrot, pine, and *Arabidopsis thaliana* have also been cloned and determined to encode proteins associated with the phospholipid monolayer membrane of oil bodies in those plants.

It has also been determined that two phytohormones, gibberellic acid (GA) and absisic acid (ABA), are involved in overall regulatory processes in seed development (e.g. Ritchie & Gilroy, 1998, Plant Physiol. 116:765-776; Arenas-Huertero et al., 2000, Genes Dev. 14:2085-2096). Both the GA and ABA pathways are affected by okadaic acid, a protein phosphatase inhibitor (Kuo et al., 1996, Plant Cell. 8:259-269). The regulation of protein phosphorylation by kinases and phosphatases is accepted as a universal mechanism of cellular control (Cohen, 1992, Trends Biochem. Sci. 17:408-413). Likewise, the plant hormones ethylene (e.g. Zhou et al., 1998, Proc. Natl. Acad. Sci. USA 95:10294-10299; Beaudoin et al., 2000, Plant Cell 2000:1103-1115), and auxin (e.g. Colon-Carmona et al., 2000, Plant Physiol. 124:1728-1738) are involved in controlling plant development as well.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses a large number of nucleic acid sequences from *Arabidopsis thaliana, Brassica napus*, and the moss *Physcomitrella patens*. These nucleic acid sequences can be used to alter or increase the levels of seed storage compounds such as proteins, sugars and oils, in plants, including transgenic plants, such as rapeseed, canola, linseed, soybean, sunflower maize, oat, rye, barley, wheat, pepper, tagetes, cotton, oil palm, coconut palm, flax, castor and peanut, which are oilseed plants containing high amounts of lipid compounds.

SUMMARY OF THE INVENTION

The present invention provides novel isolated nucleic acid and amino acid sequences associated with the metabolism of seed storage compounds in plants.

The present invention also provides an isolated nucleic acid from *Arabidopsis, Brassica*, and *Physcomitrella patens* encoding a Lipid Metabolism Protein (LMP), or a portion thereof. These sequences may be used to modify or increase lipids and fatty acids, cofactors and enzymes in microorganisms and plants.

*Arabidopsis* plants are known to produce considerable amounts of fatty acids such as linoleic and linolenic acid (See, e.g., Table 2) and for their close similarity in many aspects (gene homology, etc.) to the oil crop plant *Brassica*. Therefore, nucleic acid molecules originating from a plant like *Arabidopsis thaliana* and *Brassica napus* are especially suited to modify the lipid and fatty acid metabolism in a host, especially in microorganisms and plants. Furthermore, nucleic acids from the plants *Arabidopsis thaliana* and *Brassica napus* can be used to identify those DNA sequences and enzymes in other species which are useful to modify the biosynthesis of precursor molecules of fatty acids in the respective organisms.

The present invention further provides an isolated nucleic acid comprising a fragment of at least 15 nucleotides of a nucleic acid from a plant (*Arabidopsis thaliana, Brassica napus*, or *Physcomitrella patens*) encoding a Lipid Metabolism Protein (LMP), or a portion thereof.

Also provided by the present invention are polypeptides encoded by the nucleic acids, heterologous polypeptides comprising polypeptides encoded by the nucleic acids, and antibodies to those polypeptides.

Additionally, the present invention relates to and provides the use of LMP nucleic acids in the production of transgenic plants having a modified level of a seed storage compound. A method of producing a transgenic plant with a modified level of a seed storage compound includes the steps of transforming a plant cell with an expression vector comprising a LMP nucleic acid, and generating a plant with a modified level of the seed storage compound from the plant cell. In a preferred embodiment, the plant is an oil producing species selected from the group consisting of rapeseed, canola, linseed, soybean, sunflower, maize, oat, rye, barley, wheat, pepper, tagetes, cotton, oil palm, coconut palm, flax, castor, and peanut, for example.

According to the present invention, the compositions and methods described herein can be used to increase or decrease the level of an LMP in a transgenic plant comprising increasing or decreasing the expression of the LMP nucleic acid in the plant. Increased or decreased expression of the LMP nucleic acid can be achieved through in vivo mutagenesis of the LMP nucleic acid. The present invention can also be used to increase or decrease the level of a lipid in a seed oil, to increase or decrease the level of a fatty acid in a seed oil, or to increase or decrease the level of a starch in a seed or plant.

Also included herein is a seed produced by a transgenic plant transformed by a LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, or to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing a LMP nucleic acid from *Arabidopsis thaliana, Brassica napus*, and *Physcomitrella patens* in the transgenic plant, wherein the transgenic plant is *Arabidopsis thaliana* and *Brassica napus*, or a species different from *Arabidopsis thaliana* and *Brassica napus*. Also included herein are compositions and methods of the modification of the efficiency of production of a seed storage compound. As used herein, the phrase "*Arabidopsis thaliana* and *Brassica napus*" means *Arabidopsis thaliana* and/or *Brassica napus.*

Accordingly, the present invention provides novel isolated LMP nucleic acids and isolated LMP amino acid sequences from *Arabidopsis thaliana, Brassica napus*, and *Physcomitrella patens*, as well as active fragments, analogs and orthologs thereof.

The present invention also provides transgenic plants having modified levels of seed storage compounds, and in particular, modified levels of a lipid, a fatty acid, or a sugar.

The polynucleotides and polypeptides of the present invention, including agonists and/or fragments thereof, also have uses that include modulating plant growth, and potentially plant yield, preferably increasing plant growth under adverse conditions (drought, cold, light, UV). In addition, antagonists of the present invention may have uses that include modulating plant growth and/or yield, preferably through increasing plant growth and yield. In yet another embodiment, overexpression of the polypeptides of the present invention using a constitutive promoter (e.g., 35S or other promoters) may be useful for increasing plant yield under stress conditions (drought, light, cold, UV) by modulating light utilization efficiency.

The present invention also provides methods for producing such aforementioned transgenic plants. In another embodiment, the present invention provides seeds and seed oils from such aforementioned transgenic plants.

These and other embodiments, features, and advantages of the present invention will become apparent after a review of the following detailed description of the disclosed embodiments and the appended claims.

DETAILED DESCRIPTION OF THE INVENTION

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

In accordance with the purpose(s) of this invention, as embodied and broadly described herein, this invention, in one aspect, provides an isolated nucleic acid from a plant (*Arabidopsis thaliana, Brassica napus*, and *Physcomitrella patens*) encoding a Lipid Metabolism Protein (LMP), or a portion thereof. As used herein, the phrase "*Arabidopsis thaliana, Brassica napus*, and *Physcomitrella patens*" means *Arabidopsis thaliana* and/or *Brassica napus* and/or *Physcomitrella patens.*

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the terms "nucleic acid molecule" and "polynucleotide sequence" are used interchangeably and are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences which naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., an *Arabidopsis thaliana* or *Brassica napus* cell). Moreover, an "isolated" nucleic acid molecule, such as a cDNA molecule, can be substantially free of other cellular material, or culture medium when produced by recombinant techniques, or chemical precursors, or other chemicals when chemically synthesized.

A nucleic acid molecule of the present invention, e.g., a nucleic acid molecule having a polynucleotide sequence of Appendix A (i.e. the polynucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81, or a portion thereof, can be isolated using standard molecular biology techniques and the sequence information provided herein. For example, an *Arabidopsis thaliana, Brassica napus*, or *Physcomitrella patens* LMP cDNA can be isolated from an *Arabidopsis thaliana, Brassica napus*, or *Physcomitrella patens* library using all or portion of one of the polynucleotide sequences of Appendix A as a hybridization probe and standard hybridization techniques (e.g., as described in Sambrook et al., 1989, Molecular Cloning: A Laboratory Manual. 2nd, ed., Cold Spring Harbor Laboratory, Cold Spring Harbor Laboratory Press, Cold Spring Harbor, N.Y.). Moreover, a nucleic acid molecule encompassing all or a portion of one of the polynucleotide sequences of Appendix A can be isolated by the polymerase chain reaction using oligonucleotide primers designed based upon this sequence (e.g., a nucleic acid molecule encompassing all or a portion of one of the sequences of Appendix A can be isolated by the polymerase chain reaction using oligonucleotide primers designed based upon this same sequence of Appendix A). For example, mRNA can be isolated from plant cells (e.g., by the guanidinium-thiocyanate extraction procedure of Chirgwin et al., 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the polynucleotide sequences shown in Appendix A. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a LMP nucleotide sequence can be prepared by standard synthetic techniques, e.g., using an automated DNA synthesizer.

In a preferred embodiment, an isolated nucleic acid of the invention comprises one of the polynucleotide sequences shown in Appendix A (i.e. SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81). These polynucleotides of Appendix A correspond to the *Arabidopsis thaliana, Brassica napus*, and *Physcomitrella patens* LMP cDNAs of the invention. These cDNAs comprise sequences encoding LMPs (i.e., the "coding region" or open reading frame (ORF)), as well as 5' untranslated sequences and 3' untranslated sequences. Alternatively, the nucleic acid molecules can comprise only the coding region of any of the polynucleotide sequences described herein or can contain whole genomic fragments isolated from genomic DNA.

For the purposes of this application, it will be understood that each of the polynucleotide sequences set forth in Appendix A has an identifying entry number (e.g., Pk123). Each of these sequences may generally comprise three parts: a 5' upstream region, a coding region, and a downstream region. The particular polynucleotide sequences shown in Appendix A represent the coding region or open reading frame, and the putative functions of the encoded polypeptides are indicated in Table 3.

TABLE 3

Putative LMP Functions

| Sequence code | Function | SEQ ID NO: |
|---|---|---|
| Pk123 | Gibberellin-regulated protein GASA3 precursor | 1 |
| Pk197 | Tyrosine aminotransferase | 3 |
| Pk136 | D-hydroxy-fatty acid dehydrogenase | 5 |
| Pk156 | Serine protease | 7 |
| Pk159 | Nonspecific lipid-transfer protein | 9 |
| Pk179 | Signal transduction protein | 11 |
| Pk202 | Lipid transfer-like protein | 13 |
| Pk206 | bZIP transcription factor | 15 |
| Pk207 | Acyl-CoA dehydrogenase | 17 |
| Pk209 | Pyruvate kinase | 19 |
| Pk215 | Phosphatidylglycerotransferase | 21 |
| Pk239 | Digalactosyldiacylglycerol synthase | 23 |
| Pk240 | Phosphatidate cytidyltransferase | 25 |
| Pk241 | AT Psbs protein | 27 |
| Pk242 | Omega-6 fatty acid desaturase, endoplasmic reticulum (FAD2) | 29 |
| Bn011 | Gibberellin 3-beta hydroxylase with +4 G | 31 |
| Bn077 | Zinc finger DNA binding protein | 33 |
| Jb001 | Gibberellin 20-oxidase | 35 |
| Jb002 | Seed maturation protein | 37 |
| Jb003 | Beta-VPE Vacuolar Processing Enzym | 39 |
| Jb005 | Very-long-chain fatty acid condensing enzyme CUT1 | 41 |
| Jb007 | Glucokinase | 43 |
| Jb009 | Glutathione S-transferase TSI-1 | 45 |
| Jb013 | ABA-regulated gene | 47 |
| Jb017 | Cysteine proteinase | 51 |
| Jb024 | Pectinesterase-like protein | 53 |
| Jb027 | Signal transduction protein | 55 |
| OO-1 | Aldose reductase-like protein | 57 |
| OO-2 | Dormancy related protein | 59 |
| OO-3 | HSP associated protein like | 61 |
| OO-4 | Poly (ADP-ribose) polymerase | 63 |
| OO-5 | Transitional endoplasmic reticulum ATPase | 65 |
| OO-6 | Beta coat like protein | 67 |
| OO-8 | Protein disulfide-isomerase | 69 |
| OO-9 | Signal transduction protein/Apoptosis inhibitor | 71 |

TABLE 3-continued

| Putative LMP Functions | | |
|---|---|---|
| Sequence code | Function | SEQ ID NO: |
| OO-10 | Annexin | 73 |
| OO-11 | Putative oxidoreductase | 75 |
| OO-12 | Long chain alc dehydrogenase/oxidoreductase | 77 |
| pp82 | Transcription factor | 79 |
| Pk225 | Amino-cyclopropane-carboxylic acid oxidase | 81 |

TABLE 4

| Grouping of LMPs based on Functional protein domains | | | | |
|---|---|---|---|---|
| Functional category | SEQ ID: | SEQ Code: | Functional domain | Domain position |
| DNA-binding proteins | 1 | Pk123 | Zinc finger | 66-86 |
| | | | | 29-71 |
| | 15 | Pk206 | bZIP transcription factor (PFAM) | 144-197 |
| | | | Leucine zipper | 179-209 |
| | 27 | Pk241 | DNA-binding domain | 207-221 |
| | | | Histone H5 signature | 57-71 |
| | 33 | Bn077 | Zinc finger (BRCT; PARP) | 64-104 |
| | | | Ethylene responsive element binding protein | 79-99 |
| | 63 | OO-4 | Zinc finger | 760-805 |
| | | | Leucine zipper | 114-117 |
| | 73 | OO-10 | Zinc finger | 220-230 |
| | | | Yeast DNA-binding domain | 207-217 |
| | 79 | pp82 | Myb DNA-binding domain | 19-119 |
| Kinases | 43 | Jb007 | Glucokinase | 173-206 |
| | 45 | Jb009 | Deoxynucleoside kinase | 99-139 |
| | 19 | Pk209 | Pyruvate kinase (PFAM) | 1-326 |
| | 61 | OO-3 | Galactokinase | 285-296 |
| Signal Transduction | 67 | OO-6 | Wnt-1 domain | 607-655 |
| | | | WSC domain | 527-548 |
| | 71 | OO-9 | BIR repeat (inhibitor of apoptosis) | 47-85 |
| | | | Wnt-1 domain | 43-91 |
| | 41 | Jb005 | Wnt-1 domain | 23-71 |
| | 47 | Jb013 | Wnt-1 domain | 23-91 |
| | 55 | Jb027 | Emp24/gp25L intracellular vesicle trafficking | 2-204 |
| | | | Wnt-1 domain | 135-183 |
| | 11 | Pk179 | Wnt-1 domain | 279-327 |
| | | | PDZ domain (Wnt signalling) | 205-299 |
| | 3 | Pk197 | Wnt-1 domain | 300-348 |
| Proteases | 7 | Pk156 | Serine protease | 171-191 |
| | | | Prolyl aminopeptidase | 128-139 |
| | 37 | Jb002 | Peptidase family M23/M37 | 404-444 |
| | 39 | Jb003 | Cysteine protease | 52-76 |
| | | | Peptidase C13 (PFAM) | 10-367 |
| | 51 | Jb017 | Cysteine protease C1 | 163-178 |
| | | | Peptidase C1 (PFAM) | 145-361 |
| | 65 | OO-5 | Peptidase family M41 | 343-387 |
| | | | | 620-664 |
| | | | AAA ATPase molecular chaperone (PFAM) | 243-427 |
| Lipid metabolism | 5 | Pk136 | D-Hydroxy-fatty acid dehydrogenase | 94-143 |
| | 9 | Pk159 | Lipid Transfer Protein LTP (PFAM) | 29-117 |
| | 13 | Pk202 | Lipid Transfer Protein LTP (PFAM) | 38-103 |
| | 17 | Pk207 | Acyl-CoA dehydrogenase | 2-44 |
| | | | Iron-containing alcohol dehydrogenase | 97-112 |
| | 21 | Pk215 | CDP-alcohol phosphatidyltransferase (PFAM) | 172-309 |
| | 23 | Pk239 | Glycosyl (galactosyl) transferase (PFAM) | 572-674 |
| | 25 | Pk240 | Phosphatidate cytidyltransferase | 343-370 |
| | 29 | Pk242 | Fatty acid desaturase (PFAM) | 32-376 |
| Oxido-reductases | 31 | Bn011 | Iron Ascorbate oxidoreductase (PFAM) | 43-343 |
| | 35 | Jb001 | Respiratory chain NADH dehydrogenase | 95-123 |
| | | | Iron Ascorbate oxidoreductase (PFAM) | 54-369 |
| | 53 | Jb024 | Multicopper oxidase | 216-247 |
| | | | | 123-145 |
| | | | Copper-oxidase (PFAM) | 154-306 |
| | 57 | OO-1 | Aldo/keto reductase family (PFAM) | 18-294 |
| | 59 | OO-2 | Alcohol dehydrogenase (PFAM) | 38-228 |
| | 69 | OO-8 | Thioredoxin (PFAM) | 22-250 |
| | 75 | OO-11 | Alcohol dehydrogenase (PFAM) | 50-234 |
| | 77 | OO-12 | Zinc alcohol dehydrogenase(PFAM) | 20-329 |
| | 81 | Pk225 | Iron Ascorbate oxidoreductase (PFAM) | 3-297 |

In another preferred embodiment, an isolated nucleic acid molecule of the present invention encodes a polypeptide that is able to participate in the metabolism of seed storage compounds such as lipids, starch, and seed storage proteins, and that contains a DNA-binding (or transcription factor) domain, a protein kinase domain, a signal transduction domain, a protease domain, a lipid metabolism domain, or an oxidoreductase domain. Examples of isolated nucleic acids that encode LMPs containing such domains can be found in Table 4. Examples of nucleic acids encoding LMPs containing a DNA-binding domain include those shown in SEQ ID NO:1, SEQ ID NO:15, SEQ ID NO:27, SEQ ID NO:33, SEQ ID NO:63, SEQ ID NO:73, and SEQ ID NO:79. Examples of nucleic acids encoding LMPs containing a protein kinase domain include those shown in SEQ ID NO:19, SEQ ID NO:43, SEQ ID NO:45, and SEQ ID NO:61. Examples of nucleic acids encoding LMPs containing a signal transduction domain include those shown in SEQ ID NO:3, SEQ ID NO:11, SEQ ID NO:41, SEQ ID NO:47, SEQ ID NO:55, SEQ ID NO:67, and SEQ ID NO:71. Examples of nucleic acids encoding LMPs containing a protease domain include those shown in SEQ ID NO:7, SEQ ID NO:37, SEQ ID NO:39, SEQ ID NO:51, and SEQ ID NO:65. Examples of nucleic acids encoding LMPs containing a lipid metabolism domain include those shown in SEQ ID NO:5, SEQ ID NO:9, SEQ ID NO:13, SEQ ID NO:17, SEQ ID NO:21, SEQ ID NO:23, SEQ ID NO:25, and SEQ ID NO:29. Examples of nucleic acids encoding LMPs containing a oxidoreductase domain include those shown in SEQ ID NO:31, SEQ ID NO:35, SEQ ID NO:53, SEQ ID NO:57, SEQ ID NO:59, SEQ ID NO:69, SEQ ID NO:75, SEQ ID NO:77, and SEQ ID NO:81.

In another preferred embodiment, an isolated nucleic acid molecule of the invention comprises a nucleic acid molecule, which is a complement of one of the polynucleotide sequences shown in Appendix A (i.e. SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81), or a portion thereof. A nucleic acid molecule which is complementary to one of the polynucleotide sequences shown in Appendix A is one which is sufficiently complementary to one of the polynucleotide sequences shown in Appendix A such that it can hybridize to one of the nucleotide sequences shown in Appendix A, thereby forming a stable duplex.

In another preferred embodiment, an isolated nucleic acid of the invention comprises a polynucleotide sequence encoding a polypeptide selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, or SEQ ID NO:82.

In still another preferred embodiment, an isolated nucleic acid molecule of the invention comprises a polynucleotide sequence which is at least about 50-60%, preferably at least about 60-70%, more preferably at least about 70-80%, 80-90%, or 90-95%, and even more preferably at least about 95%, 96%, 97%, 98%, 99%, or more homologous to a polynucleotide sequence shown in Appendix A, or a portion thereof. In an additional preferred embodiment, an isolated nucleic acid molecule of the invention comprises a polynucleotide sequence which hybridizes, e.g., hybridizes under stringent conditions, to one of the polynucleotide sequences shown in Appendix A, or a portion thereof. These stringent conditions include washing with a solution having a salt concentration of about 0.02 M at pH 7 and about 60° C. In another embodiment, the stringent conditions comprise an initial hybridization in a 6× sodium chloride/sodium citrate (6×SSC) solution at 65° C.

Moreover, the nucleic acid molecule of the invention can comprise only a portion of the coding region of one of the sequences in Appendix A, for example a fragment which can be used as a probe or primer or a fragment encoding a biologically active portion of a LMP. The polynucleotide sequences determined from the cloning of the LMP genes from *Arabidopsis thaliana, Brassica napus*, and *Physcomitrella patens* allows for the generation of probes and primers designed for use in identifying and/or cloning LMP homologues in other cell types and organisms, as well as LMP homologues from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in Appendix A, an anti-sense sequence of one of the sequences set forth in Appendix A, or naturally occurring mutants thereof. Primers based on a polynucleotide sequence of Appendix A can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a LMP, such as by measuring a level of a LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid encoded by a sequence of Appendix A such that the protein or portion thereof maintains the same or a similar function as the wild-type protein. As used herein, the language "sufficiently homologous" refers to proteins or portions thereof which have amino acid sequences which include a minimum number of identical or equivalent amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. As used herein, an "equivalent" amino acid residue is, for example, an amino acid residue which has a similar side chain as a particular amino acid residue that is encoded by a polynucleotide sequence of Appendix A. Regulatory proteins, such as DNA binding proteins, transcription factors, kinases, phosphatases, or protein members of metabolic pathways such as the lipid, starch and protein biosynthetic pathways, or membrane transport systems, may play a role in the biosynthesis of seed storage compounds. Examples of such activities are described herein (see putative annotations in Table 3). Examples of LMP-encoding nucleic acid sequences are set forth in Appendix A.

As altered or increased sugar and/or fatty acid production is a general trait wished to be inherited into a wide variety of plants like maize, wheat, rye, oat, triticale, rice, barley, soybean, peanut, cotton, rapeseed, canola, *manihot*, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for genetic engineering as one further embodiment of the present invention. As used herein, a "forage crop" includes, but is not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

Portions of proteins encoded by the LMP nucleic acid molecules of the invention are preferably biologically active portions of one of the LMPs. As used herein, the term "biologically active portion of a LMP" is intended to include a portion, e.g., a domain/motif, of a LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether a LMP or a biologically active portion thereof can participate in the metabolism of compounds necessary for the production of seed storage compounds and cellular membranes, an assay of enzymatic activity may be performed. Such assay methods are well known to those skilled in the art, and as described in Example 14 of the Exemplification.

Biologically active portions of a LMP include peptides comprising amino acid sequences derived from the amino acid sequence of a LMP (e.g., an amino acid sequence encoded by a nucleic acid sequence of Appendix A (i.e. SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81) or the amino acid sequence of a protein homologous to an LMP, which include fewer amino acids than a full length LMP or the full length protein which is homologous to an LMP) and exhibit at least one activity of an LMP. Typically, biologically active portions (peptides, e.g., peptides which are, for example, 5, 10, 15, 20, 30, 35, 36, 37, 38, 39, 40, 50, 100, or more amino acids in length) comprise a domain or motif with at least one activity of a LMP. Moreover, other biologically active portions, in which other regions of the protein are deleted, can be prepared by recombinant techniques and evaluated for one or more of the activities described herein. Preferably, the biologically active portions of a LMP include one or more selected domains/motifs or portions thereof having biological activity.

Additional nucleic acid fragments encoding biologically active portions of a LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the polynucleotide sequences shown in Appendix A (i.e. SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81), and portions thereof) due to degeneracy of the genetic code and thus encode the same LMP as that encoded by the polynucleotide sequences shown in Appendix A. In a further embodiment, the nucleic acid molecule of the invention encodes a full length protein which is substantially homologous to an amino acid sequence shown in Appendix A. In one embodiment, the full-length nucleic acid or protein or fragment of the nucleic acid or protein is from *Arabidopsis thaliana, Brassica napus*, and *Physcomitrella patens.*

In addition to the *Arabidopsis thaliana, Brassica napus*, and *Physcomitrella patens* LMP polynucleotide sequences described herein, it will be appreciated by those skilled in the art that DNA sequence polymorphisms that lead to changes in the amino acid sequences of LMPs may exist within a population (e.g., the *Arabidopsis thaliana*, and *Brassica napus*, and *Physcomitrella patens* population). Such genetic polymorphism in the LMP gene may exist among individuals within a population due to natural variation. As used herein, the terms "gene" and "recombinant gene" refer to nucleic acid molecules comprising an open reading frame encoding a LMP, preferably an *Arabidopsis thaliana, Brassica napus*, or *Physcomitrella patens* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana* and *Brassica napus* orthologs of the *Arabidopsis thaliana, Brassica napus*, and *Physcomitrella patens* LMP cDNA of the invention can be isolated based on their homology to *Arabidopsis thaliana, Brassica napus*, and *Physcomitrella patens* LMP nucleic acid disclosed herein using the *Arabidopsis thaliana, Brassica napus*, and *Physcomitrella patens* cDNA, or a portion thereof, as a hybridization probe according to standard hybridization techniques under stringent hybridization conditions. As used herein, the term "orthologs" refers to two nucleic acids from different species, but that have evolved from a common ancestral gene by specification. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising a polynucleotide sequence shown in Appendix A. In other embodiments, the nucleic acid is at least 30, 50, 100, 250, or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75%, or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65C. In another embodiment, the stringent conditions comprise an initial hybridization in a 6× sodium chloride/sodium citrate (6×SSC) solution at 65° C. Preferably, an isolated nucleic acid molecule of the invention that hybridizes under stringent conditions to a polynucleotide sequence of Appendix A (i.e. SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81) corresponds to a naturally occurring nucleic acid molecule. As used herein, a "naturally-occurring" nucleic acid molecule refers to an RNA or DNA molecule having a polynucleotide sequence that occurs in nature (e.g., encodes a natural protein). In one embodiment, the nucleic acid encodes a natural *Arabidopsis thaliana, Brassica napus*, or *Physcomitrella patens* LMP.

In addition to naturally-occurring variants of the LMP sequence that may exist in the population, the skilled artisan will further appreciate that changes can be introduced by mutation into a polynucleotide sequence of Appendix A, thereby leading to changes in the amino acid sequence of the encoded LMP, without altering the functional ability of the LMP. For example, nucleotide substitutions leading to amino acid substitutions at "non-essential" amino acid residues can be made in a polynucleotide sequence of Appendix A. A "non-essential" amino acid residue is a residue that can be altered from the wild-type sequence of one of the LMPs (Appendix A) without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment, the isolated nucleic acid molecule comprises a nucleotide sequence encoding a protein, wherein the protein comprises an amino acid sequence at least about 50% homologous to an amino acid sequence encoded by a nucleic acid of Appendix A and is capable of participation in the metabolism of compounds necessary for the production of seed storage compounds in *Arabidopsis thaliana, Brassica napus*, and *Physcomitrella patens*, or cellular membranes, or has one or more activities set forth in Table 3. Preferably, the protein encoded by the nucleic acid molecule is at least about 50-60% homologous to one of the sequences encoded by a nucleic acid of Appendix A (i.e. SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81), more preferably at least about 60-70% homologous to one of the sequences encoded by a nucleic acid of Appendix A, even more preferably at least about 70-80%, 80-90%, or 90-95% homologous to one of the sequences encoded by a nucleic acid of Appendix A, and most preferably at least about 96%, 97%, 98%, or 99% homologous to one of the sequences encoded by a nucleic acid of Appendix A.

To determine the percent homology of two amino acid sequences (e.g., one of the sequences encoded by a nucleic acid of Appendix A and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences encoded by a nucleic acid of Appendix A) is occupied by the same amino acid residue or nucleotide as the corresponding position in the other sequence (e.g., a mutant form of the sequence encoded by a nucleic acid of Appendix A), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding a LMP homologous to a protein sequence encoded by a nucleic acid of Appendix A can be created by introducing one or more nucleotide substitutions, additions, or deletions into a polynucleotide sequence of Appendix A such that one or more amino acid substitutions, additions, or deletions are introduced into the encoded protein. Mutations can be introduced into one of the sequences of Appendix A by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a LMP is preferably replaced with another amino acid residue from the same side chain family. Alternatively, in another embodiment, mutations can be introduced randomly along all or part of a LMP coding sequence, such as by saturation mutagenesis, and the resultant mutants can be screened for a LMP activity described herein to identify mutants that retain LMP activity. Following mutagenesis of one of the sequences of Appendix A, the encoded protein can be expressed recombinantly and the activity of the protein can be determined using, for example, assays described herein (see Examples 13-14 of the Exemplification).

LMPs are preferably produced by recombinant DNA techniques. For example, a nucleic acid molecule encoding the protein is cloned into an expression vector (as described above), the expression vector is introduced into a host cell (as described herein), and the LMP is expressed in the host cell. The LMP can then be isolated from the cells by an appropriate purification scheme using standard protein purification techniques. Alternative to recombinant expression, a LMP or peptide thereof can be synthesized chemically using standard peptide synthesis techniques. Moreover, native LMP can be isolated from cells, for example using an anti-LMP antibody, which can be produced by standard techniques utilizing a LMP or fragment thereof of this invention.

The invention also provides LMP chimeric or fusion proteins. As used herein, a LMP "chimeric protein" or "fusion protein" comprises a LMP polypeptide operatively linked to a non-LMP polypeptide. An "LMP polypeptide" refers to a polypeptide having an amino acid sequence corresponding to a LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. As used herein with respect to the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is a LMP containing a heterologous signal sequence at its N-terminus. In certain host cells (e.g., mammalian host cells), expression and/or secretion of a LMP can be increased through use of a heterologous signal sequence.

Preferably, a LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (See, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding a LMP. The term "coding region" refers to the region of the nucleotide sequence comprising codons which are translated into amino acid residues (e.g., the entire coding region of Pk121 comprises nucleotides 1 to 786). In another embodiment, the antisense nucleic acid molecule is antisense to a "noncoding region" of the coding strand of a nucleotide sequence encoding LMP. The term "noncoding region" refers to 5' and 3' sequences which flank the coding region that are not translated into amino acids (i.e., also referred to as 5' and 3' untranslated regions).

Given the coding strand sequences encoding LMP disclosed herein (e.g., the polynucleotide sequences set forth in Appendix A), antisense nucleic acids of the invention can be designed according to the rules of Watson and Crick base pairing. The antisense nucleic acid molecule can be complementary to the entire coding region of LMP mRNA, but more preferably is an oligonucleotide which is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45, or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydro-uracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methyl-cytosine, N-6-adenine, 7-methylguanine, 5-methylaminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct.

The antisense nucleic acid molecules of the invention are typically administered to a cell or generated in situ such that they hybridize with or bind to cellular mRNA and/or genomic DNA encoding a LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an anomeric nucleic acid molecule. An anomeric nucleic acid molecule forms specific double-stranded hybrids with complementary RNA in which, contrary to the usual units, the strands run parallel to each other (Gaultier et al., 1987, Nucleic Acids Res. 15:6625-6641). The antisense nucleic acid molecule can also comprise a 2'-o-methyl-ribonucleotide (Inoue et al., 1987, Nucleic Acids Res. 15:6131-6148) or a chimeric RNA-DNA analogue (Inoue et al., 1987, FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff & Gerlach, 1988, Nature 334:585-591)) can be used to catalytically cleave LMP mRNA transcripts to thereby inhibit translation of LMP mRNA. A ribozyme having specificity for an LMP-encoding nucleic acid can be designed based upon the nucleotide sequence of an LMP cDNA disclosed herein (e.g., Pk123 in Appendix A) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a LMP-encoding mRNA (See, e.g., U.S. Pat. Nos. 4,987,071 and 5,116,742 to Cech et al.). Alternatively, LMP mRNA can be used to select a catalytic RNA having a specific ribonuclease activity from a pool of RNA molecules (See, e.g., Bartel, D. & Szostak J. W. 1993, Science 261:1411-1418).

Alternatively, LMP gene expression can be inhibited by targeting nucleotide sequences complementary to the regulatory region of a LMP nucleotide sequence (e.g., a LMP promoter and/or enhancers) to form triple helical structures that prevent transcription of a LMP gene in target cells (See generally, Helene C., 1991, Anticancer Drug Des. 6:569-84; Helene C. et al., 1992, Ann. N.Y. Acad. Sci. 660:27-36; and Maher, L. J., 1992, Bioassays 14:807-15).

Another aspect of the invention pertains to vectors, preferably expression vectors, containing a nucleic acid encoding a LMP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990) and Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovirus expression vectors), yeast and other fungal cells (See Romanos M. A. et al., 1992, Foreign gene expression in yeast: a review, Yeast 8:423-488; van den Hondel, C. A. M. J. J. et al., 1991, Heterologous gene expression in filamentous fungi, in: More Gene Manipulations in Fungi, Bennet & Lasure, eds., p. 396-428: Academic Press: an Diego; and van den Hondel & Punt, 1991, Gene transfer systems and vector development for filamentous fungi, in: Applied Molecular Genetics of Fungi, Peberdy et al., eds., p. 1-28, Cambridge University Press: Cambridge), algae (Falciatore et al., 1999, Marine Biotechnology 1:239-251), ciliates of the types: Holotrichia, Peritrichia, Spirotrichia, Suctoria, Tetrahymena, *Paramecium, Colpidium*, Glaucoma, *Platyophrya*, Potomacus, *Pseudocohnilembus, Euplotes, Engelmaniella*, and *Stylonychia*, especially of the genus *Stylonychia lemnae* with vectors following a transformation method as described in WO 98/01572, and multicellular plant cells (See Schmidt & Willmitzer, 1988, High efficiency *Agrobacterium tumefaciens*-mediated transformation of *Arabidopsis thaliana* leaf and cotyledon plants, Plant Cell Rep.:583-586; Plant Molecular Biology and Biotechnology, C Press, Boca Raton, Fla., chapter 6/7, S. 71-119 (1993); White, Jenes et al., Techniques for Gene Transfer, in: Transgenic Plants, Vol. 1, Engineering and Utilization, eds.: Kung and Wu, Academic Press 1993, 128-43; Potrykus, 1991, Annu. Rev. Plant Physiol. Plant Mol. Biol. 42:205-225 (and references cited therein)), or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith & Johnson, 1988, Gene 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al., 1988, Gene 69:301-315) and pET 11d (Studier et al., 1990, Gene Expression Technology: Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S., 1990, Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al., 1992, Nucleic Acids Res. 20:2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al., 1987, Embo J. 6:229-234), pMFa (Kurjan & Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt, 1991, "Gene transfer systems and vector development for filamentous fungi, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al., 1983, Mol. Cell. Biol. 3:2156-2165) and the pVL series (Lucklow & Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, Fritsh and Maniatis, Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the LMPs of the invention may be expressed in uni-cellular plant cells (such as algae, see Falciatore et al. (1999, Marine Biotechnology 1:239-251 and references therein) and plant cells from higher plants (e.g., the spermatophytes, such as crop plants). Examples of plant expression vectors include those detailed in: Becker, Kemper, Schell and Masterson (1992, "New plant binary vectors with selectable markers located proximal to the left border", Plant Mol. Biol. 20:1195-1197) and Bevan (1984, "Binary *Agrobacterium* vectors for plant transformation, Nucleic Acids Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38).

A plant expression cassette preferably contains regulatory sequences capable to drive gene expression in plant cells and which are operatively linked so that each sequence can fulfil its function such as termination of transcription, including polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3:835) or functional equivalents thereof but also all other terminators functionally active in plants are suitable.

As plant gene expression is very often not limited on transcriptional levels a plant expression cassette preferably contains other operatively linked sequences like translational enhancers such as the overdrive-sequence containing the 5'-untranslated leader sequence from tobacco mosaic virus enhancing the protein per RNA ratio (Gallie et al. 1987, Nucleic Acids Res. 15:8693-8711).

Plant gene expression has to be operatively linked to an appropriate promoter conferring gene expression in a timely, cell or tissue specific manner. Preferred are promoters driving constitutive expression (Benfey et al. 1989, EMBO J. 8:2195-2202) like those derived from plant viruses like the 35S CAMV (Franck et al. 1980, Cell 21:285-294), the 19S CaMV (see also U.S. Pat. No. 5,352,605 and WO 84/02913) or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al. 1991, Mol. Gen. Genetics 225:459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO91/3980) or the legumin B4 promoter (LeB4; Baeumlein et al. 1992, Plant J. 2:233-239) as well as promoters conferring seed specific expression in monocot plants like maize, barley, wheat, rye, rice etc. Suitable promoters to note are the 1pt2 or 1pt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum kasirin*-gene, and the rye secalin gene).

Plant gene expression can also be facilitated via an inducible promoter (for review see Gatz 1997, Annu. Rev. Plant Physiol. Plant Mol. Biol. 48:89-108). Chemically inducible promoters are especially suitable if gene expression is desired in a time specific manner Examples for such promoters are a salicylic acid inducible promoter (WO 95/19443), a tetracycline inducible promoter (Gatz et al. 1992, Plant J. 2:397-404) and an ethanol inducible promoter (WO 93/21334).

Promoters responding to biotic or abiotic stress conditions are also suitable promoters such as the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (for review see Kermode 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Also especially suited are promoters that confer plastid-specific gene expression, as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a LMP can be expressed in bacterial cells, insect cells, fungal cells, mammalian cells (such as Chinese hamster ovary cells (CHO) or COS cells), algae, ciliates or plant cells.

Other suitable host cells are known to those skilled in the art.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989*, Molecular Cloning: A Laboratory Manual.* 2nd, ed., Cold Spring Harbor Laboratory, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycin and methotrexate or in plants that confer resistance towards an herbicide such as glyphosate or glufosinate. A nucleic acid encoding a selectable marker can be introduced into a host cell on the same vector as that encoding a LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of a LMP gene into which a deletion, addition or substitution has been introduced to thereby alter, e.g., functionally disrupt, the LMP gene. Preferably, this LMP gene is an *Arabidopsis thaliana, Brassica napus*, and *Physcomitrella patens* LMP gene, but it can be a homologue from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al. 1999, Nucleic Acids Res. 27:1323-1330 and Kmiec 1999, American Scientist 87:240-247). Homologous recombination procedures in *Arabidopsis thaliana* are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flanking LMP nucleic acid is of sufficient length for successful homologous recombination with the endogenous gene. Typically, several hundreds of base pairs up to kilobases of flanking DNA (both at the 5' and 3' ends) are included in the vector (see e.g., Thomas & Capecchi 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems which allow for regulated expression of the introduced gene. For example, inclusion of a LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) a LMP. Accordingly, the invention further provides methods for producing LMPs using the host cells of the invention. In one embodiment, the method comprises culturing a host cell of the invention (into which a recombinant expression vector encoding a LMP has been introduced, or which contains a wild-type or altered LMP gene in it's genome) in a suitable medium until LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals which are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana* and *Brassica napus* LMP in other plants than *Arabidopsis thaliana* and *Brassica napus* or microorganisms, algae or fungi.

An isolated LMP or a portion thereof of the invention can participate in the metabolism of compounds necessary for the production of seed storage compounds in *Arabidopsis thaliana* and *Brassica napus*, or of cellular membranes, or has one or more of the activities set forth in Table 3. In preferred embodiments, the protein or portion thereof comprises an amino acid sequence which is sufficiently homologous to an amino acid sequence encoded by a nucleic acid of Appendix A such that the protein or portion thereof maintains the ability to participate in the metabolism of compounds necessary for the construction of cellular membranes in *Arabidopsis thaliana* and *Brassica napus*, or in the transport of molecules across these membranes. The portion of the protein is preferably a biologically active portion as described herein. In another preferred embodiment, a LMP of the invention has an amino acid sequence encoded by a nucleic acid of Appendix A. In yet another preferred embodiment, the LMP has an amino acid sequence which is encoded by a nucleotide sequence which hybridizes, e.g., hybridizes under stringent conditions, to a nucleotide sequence of Appendix A. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99% or more homologous to one of the amino acid sequences encoded by a nucleic acid of Appendix A. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence of Appendix A, and which can participate in the metabolism of compounds necessary for the construction of cellular membranes in *Arabidopsis thaliana* and *Brassica napus*, or in the transport of molecules across these membranes, or which has one or more of the activities set forth in Table 3.

In other embodiments, the LMP is substantially homologous to an amino acid sequence encoded by a nucleic acid of Appendix A and retains the functional activity of the protein of one of the sequences encoded by a nucleic acid of Appendix A yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence and which has at least one of the LMP activities described herein. In another embodiment, the invention pertains to a full *Arabidopsis thaliana* and *Brassica napus* protein which is substantially homologous to an entire amino acid sequence encoded by a nucleic acid of Appendix A.

Dominant negative mutations or trans-dominant suppression can be used to reduce the activity of a LMP in transgenics seeds in order to change the levels of seed storage compounds. To achieve this a mutation that abolishes the activity of the LMP is created and the inactive non-functional LMP gene is overexpressed in the transgenic plant. The inactive trans-dominant LMP protein competes with the active endogenous LMP protein for substrate or interactions with other proteins and dilutes out the activity of the active LMP. In this way the biological activity of the LMP is reduced without actually modifying the expression of the endogenous LMP gene. This strategy was used by Pontier et al to modulate the activity of plant transcription factors (Pontier D, Miao Z H, Lam E, Plant J 2001 September; 27(6):529-38, Trans-dominant suppression of plant TGA factors reveals their negative and positive roles in plant defense responses).

Homologues of the LMP can be generated by mutagenesis, e.g., discrete point mutation or truncation of the LMP. As used herein, the term "homologue" refers to a variant form of the LMP which acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP, by, for example, competitively binding to a downstream or upstream member of the cell membrane component metabolic cascade which includes the LMP, or by binding to a LMP which mediates transport of compounds across such membranes, thereby preventing translocation from taking place.

In an alternative embodiment, homologues of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods which can be used to produce libraries of potential LMP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (see, e.g., Narang 1983, Tetrahedron 39:3; Itakura et al. 1984, Annu. Rev. Biochem. 53:323; Itakura et al. 1984, Science 198:1056; Ike et al. 1983, Nucleic Acids Res. 11:477).

In addition, libraries of fragments of the LMP coding sequences can be used to generate a variegated population of LMP fragments for screening and subsequent selection of homologues of a LMP. In one embodiment, a library of coding sequence fragments can be generated by treating a double stranded PCR fragment of a LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LMP homologues (Arkin & Yourvan 1992, Proc. Natl. Acad. Sci. USA 89:7811-7815; Delgrave et al. 1993, Protein Engineering 6:327-331).

In another embodiment, cell based assays can be exploited to analyze a variegated LMP library, using methods well known in the art.

The nucleic acid molecules, proteins, protein homologues, fusion proteins, primers, vectors, and host cells described herein can be used in one or more of the following methods: identification of *Arabidopsis thaliana* and *Brassica napus* and related organisms; mapping of genomes of organisms related to *Arabidopsis thaliana* and *Brassica napus*; identification and localization of *Arabidopsis thaliana* and *Brassica napus* sequences of interest; evolutionary studies; determination of LMP regions required for function; modulation of a LMP activity; modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as *Brassica napus* or soybean which require light to drive photosynthesis and growth. Plants like *Arabidopsis thaliana* and *Brassica napus* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, they may be used to identify an organism as being *Arabidopsis thaliana, Brassica napus*, and *Physcomitrella patens* or a close relative thereof. Also, they may be used to identify the presence of *Arabidopsis thaliana, Brassica napus*, and *Physcomitrella patens* or a relative thereof in a mixed population of microorganisms. The invention provides the nucleic acid sequences of a number of *Arabidopsis thaliana* and *Brassica napus* genes; by probing the extracted genomic DNA of a culture of a unique or mixed population of microorganisms under stringent conditions with a probe spanning a region of an *Arabidopsis thaliana* and *Brassica napus* gene which is unique to this organism, one can ascertain whether this organism is present.

Further, the nucleic acid and protein molecules of the invention may serve as markers for specific regions of the genome. This has utility not only in the mapping of the genome, but also for functional studies of *Arabidopsis thaliana* and *Brassica napus* proteins. For example, to identify the region of the genome to which a particular *Arabidopsis thaliana* and *Brassica napus* DNA-binding protein binds, the *Arabidopsis thaliana* and *Brassica napus* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana* and *Brassica napus*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of a LMP of the invention may directly affect the accumulation of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where over expression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al. 2000, Plant J. 24:383-396) and the lipid composition in leaves and roots (Härtel et al. 2000, Proc. Natl. Acad. Sci. USA 97:10649-10654). Likewise, the activity of the plant ACCase has been demonstrated to be regulated by phosphorylation (Savage & Ohlrogge 1999, Plant J. 18:521-527) and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/or membrane protein regulation occur in envelopes (see, e.g., Müller et al. 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al. 2001, Plant J. 25:295-303). For more examples see also the section 'background of the invention'.

The present invention also provides antibodies which specifically binds to an LMP-polypeptide, or a portion thereof, as encoded by a nucleic acid disclosed herein or as described herein.

Antibodies can be made by many well-known methods (see, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (see, for example, Kelly et al. 1992, Bio/Technology 10:163-167; Bebbington et al. 1992, Bio/Technology 10:169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics," Cold Spring Harbor Laboratory Press: ISBN 0-87969-451-3).

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg), and Sigma (Deisenhofen). Solutions were prepared using purified, pyrogen-free water, designated as $H_2O$ in the following text, from a Milli-Q water system water purification plant (Millipore, Eschborn). Restriction endonucleases, DNA-modifying enzymes, and molecular biology kits were obtained from the companies AGS (Heidelberg), Amersham (Braunschweig), Biometra (Göttingen), Boehringer (Mannheim), Genomed (Bad Oeynnhausen), New England Biolabs (Schwalbachl Taunus), Novagen (Madison, Wis., USA), Perkin-Elmer (Weiterstadt), Pharmacia (Freiburg), Qiagen (Hilden), and Stratagene (Amsterdam, Netherlands). They were used, if not mentioned otherwise, according to the manufacturer's instructions.

c) Plant Material:

*Arabidopsis* pkl mutant

For this study, in one series of experiments, root material of wild-type and pickle mutant *Arabidopsis thaliana* plants were used. The pkl mutation was isolated from an ethyl methanesulfonate-mutagenized population of the Columbia ecotype as described (Ogas et al., 1997, Science 277:91-94; Ogas et al., 1999, Proc. Natl. Acad. Sci. USA 96:13839-13844). In other series of experiments, siliques of individual ecotypes of *Arabidopsis thaliana* and of selected *Arabidopsis* phytohormone mutants were used. Seeds were obtained from the *Arabidopsis* stock center.

*Brassica napus* AC Excel and Cresor Varieties

*Brassica napus* varieties AC Excel and Cresor were used for this study to create cDNA libraries. Seed, seed pod, flower, leaf, stem, and root tissues were collected from plants that were in some cases dark-, salt-, heat-, and drought-treated. However, this study focused on the use of seed and seed pod tissues for cDNA libraries.

d) Plant Growth:

*Arabidopsis thaliana*

Plants were either grown on Murashige-Skoog medium as described in Ogas et al. (1997, Science 277:91-94; 1999, Proc. Natl. Acad. Sci. USA 96:13839-13844) or on soil under standard conditions as described in Focks & Benning (1998, Plant Physiol. 118:91-101).

*Brassica napus*

Plants (AC Excel, except where mentioned) were grown in Metromix (Scotts, Marysville, Ohio) at 22° C. under a 14/10 light/dark cycle. Six seed and seed pod tissues of interest in this study were collected to create the following cDNA libraries: Immature seeds, mature seeds, immature seed pods, mature seed pods, night-harvested seed pods, and Cresor variety (high erucic acid) seeds. Tissue samples were collected within specified time points for each developing tissue and multiple samples within a time frame pooled together for eventual extraction of total RNA. Samples from immature seeds were taken between 1-25 days after anthesis (daa), mature seeds between 25-50 daa, immature seed pods between 1-15 daa, mature seed pods between 15-50 daa, night-harvested seed pods between 1-50 daa and Cresor seeds 5-25 daa.

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g and RT for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of H2O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and poly-(A)+ RNA from Plants

*Arabidopsis thaliana*

For the investigation of transcripts, both total RNA and poly-(A)+ RNA were isolated. RNA was isolated from siliques of *Arabidopsis* plants according to the following procedure:

RNA preparation from *Arabidopsis* seeds—"hot" extraction:

Buffers, Enzymes, and Solutions:

2M KCl
Proteinase K
Phenol (for RNA)
Chloroform:Isoamylalcohol
(Phenol:choloroform 1:1; pH adjusted for RNA)
4 M LiCl, DEPC-treated
DEPC-treated water
3M NaOAc, pH 5, DEPC-treated
Isopropanol
70% ethanol (made up with DEPC-treated water)
Resuspension buffer: 0.5% SDS, 10 mM Tris pH 7.5, 1 mM EDTA made up with DEPC-treated water as this solution can not be DEPC-treated
Extraction Buffer:
0.2M Na Borate
30 mM EDTA
30 mM EGTA
1% SDS (250 μl of 10% SDS-solution for 2.5 ml buffer)
1% Deoxycholate (25 mg for 2.5 ml buffer)
2% PVPP (insoluble—50 mg for 2.5 ml buffer)
2% PVP 40K (50 mg for 2.5 ml buffer)
10 mM DTT 100 mM β-Mercaptoethanol (fresh, handle under fume hood—use 35 μl of 14.3M solution for 5 ml buffer)

Extraction

Extraction buffer was heated up to 80° C. Tissues were ground in liquid nitrogen-cooled mortar, and the tissue powder was transferred to a 1.5 ml tube. Tissues should be kept frozen until buffer is added; the sample should be transferred with a pre-cooled spatula; and the tube should be kept in liquid nitrogen at all times. Then 350 μl preheated extraction buffer was added (For 100 mg tissue, buffer volume can be as much as 500 μl for bigger samples) to tube; samples were vortexed; and the tube was heated to 80° C. for approximately 1 minute and then kept on ice. The samples were vortexed and ground additionally with electric mortar.

Digestion

Proteinase K (0.15 mg/100 mg tissue) was added, and the mixture was vortexed and then kept at 37° C. for one hour.

First Purification

For purification, 27 μl 2 M KCl was added to the samples. The samples were chilled on ice for 10 minutes and then centrifuged at 12.000 rpm for 10 minutes at room temperature. The supernatant was transferred to a fresh, RNAase-free tube, and one phenol extraction was conducted, followed by a choloroform:isoamylalcohol extraction. One volume isopropanol to was added to the supernatant, and the mixture was chilled on ice for 10 minutes. RNA was pelleted by centrifugation (7000 rpm for 10 minutes at room temperature). Pellets were dissolved in 1 ml 4M LiCl solution by vortexing the mixture 10 to 15 minutes. RNA was pelleted by a 5 minute centrifugation.

Second Purification

The pellet was resuspended in 500 μl Resuspension buffer. Then 500 μl of phenol was added, and the mixture was vortexed. Then, 250 μl chloroform:isoamylalcohol was added; the mixture was vortexed and then centrifuged for 5 minutes. The supernatant was transferred to a fresh tube. The choloform:isoamylalcohol extraction was repeated until the interface was clear. The supernatant was transferred to a fresh tube and 1/10 volume 3M NaOAc, pH 5 and 600 μl isopropanol were added. The mixture was kept at −20 for 20 minutes or longer. The RNA was pelleted by 10 minutes of centrifugation, and then the pellet was washed once with 70% ethanol. All remaining alcohol was removed before dissolving the pellet in 15 to 20 μl DEPC-treated water. The quantity and quality of the RNA was determined by measuring the absorbance of a 1:200 dilution at 260 nm and 280 nm (40 μg RNA/ml=1 $OD_{260}$)

RNA from roots of wild-type *Arabidopsis* and the pickle mutant of *Arabidopsis* was isolated as described (Ogas et al., 1997, Science 277:91-94; Ogas et al., 1999, Proc. Natl. Acad. Sci. USA 96:13839-13844).

The mRNA was prepared from total RNA, using the Amersham Pharmacia Biotech mRNA purification kit, which utilizes oligo(dT)-cellulose columns Isolation of Poly-(A)+ RNA was isolated using Dyna BeadsR (Dynal, Oslo, Norway) following the instructions of the manufacturer's protocol. After determination of the concentration of the RNA or of the poly(A)+ RNA, the RNA was precipitated by addition of 1/10 volume of 3 M sodium acetate pH 4.6 and 2 volumes of ethanol and stored at −70° C.

*Brassica napus*

Seeds were separated from pods to create homogeneous materials for seed and seed pod cDNA libraries. Tissues were ground into fine powder under liquid nitrogen using a mortar and pestle and transferred to a 50 ml tube. Tissue samples were stored at −80° C. until extractions could be performed. Total RNA was extracted from tissues using RNeasy Maxi kit (Qiagen) according to manufacturer's protocol, and mRNA was processed from total RNA using Oligotex mRNA Purification System kit (Qiagen), also according to manufacturer's protocol. The mRNA was sent to Hyseq Pharmaceuticals Incorporated (Sunnyville, Calif.) for further processing of mRNA from each tissue type into cDNA libraries and for use in their proprietary processes in which similar inserts in plasmids are clustered based on hybridization patterns.

Example 4 cDNA Library Construction

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

*Brassica* cDNA libraries were generated at Hyseq Pharmaceuticals Incorporated (Sunnyville, Calif.) No amplification steps were used in the library production to retain expression information. Hyseq's genomic approach involves grouping the genes into clusters and then sequencing representative members from each cluster. The cDNA libraries were generated from oligo dT column purified mRNA. Colonies from transformation of the cDNA library into *E. coli* were randomly picked and the cDNA insert were amplified by PCR and spotted on nylon membranes. A set of $^{33-}$P radiolabeled oligonucleotides were hybridized to the clones, and the resulting hybridization pattern determined to which cluster a particular clone belonged. The cDNA clones and their DNA sequences were obtained for use in overexpression in transgenic plants and in other molecular biology processes described herein.

Example 5

Identification of LMP Genes of Interest

*Arabidopsis thaliana* pkl Mutant

The pickle *Arabidopsis* mutant was used to identify LMP-encoding genes. The pickle mutant accumulates seed storage compounds, such as seed storage lipids and seed storage proteins, in the root tips (Ogas et al., 1997, Science 277:91-94; Ogas et al., 1999, Proc. Natl. Acad. Sci. USA 96:13839-13844). The mRNA isolated from roots of wild-type and pickle plants was used to create a subtracted and normalized cDNA library (SSH library) containing cDNAs that are only present in the pickle roots, but not in the wild-type roots. Clones from the SSH library were spotted onto nylon membranes and hybridized with radio-labeled pickle or wild-type root mRNA to ascertain that the SSH clones were more abundant in pickle roots compared to wild-type roots. These SSH clones were randomly sequenced and the sequences were annotated (See Example 9). Based on the expression levels and on these initial functional annotations (See Table 3), clones from the SSH library were identified as potential LMP-encoding genes.

To identify additional potential gene targets from the *Arabidopsis* pickle mutant, the Megasort™ and MPSS technologies of Lynx Therapeutics Inc. were used. MegaSort is a micro-bead technology that allows both the simultaneous collection of millions of clones on as many micro-beads (See Brenner et al., 1999, Proc. Natl. Acad. Sci. USA 97:1665-1670). Genes are identified based on their differential expression in wild-type and pickle *Arabidopsis* mutant roots. RNA and mRNA are isolated from wild-type and mutant roots using standard procedures. The MegaSort technology enables the identification of over- and under-expressed clones in two mRNA samples without prior knowledge of the genes and is thus useful to discover differentially expressed genes that can encode LMP proteins. The MPSS technology enables the quantitation of the abundance of mRNA transcripts in mRNA samples (Brenner et al., Nat. Biotechnol. 18:630-4) and was used to obtain expression profiles of wild-type and pickle root mRNAs.

Other LMP candidate genes were identified by randomly selecting various *Arabidopsis* phytohormone mutants (e.g. mutants obtained from EMS treatment) from the *Arabidopsis* stock center. These mutants and control wild-type plants were grown under standard conditions in growth chambers and screened for the accumulation of seed storage compounds. Mutants showing altered levels of seed storage compounds were considered as having a mutation in a LMP candidate gene and were investigated further.

*Brassica napus*

RNA expression profile data was obtained from the Hyseq clustering process. Clones showing 75% or greater expression in seed libraries compared to the other tissue libraries were selected as LMP candidate genes. The *Brassica napus* clones were selected for overexpression in *Arabidopsis* based on their expression profile.

Example 6

Cloning of Full-Length cDNAs and Orthologs of Identified LMP Genes

*Arabidopsis thaliana*

Full-length sequences of the *Arabidopsis thaliana* partial cDNAs (ESTs) that were identified in the SSH library and from MegaSort and MPSS EST sequencing were isolated by RACE PCR using the SMART RACE cDNA amplification kit from Clontech allowing both 5' and 3' rapid amplification of cDNA ends (RACE). The isolation of cDNAs and the RACE PCR protocol used were based on the manufacturer's conditions. The RACE product fragments were extracted from agarose gels with a QIAquick Gel Extraction Kit (Qiagen) and ligated into the TOPO pCR 2.1 vector (Invitrogen) following manufacturer's instructions. Recombinant vectors were transformed into TOP10 cells (Invitrogen) using standard conditions (Sambrook et al., 1989). Transformed cells were grown overnight at 37° C. on LB agar containing 50 μg/ml kanamycin and spread with 40 μl of a 40 mg/ml stock solution of X-gal in dimethylformamide for blue-white selection. Single white colonies were selected and used to inoculate 3 ml of liquid LB containing 50 μg/ml kanamycin and grown overnight at 37° C. Plasmid DNA was extracted using the QIAprep Spin Miniprep Kit (Qiagen) following manufacturer's instructions. Subsequent analyses of clones and restriction mapping was performed according to standard molecular biology techniques (Sambrook et al., 1989).

Gene sequences can be used to identify homologous or heterologous genes (orthologs, the same LMP gene from another plant) from cDNA or genomic libraries. This can be done by designing PCR primers to conserved sequences identified by multiple sequence alignments. Orthologs are often identified by designing degenerate primers to full-length or partial sequences of genes of interest. Homologous genes (e.g. full-length cDNA clones) can be isolated via nucleic acid hybridization using, for example, cDNA libraries: Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. Aqueous solution hybridization and washing is performed at an ionic strength of 1 M NaCl and a temperature of 68° C. Hybridization probes are generated by, e.g., radioactive ($^{32}P$) nick transcription labeling (High Prime, Roche, Mannheim, Germany). Signals are detected by autoradiography.

Partially homologous or heterologous genes that are related but not identical can be identified in a procedure analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only in a distinct domain (for example 10-20 amino acids) can be carried out by using synthetic radiolabeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide hybridization solution:

6×SSC
0.01 M sodium phosphate
1 mM EDTA (pH 8)
0.5% SDS
100 μg/ml denaturated salmon sperm DNA
0.1% nonfat dried milk During hybridization, temperature is lowered stepwise to 5-10° C. below the estimated oligonucleotide $T_m$ or down to room temperature followed by washing steps and autoradiography. Washing is performed with low stringency such as three washing steps using 4×SSC. Further details are described by Sambrook et al. (1989, "Molecular Cloning: A Laboratory Manual", Cold Spring Harbor Laboratory Press) or Ausubel et al. (1994, "Current Protocols in Molecular Biology", John Wiley & Sons).

*Brassica napus*

Clones of *Brassica napus* genes obtained from Hyseq were sequenced at using a ABI 377 slab gel sequencer and BigDye Terminator Ready Reaction kits (PE Biosystems, Foster City, Calif.). Gene specific primers were designed using these sequences, and genes were amplified from the plasmid supplied from Hyseq using touch-down PCR. In some cases, primers were designed to add an "AACA" Kozak-like sequence just upstream of the gene start codon and two bases downstream were, in some cases, changed to GC to facilitate increased gene expression levels (Chandrashekhar et al., 1997, Plant Molecular Biology 35:993-1001). PCR reaction cycles were: 94° C., 5 minutes; 9 cycles of 94° C., 1 minute, 65° C., 1 minute, 72° C., 4 minutes and in which the anneal temperature was lowered by 1° C. each cycle; 20 cycles of 94° C., 1 minute, 55° C., 1 minute, 72° C., 4 minutes; and the PCR cycle was ended with 72° C., 10 minutes. Amplified PCR products were gel purified from 1% agarose gels using GenElute—EtBr spin columns (Sigma), and after standard enzymatic digestion, were ligated into the plant binary vector pBPS-GB 1 for transformation of *Arabidopsis*. The binary vector was amplified by overnight growth in *E. coli* DH5 in LB media and appropriate antibiotic, and plasmid was prepared for downstream steps using Qiagen MiniPrep DNA preparation kit. The insert was verified throughout the various cloning steps by determining its size through restriction digest and inserts were sequenced in parallel to plant transformations to ensure the expected gene was used in *Arabidopsis* transformation.

RT-PCR and Cloning of *Arabidopsis thaliana, Brassica napus*, and *Physcomitrella patens* LMP Genes Full-length LMP eDNAs were isolated by RT-PCR from *Arabidopsis thaliana, Brassica napus*, or *Physcomitrella patens* RNA. The synthesis of the first strand cDNA was achieved using AMV Reverse Transcriptase (Roche, Mannheim, Germany). The resulting single-stranded cDNA was amplified via Polymerase Chain Reaction (PCR) utilizing two gene-specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C., and 1.5 minutes at 72° C. This was followed by thirty cycles of 40 seconds at 94° C., 40 seconds at 65° C., and 1.5 minutes at 72° C. The fragments generated under these RT-PCR conditions were analyzed by agarose gel electrophoresis to make sure that PCR products of the expected length had been obtained.

Full-length LMP cDNAs were isolated by using synthetic oligonucleotide primers (MWG-Biotech) designed based on the LMP gene specific DNA sequence that was determined by EST sequencing and by sequencing of RACE PCR products. The 5' PCR primers ("forward primer", F) for SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, and SEQ ID NO:115 contained an AscI restriction site 5' upstream of the ATG start codon. The 5' PCR primers ("forward primer", F) for SEQ ID NO:117, SEQ ID NO:119, SEQ ID NO:121, SEQ ID NO:123, SEQ ID NO:125, SEQ ID NO:127, SEQ ID NO:129, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:49, and SEQ ID NO:131, contained a NotI restriction site 5' upstream of the ATG start codon. The 3' PCR primers ("reverse primers", R) for SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, and SEQ ID NO:116 contained a PacI restriction site 3' downstream of the stop codon. The 3' PCR primers ("reverse primers", R) for SEQ ID NO:118, SEQ ID NO:120, SEQ ID NO:122, SEQ ID NO:124, SEQ ID NO:126, SEQ ID NO:128, SEQ ID NO:130, SEQ ID NO:134, SEQ ID NO:136, SEQ ID NO:138, and SEQ ID NO:140, contained a NotI restriction site 3' downstream of the stop codon. The 3' PCR primers ("reverse primers", R) for SEQ ID NO:142, SEQ ID NO:144, SEQ ID NO:146, SEQ ID NO:148, SEQ ID NO:150, SEQ ID NO:152, SEQ ID NO:156, SEQ ID NO:158, SEQ ID NO:160, SEQ ID NO:50, and SEQ ID NO:132, contained a StuI restriction site 3' downstream of the stop codon. The 3' PCR primers ("reverse primers", R) for SEQ ID NO:154 contained an EcoRV restriction site 3' downstream of the stop codon.

The restriction sites were added so that the RT-PCR amplification products could be cloned into the restriction sites located in the multiple cloning site of the binary vector. The following "forward" (F) and "reverse" (R) primers were used to amplify the full-length *Arabidopsis thaliana* or *Brassica napus* cDNAs by RT-PCR using RNA from *Arabidopsis thaliana* or *Brassica napus* as original template:

For amplification of SEQ ID NO:1

Pk123F (SEQ ID NO: 83)
(5'-ATGGCGCGCCATGGCAATCTTCCGAAGTACACTAGT-3')

Pk123R (SEQ ID NO: 84)
(5'-GCTTAATTAATTAAGGGCACTTGAGACGGCCA-3')

For amplification of SEQ ID NO:3

Pk197F (SEQ ID NO: 85)
(5'-ATGGCGCGCCAACAATGGAGAATGGAGCAACGACG-3')

Pk197R (SEQ ID NO: 86)
(5'-GCTTAATTAACTATATGGTTGGATATTGAGTCTTGGC-3')

For amplification of SEQ ID NO:5

Pk136F (SEQ ID NO: 87)
(5'-ATGGCGCGCCATGGCTGAAAAAGTAAAGTCTGGTCA-3')

Pk136R (SEQ ID NO: 88)
(5'-GCTTAATTAATTATAGCTCCTCAGATCCCTCCGA-3')

For amplification of SEQ ID NO:7

Pk156F (SEQ ID NO: 89)
(5'-ATGGCGCGCCATGGCTGGAGAAGAAATAGAGAGGG-3')

Pk156R (SEQ ID NO: 90)
(5'-GCTTAATTAATTAAACAGAGGCTTCTCTACTCTCACTT-3')

For amplification of SEQ ID NO:9

Pk159F (5'-ATGGCGCGCCATGGCTGGAGTGATGAAGTTGGC-3') (SEQ ID NO: 91)

Pk159R (5'-GCTTAATTAATCACCTCACGGTGTTGCAGTTG-3') (SEQ ID NO: 92)

For amplification of SEQ ID NO:11

Pk179F (SEQ ID NO: 93)
(5'-ATGGCGCGCCAAACAATGGGGCTTGCTGTGGTGG-3')

Pk179R (SEQ ID NO: 94)
(5'-GCTTAATTAATTACTGCAAGGCTTTCAATATATTTC-3')

For amplification of SEQ ID NO:13

Pk202F (SEQ ID NO: 95)
(5'-ATGGCGCGCCAACAATGGCGTTCACGGCGCTTGT-3')

Pk202R (SEQ ID NO: 96)
(5'-GCTTAATTAATCAACAAGTAGGATAAGGAACACCACA-3')

For amplification of SEQ ID NO:15

Pk206F (SEQ ID NO: 97)
(5'-ATGGCGCGCCAACAATGGCCCTTGATGAGCTTCTCAAG-3')

Pk206R (SEQ ID NO: 98)
(5'-GCTTAATTAATCAGAGAGAAGCAGAGTTTGTTCGC-3')

For amplification of SEQ ID NO:17

Pk207F (SEQ ID NO: 99)
(5'-ATGGCGCGCCAACAATGGCGCAATCCCGATTATTAG-3')

Pk207R (SEQ ID NO: 100)
(5'-GCTTAATTAATTAAAACCACTCGCCTCTCATTTC-3')

For amplification of SEQ ID NO:19

Pk209F (SEQ ID NO: 101)
(5'-ATGGCGCGCCATGTCCGTGGCTCGATTCGAT-3')

Pk209R (SEQ ID NO: 102)
(5'-GCTTAATTAACTAATCCTCTAGCTCGATGATTTTGAC-3')

For amplification of SEQ ID NO:21

Pk215F (SEQ ID NO: 103)
(5'-ATGGCGCGCCAACAATGGCGATTTACAGATCTCTAAGAAAG-3')

Pk215R (SEQ ID NO: 104)
(5'-GCTTAATTAATTACCTTAGATAAGTGATCCATGTCTGG-3')

For amplification of SEQ ID NO:23

Pk239F (SEQ ID NO: 105)
(5'-ATGGCGCGCCAACAATGGTAAAGGAAACTCTAATTCCTCCG-3')

Pk239R (SEQ ID NO: 106)
(5'-GCTTAATTAACTACCAGCCGAAGATTGGCTTGT-3')

For amplification of SEQ ID NO:25

Pk240F (5'-ATGGCGCGCCATTTGGAGAGCAATGGCGACTT-3') (SEQ ID NO: 107)

Pk240R (5'-GCTTAATTAATTACATCGAACGAAGAAGCATCAA-3') (SEQ ID NO: 108)

For amplification of SEQ ID NO:27

Pk241F (5'-ATGGCGCGCCCATCCTCAGAAAGAATGGCTCAAA-3') (SEQ ID NO: 109)

Pk241R (5'-GCTTAATTAATTAGCTTTCTTCACCATCATCGGTG-3') (SEQ ID NO: 110)

For amplification of SEQ ID NO:29

Pk242F (SEQ ID NO: 111)
(5'-ATGGCGCGCCAACAATGGGTGCAGGTGGAAGAATGCC-3')

Pk242R (SEQ ID NO: 112)
(5'-GCTTAATTAATCATAACTTATTGTTGTACCAGTACACACC-3')

For amplification of SEQ ID NO:31

Bn011F (SEQ ID NO: 113)
(5'-ATGGCGCGCCAACAATGGCTTCAATAAATGAAGATGTGTCT-3')

Bn011R (SEQ ID NO: 114)
(5'-GACTTAATTAATCAATTGGTGGGATTAACGACTCCA-3')

For amplification of SEQ ID NO:33

Bn077F (SEQ ID NO: 115)
(5'-ATGGCGCGCCAACAATGGCTACATTCTCTTGTAATTCT
TATGA-3')

Bn077R (SEQ ID NO: 116)
(5'-GACTTAATTAATCAGAAGCGGCCATTAAAATTACCCA-3')

For amplification of SEQ ID NO:35

Jb001F (SEQ ID NO: 117)
(5'-ATAAGAATGCGGCCGCCATGGCAACGGAATGCATTGCA-3')

Jb001R (SEQ ID NO: 118)
(5'-ATAAGAATGCGGCCGCTTAGAAACTTCTTCTGTTCTT-3')

For amplification of SEQ ID NO:37

Jb002F (SEQ ID NO: 119)
(5'-ATAAGAATGCGGCCGCCATGGCGTCAGAGCAAGCAAGG-3')

Jb002R (SEQ ID NO: 120)
(5'-ATAAGAATGCGGCCGCTCAACGTTGTCCATGTTCCCG-3')

For amplification of SEQ ID NO:39

Jb003F (SEQ ID NO: 121)
(5'-ATAAGAATGCGGCCGCCATGGCTAAGTCTTGCTATTTCA-3')

Jb003R (SEQ ID NO: 122)
(5'-ATAAGAATGCGGCCGCTCAGGCGCTATAGCCTAAGATT-3')

For amplification of SEQ ID NO:41

Jb005F (SEQ ID NO: 123)
(5'-ATAAGAATGCGGCCGCCATGGACGGTGCCGGAGAATCACGA-3')

Jb005R (SEQ ID NO: 124)
(5'-ATAAGAATGCGGCCGCCTAATAACTTAAAGTTACCGGA-3')

For amplification of SEQ ID NO:43

Jb007F (SEQ ID NO: 125)
(5'-ATAAGAATGCGGCCGCCATGTCGAGAGCTTTGTCAGTCG-3')

Jb007R (SEQ ID NO: 126)
(5'-ATAAGAATGCGGCCGCCATGTCGAGAGCTTTGTCAGTCG-3')

For amplification of SEQ ID NO:45

Jb009F (SEQ ID NO: 127)
(5'-ATAAGAATGCGGCCGCCATGGCAAGCAGCGACGTGAAGCT-3')

Jb009R (SEQ ID NO: 128)
(5'-ATAAGAATGCGGCCGCTCAACCAAGCCAAGAAGCACCC-3')

For amplification of SEQ ID NO:47

Jb013F (SEQ ID NO: 129)
(5'-ATAAGAATGCGGCCGCCATGGCGTCTCAACAAGAGAAGA-3')

Jb013R (SEQ ID NO: 130)
(5'-ATAAGAATGCGGCCGCTTAGGTCTTGGTCCTGAATTTG-3')

For amplification of SEQ ID NO:51

Jb017F (SEQ ID NO: 133)
(5'-ATAAGAATGCGGCCGCCATGGCTCCTTCAACAAAAGTTC-3')

Jb017R (SEQ ID NO: 134)
(5'-ATAAGAATGCGGCCGCTCAAACACTGCTGATAGTATTT-3')

For amplification of SEQ ID NO:53

Jb024F (SEQ ID NO: 135)
(5'-ATAAGAATGCGGCCGCCATGCGGTGCTTTCCACCTCCCT-3')

Jb024R (SEQ ID NO: 136)
(5'-ATAAGAATGCGGCCGCTTACTTTTGTAATGGTGAGAGC-3')

For amplification of SEQ ID NO:55

```
Jb027F
                                         (SEQ ID NO: 137)
(5'-ATAAGAATGCGGCCGCCATGCTTCTAATTCTAGCGATTT-3')

Jb027R
                                         (SEQ ID NO: 138)
(5'-ATAAGAATGCGGCCGCTCAGATAACCTTCTTCTTCTCG-3')
```

For amplification of SEQ ID NO:57

```
                                         (SEQ ID NO: 139)
OO-1F (5'-ATTGCGGCCGCACAATGGCACATGCCACGTTTACG-3')
                                         (SEQ ID NO: 140)
OO-1R (5'-ATTGCGGCCGCTTAGTCTTCATGGTCCCATAGATC-3')
```

For amplification of SEQ ID NO:59

```
                                         (SEQ ID NO: 141)
OO-2F (5'-GCGGCCGCCATGGCGTCTGAGAAACAAAAAC-3')
                                         (SEQ ID NO: 142)
OO-2R (5'-AGGCCTTTACGCATTTACCACAGCTCC-3')
```

For amplification of SEQ ID NO:61

```
                                         (SEQ ID NO: 143)
OO-3F (5'-GCGGCCGCATGGATTCAACGAAGCTTAGTGAGC-3')
                                         (SEQ ID NO: 144)
OO-3R (5'-AGGCCTTTACTGAGGTCCTGCAAATTTG-3')
```

For amplification of SEQ ID NO:63

```
                                         (SEQ ID NO: 145)
OO-4F (5'-GCGGCCGCCATGAAGGTTCACGAGACAAGA-3')
                                         (SEQ ID NO: 146)
OO-4R (5'-AGGCCTCTACTCTGGTTCGACATCGAC-3')
```

For amplification of SEQ ID NO:65

```
                                         (SEQ ID NO: 147)
OO-5F (5'-GCGGCCGCCATGTCTACCCCAGCTGAATC-3')
                                         (SEQ ID NO: 148)
OO-5R (5'-AGGCCTCTAATTGTAGAGATCATCATC-3')
```

For amplification of SEQ ID NO:67

```
                                         (SEQ ID NO: 149)
OO-6F (5'-GCGGCCGCCATGGACAAATCTAGTACCATG-3')
                                         (SEQ ID NO: 150)
OO-6R (5'-AGGCCTTCAGCTACCACCCTTTTGTTTGAG-3')
```

For amplification of SEQ ID NO:69

```
                                         (SEQ ID NO: 151)
OO-8F (5'-GCGGCCGCCATGGCGAAATCTCAGATCTGG-3')
                                         (SEQ ID NO: 152)
OO-8R (5'-AGGCCTTTAAGAAGAAGCAACGAACGTG-3')
```

For amplification of SEQ ID NO:71

```
                                         (SEQ ID NO: 153)
OO-9F (5'-GCGGCCGCCATGGCGTCGAGCGATGAGCG-3')
                                         (SEQ ID NO: 154)
OO-9R (5'-GATATCTTACGGGAACGGAGCCAATTTC-3')
```

For amplification of SEQ ID NO:73

```
                                         (SEQ ID NO: 155)
OO-10F (5'-GCGGCCGCCATGGCGACTCTTAAGGTTTCTG-3')
                                         (SEQ ID NO: 156)
OO-10R (5'-AGGCCTTTAAGCATCATCTTCACCGAG-3')
```

For amplification of SEQ ID NO:75

```
                                         (SEQ ID NO: 157)
OO-11F (5'-GCGGCCGCCATGGTGGATCTATTGAACTCG-3')
                                         (SEQ ID NO: 158)
OO-11R (5'-AGGCCTTTACAACTCTTGGATATTAAAC-3')
```

For amplification of SEQ ID NO:77

```
                                         (SEQ ID NO: 159)
OO-12F (5'-GCGGCCGCCATGGCTGGAAAACTCATGCAC-3')
                                         (SEQ ID NO: 160)
OO-12R (5'-AGGCCTTTATGGCTCGACAATGATCTTC-3')
```

For amplification of SEQ ID NO:79

```
                                         (SEQ ID NO: 49)
pp82F (5'-ATGGCGCGCCCGACATGAAGCGACGTTGAACG-3')
                                         (SEQ ID NO: 50)
pp82R (5'-GCTTAATTAACTTTCCGCAGCCTTCAGGCCGC-3')
```

For amplification of SEQ ID NO:81

```
Pk225F
                                         (SEQ ID NO: 131)
(5'-GGTTAATTAAGGCGCGCCCCCGGAAGCGATGCTGAG-3')
Pk225R
                                         (SEQ ID NO: 132)
(5'-ATCTCGAGGACGTCCCACAGCCACCGGATTC-3')
```

Example 7

Identification of Genes of Interest by Screening Expression Libraries with Antibodies The cDNA clones can be used to produce recombinant protein, for example, in *E. coli* (e.g. Qiagen QIAexpress pQE system). Recombinant proteins are then normally affinity purified via Ni-NTA affinity chromatography (Qiagen). Recombinant proteins can be used to produce specific antibodies for example by using standard techniques for rabbit immunization. Antibodies are affinity purified using a Ni-NTA column saturated with the recombinant antigen as described by Gu et al. (1994, BioTechniques 17:257-262). The antibody can then be used to screen expression cDNA libraries to identify homologous or heterologous genes via an immunological screening (Sambrook et al., 1989, Molecular Cloning: A Laboratory Manual", Cold Spring Harbor Laboratory Press; or Ausubel et al. 1994, "Current Protocols in Molecular Biology", John Wiley & Sons).

Example 8

Northern-Hybridization

For RNA hybridization, 20 μg of total RNA or 1 μg of poly-(A)+ RNA was separated by gel electrophoresis in 1.25% strength agarose gels using formaldehyde as described in Amasino (1986, Anal. Biochem. 152:304), transferred by capillary attraction using 10×SSC to positively charged nylon membranes (Hybond N+, Amersham, Braunschweig), immobilized by UV light, and pre-hybridized for 3 hours at 68° C. using hybridization buffer (10% dextran sulfate w/v, 1 M NaCl, 1% SDS, 100 μg/ml of herring sperm DNA). The labeling of the DNA probe with the Highprime DNA labeling kit (Roche, Mannheim, Germany) was carried out during the pre-hybridization using alpha-$^{32}$P dCTP (Amersham, Braunschweig, Germany). Hybridization was carried out after addition of the labeled DNA probe in the same buffer at 68° C. overnight. The washing steps were carried out twice for 15 minutes using 2×SSC and twice for 30 minutes using 1×SSC, 1% SDS at 68° C. The exposure of the sealed filters was carried out at −70° C. for a period of 1 day to 14 days.

Example 9

DNA Sequencing and Computational Functional Analysis

The SSH cDNA library as described in Examples 4 and 5 was used for DNA sequencing according to standard methods, in particular by the chain termination method using the ABI PRISM Big Dye Terminator Cycle Sequencing Ready Reaction Kit (Perkin-Elmer, Weiterstadt, Germany) Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al. (1989, Cold Spring Harbor Laboratory Press: ISBN 0-87969-309-6)) on a Qiagene DNA preparation robot (Qiagen, Hilden) according to the manufacturer's protocols. Sequencing primers with the following nucleotide sequences were used:

```
5'-CAGGAAACAGCTATGACC-3'       SEQ ID NO: 161

5'-CTAAAGGGAACAAAAGCTG-3'      SEQ ID NO: 162

5'-TGTAAAACGACGGCCAGT-3'       SEQ ID NO: 163
```

Sequences were processed and annotated using the software package EST-MAX commercially provided by Bio-Max (Munich, Germany). The program incorporates practically all bioinformatics methods important for functional and structural characterization of protein sequences. For reference see http://pedant.mips.biochem.mpg.de.

The most important algorithms incorporated in EST-MAX are: FASTA: Very sensitive protein sequence database searches with estimates of statistical significance (Pearson W. R., 1990, Rapid and sensitive sequence comparison with FASTP and FASTA. Methods Enzymol. 183:63-98); BLAST: Very sensitive protein sequence database searches with estimates of statistical significance (Altschul S. F., Gish W., Miller W., Myers E. W. and Lipman D. J. Basic local alignment search tool. J. Mol. Biol. 215:403-410). PREDATOR: High-accuracy secondary structure prediction from single and multiple sequences. (Frishman & Argos 1997, 75% accuracy in protein secondary structure prediction. Proteins 27:329-335). CLUSTAL W: Multiple sequence alignment (Thompson, J. D., Higgins, D. G. and Gibson, T. J. 1994, CLUSTAL W: improving the sensitivity of progressive multiple sequence alignment through sequence weighting, positions-specific gap penalties and weight matrix choice, Nucleic Acids Res. 22:4673-4680). TMAP: Transmembrane region prediction from multiply aligned sequences (Persson B. & Argos P. 1994, Prediction of transmembrane segments in proteins utilizing multiple sequence alignments, J. Mol. Biol. 237:182-192). ALOM2:Transmembrane region prediction from single sequences (Klein P., Kanehisa M., and DeLisi C. 1984, Prediction of protein function from sequence properties: A discriminant analysis of a database. Biochim. Biophys. Acta 787:221-226. Version 2 by Dr. K. Nakai). PROSEARCH: Detection of PROSITE protein sequence patterns. Kolakowski L. F. Jr., Leunissen J. A. M. and Smith J. E. 1992, ProSearch: fast searching of protein sequences with regular expression patterns related to protein structure and function. Biotechniques 13:919-921). BLIMPS: Similarity searches against a database of ungapped blocks (Wallace & Henikoff 1992, PATMAT: A searching and extraction program for sequence, pattern and block queries and databases, CABIOS 8:249-254. Written by Bill Alford).

Example 10

Plasmids for Plant Transformation

For plant transformation, various binary vectors such as a pBPS plant binary vector were used. Construction of the plant binary vectors was performed by ligation of the cDNA in sense or antisense orientation into the vector. In such vectors, a plant promoter was located 5-prime to the cDNA, where it activated transcription of the cDNA; and a polyadenylation sequence was located 3'-prime to the cDNA. Various plant promoters were used such as a constitutive promoter (Superpromoter), a seed-specific promoter, and a root-specific promoter. Tissue-specific expression was achieved by using a tissue-specific promoter. For example, in some instances, seed-specific expression was achieved by cloning the napin or LeB4 or USP promoter 5-prime to the cDNA. Also, any other seed specific promoter element can be used, and such promoters are well known to one of ordinary skill in the art. For constitutive expression within the whole plant, in some instances, the Superpromoter or the CaMV 35S promoter was used. The expressed protein also can be targeted to a cellular compartment using a signal peptide, for example for plastids, mitochondria, or endoplasmic reticulum (Kermode, 1996, Crit. Rev. Plant Sci. 15:285-423). The signal peptide is cloned 5-prime in frame to the cDNA to achieve subcellular localization of the fusion protein.

The plant binary vectors comprised a selectable marker gene driven under the control of one of various plant promoters, such as the AtAct2-I promoter and the Nos-promoter; the LMP candidate cDNA under the control of a root-specific promoter, a seed-specific promoter, a non-tissue specific promoter, or a constitutive promoter; and a terminator. Partial or full-length LMP cDNA was cloned into the plant binary vector in sense or antisense orientation behind the desired promoter. The recombinant vector containing the gene of interest was transformed into Top10 cells (Invitrogen) using standard conditions. Transformed cells were selected for on LB agar containing the selective agent, and cells were grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al., 1989, Molecular Cloning, A Laboratory Manual. 2nd Edition. Cold Spring Harbor Laboratory Press. Cold Spring Harbor, N.Y.).

Example 11

*Agrobacterium* Mediated Plant Transformation

Agrobacterium mediated plant transformation with the LMP nucleic acids described herein can be performed using standard transformation and regeneration techniques (Gelvin, Stanton B. & Schilperoort R. A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993). For example, *Agrobacterium* mediated transformation can be performed using the GV3 (pMP90) (Koncz & Schell, 1986, Mol. Gen. Genet. 204:383-396) or LBA4404 (Clontech) *Agrobacterium tumefaciens* strain.

*Arabidopsis thaliana* can be grown and transformed according to standard conditions (Bechtold, 1993, Acad. Sci. Paris. 316:1194-1199; Bent et al., 1994, Science 265:1856-1860). Additionally, rapeseed can be transformed with the LMR nucleic acids of the present invention via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. Additionally, *Agrobacterium* mediated gene transfer to flax can be performed using, for example, a technique described by Mlynarova et al. (1994, Plant Cell Report 13:282-285).

Transformation of soybean can be performed using for example a technique described in EP 0424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) Clorox supplemented with 0.05% (v/v) Tween for 20 minutes with continuous shaking. Then the seeds are rinsed four times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

The method of plant transformation is also applicable to *Brassica* and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

hd *Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige & Skoog, 1962, Physiol. Plant. 15:473-497) medium supplemented with 100 mM acetosyringone. Bacteria cultures are incubated in this pre-induction medium for 2 hours at room temperature before use. The axis of soybean zygotic seed embryos at approximately 44% moisture content are imbibed for 2 h at room temperature with the pre-induced *Agrobacterium* suspension culture. (The imbibition of dry embryos with a culture of *Agrobacterium* is also applicable to maize embryo axes).

The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the *agrobacteria*. The liquid medium is used to moisten the sterile filter paper. The embryos are incubated during 4 weeks at 25° C., under 440 μmol $m^{-2}s^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 μmol $m^{-2}s^{-1}$ light intensity and 12 h photoperiod for about 80 days.

Samples of the primary transgenic plants ($T_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR as recommended by the manufacturer.

Example 12

In Vivo Mutagenesis

In vivo mutagenesis of microorganisms can be performed by incorporation and passage of the plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp W. D. 1996, DNA repair mechanisms, in: *Escherichia coli* and *Salmonella*, p. 2277-2294, ASM: Washington.) Such strains are well known to those skilled in the art. The use of such strains is illustrated, for example, in Greener and Callahan, 1994, Strategies 7:32-34. Transfer of mutated DNA molecules into plants is preferably done after selection and testing in microorganisms. Transgenic plants are generated according to various examples within the exemplification of this document.

Example 13

Assessment of the mRNA Expression and Activity of a Recombinant Gene Product in the Transformed Organism The activity of a recombinant gene product in the transformed host organism can be measured on the transcriptional level or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (See, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al., 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 14

In vitro Analysis of the Function of *Arabidopsis thaliana* and *Brassica napus* Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M. & Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N.C., Stevens, L., 1982, Fundamentals of Enzymology. Oxford Univ. Press: Oxford; Boyer, P. D., ed. (1983) The Enzymes, 3rd ed. Academic Press: New York; Bisswanger, H., 1994, Enzymkinetik, 2nd ed. VCH: Weinheim (ISBN 3527300325); Bergmeyer, H. U., Bergmeyer, J., Graβl, M., eds. (1983-1986) Methods of Enzymatic Analysis, 3rd ed., vol. I-XII, Verlag Chemie: Weinheim; and Ullmann's Encyclopedia of Industrial Chemistry (1987) vol. A9, Enzymes. VCH: Weinheim, p. 352-363.

Example 15

Analysis of the Impact of Recombinant LMPs on the Production of a Desired Seed Storage Compound: Fatty Acid Production The total fatty acid content of *Arabidopsis* seeds was determined by saponification of seeds in 0.5 M KOH in methanol at 80° C. for 2 hours followed by LC-MS analysis of the free fatty acids. Total fatty acid content of seeds of control and transgenic plants was measured with bulked seeds (usually 5 mg seed weight) of a single plant. Three different types of controls have been used: Col-2 (Columbia-2, the *Arabidopsis* ecotype in which SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:79, or SEQ ID NO:81 has been transformed), Col-0 (Columbia-0, the *Arabidopsis* ecotype in which SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, or SEQ ID NO:77 has been transformed), C-24 (an *Arabidopsis* ecotype found to accumulate high amounts of total fatty acids in seeds), and the BPS empty (without an LMP gene of interest) binary vector construct. The controls indicated in the tables below have been grown side by side with the transgenic lines. Differences in the total values of the controls are explained either by differences in the growth conditions, which were found to be very sensitive to small variations in the plant cultivation, or by differences in the standards added to quantify the fatty acid content. Because of the seed bulking, all values obtained with T2 seeds, and in part also with T3 seeds, are the result of a mixture of homozygous (for the gene of interest) and heterozygous events, implying that these data underestimate the LMP gene effect.

TABLE 5

Determination of the T2 seed total fatty acid content of transgenic lines of pk123 (containing SEQ ID NO: 1).

| Genotype | g total fatty acids/ g seed weight |
|---|---|
| C-24 wild-type control | 0.318 ± 0.022 |
| Col-2 wild-type control | 0.300 ± 0.023 |
| Pk123 transgenic seeds | 0.319 ± 0.024 |

Shown are the means (±standard deviation). (Average mean values are shown ± standard deviation, number of individual measurements per plant line: 12-20; Col-2 is the *Arabidopsis* ecotype the LMP gene has been transformed in, C-24 is a high-oil *Arabidopsis* ecotype used as another control).

TABLE 6

Determination of the T2 seed total fatty acid content of transgenic lines of pk197 (containing SEQ ID NO: 3).

| Genotype | g total fatty acids/ g seed weight |
|---|---|
| C-24 wild-type control | 0.371 ± 0.010 |
| Col-2 wild-type control | 0.353 ± 0.017 |
| Col-2 empty vector control | 0.347 ± 0.024 |
| Pk197 transgenic seeds | 0.366 ± 0.014 |

Shown are the means (±standard deviation) of 6 individual plants per line.

TABLE 7

Determination of the T2 seed total fatty acid content of transgenic lines of pk136 (containing SEQ ID NO: 5).

| Genotype | g total fatty acids/ g seed weight |
|---|---|
| C-24 wild-type control | 0.351 ± 0.052 |
| Col-2 wild-type control | 0.344 ± 0.026 |
| Col-2 empty vector control | 0.346 ± 0.019 |
| Pk136 transgenic seeds | 0.374 ± 0.033 |

Shown are the means (±standard deviation) of 6 individual plants per line.

TABLE 8

Determination of the T2 seed total fatty acid content of transgenic lines of pk156 (containing SEQ ID NO: 7).

| Genotype | g total fatty acids/ g seed weight |
|---|---|
| C-24 wild-type control | 0.400 ± 0.001 |
| Col-2 wild-type control | 0.369 ± 0.043 |
| Pk156 transgenic seeds | 0.389 ± 0.007 |

Shown are the means (±standard deviation) of 6 individual plants per line each.

TABLE 9

Determination of the T2 seed total fatty acid content of transgenic lines of pk159 (containing SEQ ID NO: 9).

| Genotype | g total fatty acids/ g seed weight |
|---|---|
| C-24 wild-type control | 0.413 ± 0.019 |
| Col-2 wild-type control | 0.381 ± 0.019 |
| Pk159 transgenic seeds | 0.409 ± 0.008 |

Shown are the means (±standard deviation) of 6 individual plants per line.

TABLE 10

Determination of the T2 seed total fatty acid content of transgenic lines of pk179 (containing SEQ ID NO: 11).

| Genotype | g total fatty acids/ g seed weight |
|---|---|
| C-24 wild-type control | 0.400 ± 0.033 |
| Col-2 wild-type control | 0.339 ± 0.033 |
| Col-2 empty vector control | 0.357 ± 0.021 |
| Pk179 transgenic seeds | 0.384 ± 0.020 |

Shown are the means (±standard deviation) of 6 individual plants per line.

TABLE 11

Determination of the T2 seed total fatty acid content of transgenic lines of pk202 (containing SEQ ID NO: 13).

| Genotype | g total fatty acids/ g seed weight |
|---|---|
| C-24 wild-type control | 0.413 ± 0.019 |
| Col-2 wild-type control | 0.381 ± 0.019 |
| Col-2 empty vector control | 0.407 ± 0.020 |
| Pk202 transgenic seeds | 0.426 ± 0.033 |

Shown are the means (±standard deviation) of 6 individual plants per line.

TABLE 12

Determination of the T2 seed total fatty acid content of transgenic lines of pk206 (containing SEQ ID NO: 15).

| Genotype | g total fatty acids/ g seed weight |
|---|---|
| C-24 wild-type control | 0.422 ± 0.013 |
| Col-2 wild-type control | 0.354 ± 0.026 |
| Col-2 empty vector control | 0.388 ± 0.023 |
| Pk206 transgenic seeds | 0.414 ± 0.031 |

Shown are the means (±standard deviation) of 6 individual plants per line.

TABLE 13

Determination of the T2 seed total fatty acid content of transgenic lines of pk207 (containing SEQ ID NO: 17).

| Genotype | g total fatty acids/ g seed weight |
|---|---|
| C-24 wild-type control | 0.371 ± 0.010 |
| Col-2 wild-type control | 0.353 ± 0.017 |
| Col-2 empty vector control | 0.347 ± 0.024 |
| Pk207 transgenic seeds | 0.370 ± 0.009 |

Shown are the means (±standard deviation) of 6 individual plants per line.

TABLE 14

Determination of the T2 seed total fatty acid content of transgenic lines of pk209 (containing SEQ ID NO: 19).

| Genotype | g total fatty acids/ g seed weight |
|---|---|
| C-24 wild-type control | 0.400 ± 0.001 |
| Col-2 wild-type control | 0.369 ± 0.043 |
| Pk209 transgenic seeds | 0.397 ± 0.007 |

Shown are the means (±standard deviation) of 6 individual plants per line.

TABLE 15

Determination of the T2 seed total fatty acid content of transgenic lines of pk215 (containing SEQ ID NO: 21).

| Genotype | g total fatty acids/ g seed weight |
|---|---|
| C-24 wild-type control | 0.373 ± 0.045 |
| Col-2 wild-type control | 0.344 ± 0.026 |
| Col-2 empty vector control | 0.346 ± 0.019 |
| Pk215 transgenic seeds | 0.401 ± 0.014 |

Shown are the means (±standard deviation) of 6 individual plants per line.

TABLE 16

Determination of the T3 seed total fatty acid content of transgenic lines of pk239 (containing SEQ ID NO: 23).

| Genotype | g total fatty acids/ g seed weight |
|---|---|
| C-24 wild-type control | 0.334 ± 0.030 |
| Col-2 empty vector control | 0.301 ± 0.027 |
| Pk239-2 transgenic seeds | 0.335 ± 0.028 |
| Pk239-9 transgenic seeds | 0.335 ± 0.018 |
| Pk239-18 transgenic seeds | 0.331 ± 0.026 |
| Pk239-20 transgenic seeds | 0.343 ± 0.022 |

Shown are the means (±standard deviation) of 14-20 individual plants per line.

TABLE 17

Determination of the T3 seed total fatty acid content of transgenic lines of pk240 (containing SEQ ID NO: 25).

| Genotype | g total fatty acids/ g seed weight |
|---|---|
| C-24 wild-type control | 0.393 ± 0.037 |
| Col-2 empty vector control | 0.342 ± 0.024 |
| Pk240-3 transgenic seeds | 0.373 ± 0.033 |
| Pk240-6 transgenic seeds | 0.388 ± 0.015 |
| Pk240-10 transgenic seeds | 0.393 ± 0.025 |

Shown are the means (±standard deviation) of 10-20 individual plants per line.

TABLE 18

Determination of the T2 seed total fatty acid content of transgenic lines of pk241 (containing SEQ ID NO: 27).

| Genotype | g total fatty acids/ g seed weight |
|---|---|
| Col-2 wild-type control | 0.312 ± 0.033 |
| Col-2 empty vector control | 0.305 ± 0.025 |
| Pk241 transgenic seeds | 0.336 ± 0.032 |

Shown are the means (±standard deviation) of 10 (controls) and 30 (pk241) individual plants per line, respectively.

TABLE 19

Determination of the T2 seed total fatty acid content of transgenic lines of Pk242 (containing SEQ ID NO: 29).

| Genotype | g total fatty acids/ g seed weight |
|---|---|
| Col-2 wild-type control | 0.344 ± 0.016 |
| Col-2 empty vector control | 0.333 ± 0.040 |
| Pk242 transgenic seeds | 0.364 ± 0.008 |

Shown are the means (±standard deviation) of 6 individual plants per line.

TABLE 20

Determination of the T2 seed total fatty acid content of transgenic lines of Bn011 (containing SEQ ID NO: 31).

| Genotype | g total fatty acids/ g seed weight |
|---|---|
| C-24 wild-type control | 0.334 ± 0.028 |
| Col-2 wild-type control | 0.286 ± 0.039 |
| Col-2 empty vector control | 0.291 ± 0.034 |
| Bn011 transgenic seeds | 0.308 ± 0.030 |

Shown are the means (±standard deviation) of 14-20 individual plants per line.

TABLE 21

Determination of the T2 seed total fatty acid content of transgenic lines of Bn077 (containing SEQ ID NO: 33).

| Genotype | g total fatty acids/ g seed weight |
|---|---|
| C-24 wild-type control | 0.366 ± 0.056 |
| Col-2 wild-type control | 0.290 ± 0.047 |
| Col-2 empty vector control | 0.292 ± 0.038 |
| Bn077 transgenic seeds | 0.314 ± 0.032 |

Shown are the means (±standard deviation) of 8-17 individual plants per line.

TABLE 22

Determination of the T2 seed total fatty acid content of transgenic lines of Jb001 (containing SEQ ID NO: 35).

| Genotype | g total fatty acids/ g seed weight |
|---|---|
| Col-0 empty vector control | 0.241 ± 0.012 |
| Jb001 transgenic seeds | 0.274 ± 0.003 |

Shown are the means (±standard deviation) of 3 individual control plants and 2 individual plants per line.

TABLE 23

Determination of the T2 seed total fatty acid content of transgenic lines of Jb002 (containing SEQ ID NO: 37).

| Genotype | g total fatty acids/ g seed weight |
|---|---|
| Col-0 empty vector control | 0.191 ± 0.044 |
| Jb002 transgenic seeds | 0.273 ± 0.020 |

Shown are the means (±standard deviation) of 3 individual control plants and 5 individual plants per line.

TABLE 24

Determination of the T2 seed total fatty acid content of transgenic lines of Jb003 (containing SEQ ID NO: 39).

| Genotype | g total fatty acids/ g seed weight |
|---|---|
| Col-0 empty vector control | 0.267 ± 0.011 |
| Jb003 transgenic seeds | 0.297 ± 0.030 |

Shown are the means (±standard deviation) of 3 individual control plants and 2 individual plants per line.

TABLE 25

Determination of the T2 seed total fatty acid content of transgenic lines of Jb005 (containing SEQ ID NO: 41).

| Genotype | g total fatty acids/ g seed weight |
|---|---|
| Col-0 empty vector control | 0.229 ± 0.021 |
| Jb005 transgenic seeds | 0.264 ± 0.010 |

Shown are the means (±standard deviation) of 3 individual control plants and 7 individual plants per line.

TABLE 26

| Determination of the T2 seed total fatty acid content of transgenic lines of Jb007 (containing SEQ ID NO: 43). | |
|---|---|
| Genotype | g total fatty acids/ g seed weight |
| Col-0 empty vector control | 0.296 ± 0.017 |
| Jb007 transgenic seeds | 0.320 ± 0.002 |

Shown are the means (±standard deviation) of 3 individual control plants and 5 individual plants per line.

TABLE 27

| Determination of the T2 seed total fatty acid content of transgenic lines of Jb009 (containing SEQ ID NO: 45). | |
|---|---|
| Genotype | g total fatty acids/ g seed weight |
| Col-0 empty vector control | 0.227 ± 0.016 |
| Jb009 transgenic seeds | 0.238 ± 0.004 |

Shown are the means (±standard deviation) of 3 individual control plants and 3 individual plants per line.

TABLE 28

| Determination of the T2 seed total fatty acid content of transgenic lines of Jb013 (containing SEQ ID NO: 47). | |
|---|---|
| Genotype | g total fatty acids/ g seed weight |
| Col-0 empty vector control | 0.243 ± 0.011 |
| Jb013 transgenic seeds | 0.262 ± 0.007 |

Shown are the means (±standard deviation) of 3 individual control plants and 4 individual plants per line.

TABLE 29

| Determination of the T2 seed total fatty acid content of transgenic lines of Jb017 (containing SEQ ID NO: 51). | |
|---|---|
| Genotype | g total fatty acids/ g seed weight |
| Col-0 empty vector control | 0.231 ± 0.020 |
| Jb017 transgenic seeds | 0.269 ± 0.022 |

Shown are the means (±standard deviation) of 3 individual control plants and 2 individual plants per line.

TABLE 30

| Determination of the T2 seed total fatty acid content of transgenic lines of Jb027 (containing SEQ ID NO: 55). | |
|---|---|
| Genotype | g total fatty acids/ g seed weight |
| Col-0 empty vector control | 0.235 ± 0.052 |
| Jb027 transgenic seeds | 0.282 ± 0.014 |

Shown are the means (±standard deviation) of 3 individual control plants and 2 individual plants per line.

TABLE 31

| Determination of the T2 seed total fatty acid content of transgenic lines of OO-1 (containing SEQ ID NO: 57). | |
|---|---|
| Genotype | g total fatty acids/ g seed weight |
| Col-0 empty vector control | 0.250 ± 0.009 |
| OO-1 transgenic seeds | 0.274 ± 0.007 |

Shown are the means (±standard deviation) of 3 individual control plants and 7 individual plants per line.

TABLE 32

| Determination of the T2 seed total fatty acid content of transgenic lines of OO-4 (containing SEQ ID NO: 63). | |
|---|---|
| Genotype | g total fatty acids/ g seed weight |
| Col-0 empty vector control | 0.329 ± 0.041 |
| OO-4 transgenic seeds | 0.380 ± 0.015 |

Shown are the means (±standard deviation) of 2 individual control plants and 4 individual plants per line.

TABLE 33

| Determination of the T2 seed total fatty acid content of transgenic lines of OO-8 (containing SEQ ID NO: 69). | |
|---|---|
| Genotype | g total fatty acids/ g seed weight |
| Col-0 empty vector control | 0.379 ± 0.009 |
| OO-8 transgenic seeds | 0.411 ± 0.008 |

Shown are the means (±standard deviation) of 4 individual control plants and 2 individual plants per line.

TABLE 34

| Determination of the T2 seed total fatty acid content of transgenic lines of OO-9 (containing SEQ ID NO: 71). | |
|---|---|
| Genotype | g total fatty acids/ g seed weight |
| Col-0 empty vector control | 0.315 ± 0.020 |
| OO-9 transgenic seeds | 0.333 ± 0.006 |

Shown are the means (±standard deviation) of 3 individual control plants and 4 individual plants per line.

TABLE 35

| Determination of the T2 seed total fatty acid content of transgenic lines of OO-11 (containing SEQ ID NO: 75). | |
|---|---|
| Genotype | g total fatty acids/ g seed weight |
| Col-0 empty vector control | 0.264 ± 0.003 |
| OO-11 transgenic seeds | 0.278 ± 0.003 |

Shown are the means (±standard deviation) of 3 individual control plants and 2 individual plants per line.

TABLE 36

Determination of the T2 seed total fatty acid content of transgenic lines of OO-12 (containing SEQ ID NO: 77).

| Genotype | g total fatty acids/ g seed weight |
|---|---|
| Col-0 empty vector control | 0.290 ± 0.010 |
| OO-12 transgenic seeds | 0.316 ± 0.008 |

Shown are the means (±standard deviation) of 3 individual control plants and 9 individual plants per line.

TABLE 37

Determination of the T4 seed total fatty acid content of transgenic lines of pp82 (containing SEQ ID NO: 79).

| Genotype | g total fatty acids/ g seed weight |
|---|---|
| C-24 wild-type control | 0.436 ± 0.050 |
| Col-2 wild-type control | 0.380 ± 0.020 |
| Col-2 empty vector control | 0.378 ± 0.030 |
| pp82-15-16 transgenic seeds | 0.432 ± 0.040 |
| pp82-15-19 transgenic seeds | 0.437 ± 0.040 |
| pp82-16-10 transgenic seeds | 0.430 ± 0.040 |
| pp82-9-14 transgenic seeds | 0.449 ± 0.040 |

Shown are the means (±standard deviation) of 17-20 individual plants per line.

TABLE 38

Determination of the T4 seed total fatty acid content of transgenic lines of pk225 (containing SEQ ID NO: 81).

| Genotype | g total fatty acids/ g seed weight |
|---|---|
| C-24 wild-type control | 0.344 ± 0.048 |
| Col-2 empty vector control | 0.327 ± 0.031 |
| Pk225-11-19 transgenic seeds | 0.350 ± 0.041 |
| Pk225-19-8 transgenic seeds | 0.351 ± 0.021 |
| Pk225-7-6 transgenic seeds | 0.354 ± 0.037 |
| Pk225-9-10 transgenic seeds | 0.363 ± 0.042 |

This particular gene has been down-regulated. Shown are the means (±standard deviation) of 17-20 individual plants per line.

TABLE 39

Determination of the T2 seed total fatty acid content of transgenic lines of OO-3 (containing SEQ ID NO: 61).

| Genotype | g total fatty acids/ g seed weight |
|---|---|
| Col-0 empty vector control | 0.365 ± 0.006 |
| OO-3 transgenic seeds | 0.388 ± 0.006 |

Shown are the means (±standard deviation) of 4 individual control plants and 6 individual plants per line.

Example 16

Analysis of the Impact of Recombinant Proteins on the Production of a Desired Seed Storage Compound The effect of the genetic modification in plants on a desired seed storage compound (such as a sugar, lipid or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (See, for example, Ullman, 1985, Encyclopedia of Industrial Chemistry, vol. A2, pp. 89-90 and 443-613, VCH: Weinheim; Fallon, A. et al., 1987, Applications of HPLC in Biochemistry in: Laboratory Techniques in Biochemistry and Molecular Biology, vol. 17; Rehm et al., 1993, Product recovery and purification, Biotechnology, vol. 3, Chapter III, pp. 469-714, VCH: Weinheim; Belter, P. A. et al., 1988, Bioseparations: downstream processing for biotechnology, John Wiley & Sons; Kennedy J. F. & Cabral J. M. S., 1992, Recovery processes for biological materials, John Wiley and Sons; Shaeiwitz J. A. & Henry J. D., 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland: Oily Press.—(Oily Press Lipid Library; Christie, William W., Gas Chromatography and Lipids. A Practical Guide—Ayr, Scotland: Oily Press, 1989 Repr. 1992.—IX, 307 S.—(Oily Press Lipid Library; and "Progress in Lipid Research, Oxford: Pergamon Press, 1 (1952)-16 (1977) Progress in the Chemistry of Fats and Other Lipids CODEN.

Unequivocal proof of the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240) and for seeds by Focks & Benning (1998, Plant Physiol. 118:91-101).

Positional analysis of the fatty acid composition at the C-1, C-2 or C-3 positions of the glycerol backbone is determined by lipase digestion (See, e.g., Siebertz & Heinz 1977, Z. Naturforsch. 32c:193-205, and Christie, 1987, Lipid Analysis 2nd Edition, Pergamon Press, Exeter, ISBN 0-08-023791-6).

A typical way to gather information regarding the influence of increased or decreased protein activities on lipid and sugar biosynthetic pathways is for example via analyzing the carbon fluxes by labeling studies with leaves or seeds using $^{14}$C-acetate or $^{14}$C-pyruvate (See, e.g. Focks & Benning, 1998, Plant Physiol. 118:91-101; Eccleston & Ohlrogge, 1998, Plant Cell 10:613-621). The distribution of carbon-14 into lipids and aqueous soluble components can be determined by liquid scintillation counting after the respective separation (for example on TLC plates) including standards like $^{14}$C-sucrose and $^{14}$C-malate (Eccleston & Ohlrogge, 1998, Plant Cell 10:613-621).

Material to be analyzed can be disintegrated via sonification, glass milling, liquid nitrogen and grinding, or via other applicable methods. The material has to be centrifuged after disintegration. The sediment is resuspended in distilled water, heated for 10 minutes at 100° C., cooled on ice and centrifuged again, followed by extraction in 0.5 M sulfuric acid in methanol containing 2% dimethoxypropane for 1 hour at 90° C., leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 minutes at 240° C. The identity of resulting fatty acid methylesters is defined by the use of standards available form commercial sources (e.g., Sigma).

In the case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves," Methods Enzymol. 174:518-552; for other methods, see also Härtel et al., 1998, Plant Physiol. Biochem. 36:407-417 and Focks & Benning, 1998, Plant Physiol. 118:91-101).

For the extraction of soluble sugars and starch, 50 seeds are homogenized in 500 μl of 80% (v/v) ethanol in a 1.5-ml polypropylene test tube and incubated at 70° C. for 90 minutes. Following centrifugation at 16,000 g for 5 minutes, the supernatant is transferred to a new test tube. The pellet is extracted twice with 500 μl of 80% ethanol. The solvent of the combined supernatants is evaporated at room temperature under a vacuum. The residue is dissolved in 50 μl of water, representing the soluble carbohydrate fraction. The pellet left from the ethanol extraction, which contains the insoluble carbohydrates including starch, is homogenized in 200 μl of 0.2 N KOH, and the suspension is incubated at 95° C. for 1 hour to dissolve the starch. Following the addition of 35 μl of 1 N acetic acid and centrifugation for 5 minutes at 16,000 g, the supernatant is used for starch quantification.

To quantify soluble sugars, 10 μl of the sugar extract is added to 990 μl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose, and sucrose, 4.5 units of hexokinase, 1 unit of phosphoglucoisomerase, and 2 μl of a saturated fructosidase solution are added in succession. The production of NADPH is photometrically monitored at a wavelength of 340 nm. Similarly, starch is assayed in 30 μl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding," Anal. Biochem. 72:248-254). For quantification of total seed protein, 15-20 seeds are homogenized in 250 μl of acetone in a 1.5-ml polypropylene test tube. Following centrifugation at 16,000 g, the supernatant is discarded and the vacuum-dried pellet is resuspended in 250 μl of extraction buffer containing 50 mM Tris-HCl, pH 8.0, 250 mM NaCl, 1 mM EDTA, and 1% (w/v) SDS. Following incubation for 2 h at 25° C., the homogenate is centrifuged at 16,000 g for 5 min and 200 ml of the supernatant will be used for protein measurements. In the assay, γ-globulin is used for calibration. For protein measurements, Lowry D C protein assay (Bio-Rad) or Bradford-assay (Bio-Rad) are used.

Enzymatic assays of hexokinase and fructokinase are performed spectrophotometrically according to Renz et al. (1993, Planta 190:156-165); enzymatic assays of phospho-gluco-isomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase and pyruvate kinase are performed according to Burrell et al. (1994, Planta 194:95-101); and enzymatic assays of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Härtel et al. (1998, Plant Physiol. Biochem. 36:407-417), and metabolites are measured as described in Jelitto et al. (1992, Planta 188:238-244).

In addition to the measurement of the final seed storage compound (i.e., lipid, starch or storage protein), it is also possible to analyze other components of the metabolic pathways utilized for the production of a desired seed storage compound, such as intermediates and side-products, to determine the overall efficiency of production of the compound (Fiehn et al., 2000, Nature Biotech. 18:1447-1161).

For example, yeast expression vectors comprising the nucleic acids disclosed herein, or fragments thereof, can be constructed and transformed into *Saccharomyces cerevisiae* using standard protocols. The resulting transgenic cells can then be assayed for alterations in sugar, oil, lipid, or fatty acid contents.

Similarly, plant expression vectors comprising the nucleic acids disclosed herein, or fragments thereof, can be constructed and transformed into an appropriate plant cell such as *Arabidopsis*, soybean, rape, maize, wheat, *Medicago truncatula*, etc., using standard protocols. The resulting transgenic cells and/or plants derived therefrom can then be assayed for alterations in sugar, oil, lipid, or fatty acid contents.

Additionally, the sequences disclosed herein, or fragments thereof, can be used to generate knockout mutations in the genomes of various organisms, such as bacteria, mammalian cells, yeast cells, and plant cells (Girke at al., 1998, Plant J. 15:39-48). The resultant knockout cells can then be evaluated for their composition and content in seed storage compounds, and the effect on the phenotype and/or genotype of the mutation. For other methods of gene inactivation include U.S. Pat. No. 6,004,804 and Puttaraju et al., 1999, Nature Biotech. 17:246-252).

Example 17

Purification of the Desired Product from Transformed Organisms

An LMP can be recovered from plant material by various methods well known in the art. Organs of plants can be separated mechanically from other tissue or organs prior to isolation of the seed storage compound from the plant organ. Following homogenization of the tissue, cellular debris is removed by centrifugation and the supernatant fraction containing the soluble proteins is retained for further purification of the desired compound. If the product is secreted from cells grown in culture, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey J. E. & Ollis D. F., 1986, Biochemical Engineering Fundamentals, McGraw-Hill: New York.

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzymatic assay, or microbiologically. Such analysis methods are reviewed in: Patek et al. (1994, Appl. Environ. Microbiol. 60:133-140), Malakhova et al. (1996, Biotekhnologiya 11:27-32), Schmidt et al. (1998, Bioprocess Engineer 19:67-70), Ulmann's Encyclopedia of Industrial Chemistry (1996, Vol. A27, VCH: Weinheim, p. 89-90, p. 521-540, p. 540-547, p. 559-566, 575-581 and p. 581-587) and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

Example 18

Screening for Increased Stress Tolerance and Plant Growth

The transgenic plants are screened for their improved stress tolerance demonstrating that transgene expression confers stress tolerance. The transgenic plants are further screened for their growth rate demonstrating that transgene expression confers increased growth rates and/or increased seed yield.

Classification of the proteins was done by Blasting against the BLOCKS database (S. Henikoff & J. G. Henikoff, "Protein family classification based on searching a database of blocks", Genomics 19:97-107 (1994)).

Those skilled in the art will recognize, or will be able to ascertain using no more than routine experimentation, many equivalents to the specific embodiments of the invention described herein. Such equivalents are intended to be encompasses by the claims to the invention disclosed and claimed herein.

We claim:

1. An expression vector comprising an isolated nucleic acid comprising a polynucleotide sequence encoding a polypeptide that functions in increasing fatty acid content in a seed, wherein the polynucleotide sequence is selected from the group consisting of:

a) the polynucleotide sequence of SEQ ID NO: 25;

b) a polynucleotide sequence encoding a polypeptide comprising the amino acid sequence of SEQ ID NO: 26; and c) a polynucleotide sequence encoding a polypeptide comprising an amino acid sequence having at least 95% sequence identity with the amino acid sequence of SEQ ID NO: 26.

2. The expression vector of claim 1, wherein the nucleic acid is operatively linked to a heterologous promoter selected from the group consisting of a seed-specific promoter, a root-specific promoter, and a non-tissue-specific promoter.

3. A method of producing a transgenic plant having an increased level of fatty acid in a seed as compared to a corresponding wild type variety of the plant comprising, transforming a plant cell with the expression vector of claim 1 and generating from the plant cell a transgenic plant.

4. The method of claim 3, wherein the nucleic acid comprises the polynucleotide sequence of SEQ ID NO: 25.

5. The method of claim 3, wherein the nucleic acid comprises a polynucleotide sequence encoding the polypeptide of SEQ ID NO: 26.

6. The method of claim 3, wherein the nucleic acid is operatively linked to a heterologous promoter selected from the group consisting of a seed-specific promoter, a root-specific promoter, and a non-tissue-specific promoter.

7. The method of claim 3, wherein the nucleic acid comprises a polynucleotide sequence encoding a polypeptide having at least 95% identity to the amino acid sequence of SEQ ID NO: 25.

8. The method of claim 3, wherein the nucleic acid encodes a polypeptide that contains a lipid metabolism domain.

9. The method of claim 8, wherein the nucleic acid encodes a polypeptide comprising the sequence of SEQ ID NO: 26.

10. A transgenic plant made by the method of claim 3, wherein expression of the nucleic acid in the plant results in an increased level of fatty acid in a seed as compared to a corresponding wild type variety of the plant.

11. A transgenic plant or part thereof comprising an isolated nucleic acid comprising a polynucleotide sequence encoding a polypeptide that functions in increasing fatty acid content in seed, wherein the polynucleotide sequence is selected from the group consisting of:

a) the polynucleotide sequence of SEQ ID NO: 25;

b) a polynucleotide sequence encoding a polypeptide comprising the amino acid sequence of SEQ ID NO: 26; and c) a polynucleotide sequence encoding a polypeptide comprising an amino acid sequence having at least 95% sequence identity with the amino acid sequence of SEQ ID NO: 26.

12. The transgenic plant of claim 11, wherein the plant is a dicotyledonous plant.

13. The transgenic plant of claim 11, wherein the plant is a monocotyledonous plant.

14. The transgenic plant of claim 11, wherein the plant is an oil producing species.

15. The transgenic plant of claim 11, wherein the plant is selected from the group consisting of rapeseed, canola, linseed, soybean, sunflower, maize, oat, rye, barley, wheat, sugarbeet, tagetes, cotton, oil palm, coconut palm, flax, castor, and peanut.

16. A seed produced by the transgenic plant of claim 11, wherein the plant expresses the polypeptide and wherein the plant is true breeding for an increased level of fatty acid in a seed as compared to a corresponding wild type variety of the plant.

17. The transgenic plant or part thereof of claim 11, wherein the part thereof comprises a seed.

* * * * *